US011739338B2

(12) United States Patent
Henningsen et al.

(10) Patent No.: US 11,739,338 B2
(45) Date of Patent: Aug. 29, 2023

(54) ACETATE TOXICITY TOLERANCE IN RECOMBINANT MICROBIAL HOST CELLS

(71) Applicant: Lallemand Hungary Liquidity Management LLC, Budapest (HU)

(72) Inventors: Brooks Henningsen, Salisbury, NH (US); Sean Covalla, Thetford Center, VT (US); Rintze Zelle, East Thetford, VT (US); Allan Froehlich, Norwich, VT (US)

(73) Assignee: LALLEMAND HUNGARY LIQUIDITY MANAGEMENT LLC, Budapest (HU)

(*) Notice: Subject to any disclaimer, the term of this patent is extended or adjusted under 35 U.S.C. 154(b) by 0 days.

(21) Appl. No.: 16/648,625

(22) PCT Filed: Sep. 18, 2018

(86) PCT No.: PCT/IB2018/057187

§ 371 (c)(1),
(2) Date: Mar. 18, 2020

(87) PCT Pub. No.: WO2019/058260

PCT Pub. Date: Mar. 28, 2019

(65) Prior Publication Data

US 2021/0155944 A1 May 27, 2021

Related U.S. Application Data

(60) Provisional application No. 62/560,364, filed on Sep. 19, 2017.

(51) Int. Cl.

| | |
|---|---|
| ***C12N 15/81*** | (2006.01) |
| ***C07K 14/395*** | (2006.01) |
| ***C12N 9/04*** | (2006.01) |
| ***C12N 9/10*** | (2006.01) |
| ***C12N 9/12*** | (2006.01) |
| ***C12N 9/90*** | (2006.01) |
| ***C12N 9/92*** | (2006.01) |
| ***C12N 9/00*** | (2006.01) |
| ***C12P 7/06*** | (2006.01) |

(52) U.S. Cl.

CPC ............ *C12N 15/81* (2013.01); *C07K 14/395* (2013.01); *C12N 9/0006* (2013.01); *C12N 9/1022* (2013.01); *C12N 9/12* (2013.01); *C12N 9/1205* (2013.01); *C12N 9/90* (2013.01); *C12N 9/92* (2013.01); *C12N 9/93* (2013.01); *C12P 7/06* (2013.01); *C12Y 101/01001* (2013.01); *C12Y 202/01002* (2013.01); *C12Y 207/01017* (2013.01); *C12Y 207/11001* (2013.01); *C12Y 501/03001* (2013.01); *C12Y 503/01006* (2013.01); *C12Y 602/01001* (2013.01)

(58) Field of Classification Search
None
See application file for complete search history.

(56) References Cited

U.S. PATENT DOCUMENTS

| | | | | |
|---|---|---|---|---|
| 2015/0176032 | A1 | 6/2015 | De Bont et al. | |
| 2015/0307872 | A1* | 10/2015 | Sato | C12N 15/1024 435/165 |
| 2016/0002674 | A1 | 1/2016 | Onishi et al. | |
| 2016/0040152 | A1 | 2/2016 | Froehlich et al. | |
| 2019/0106464 | A1* | 4/2019 | Oeser | C12P 7/065 |

FOREIGN PATENT DOCUMENTS

| | | | |
|---|---|---|---|
| WO | 2011/149353 | A1 | 12/2011 |
| WO | 2013/081456 | A2 | 6/2013 |
| WO | 2014/074895 | A2 | 5/2014 |
| WO | 2015/023989 | A1 | 2/2015 |
| WO | 2016/024215 | A1 | 2/2016 |
| WO | 2016/024218 | A1 | 2/2016 |

OTHER PUBLICATIONS

Hasunuma et al., "Co-expression of TAL1 and ADH1 in recombinant xylose-fermenting *Saccharomyces cerevisiae* improves ethanol production from lignocellulosic hydrolysates in the presence of furfural", Journal of Bioscience and Bioengineering vol. 117 No. 2, 165-169, 2014.*

Guadalupe Medina et al., "Elimination of Glycerol Production in Anaerobic Cultures of a *Saccharomyces cerevisiae* Strain Engineered to Use Acetic Acid as an Electron Acceptor," *Applied and Environmental Microbiology* 76(1):190-195, 2010.

Guadalupe-Medina et al., "Evolutionary engineering of a glycerol-3-phosphate dehydrogenase-negative, acetate-reducing *Saccharomyces cerevisiae* strain enables anaerobic growth at high glucose concentrations," *Microb Biotechnol*. 7(1):44-53, 2014.

Henningsen et al., "Increasing Anaerobic Acetate Consumption and Ethanol Yields in *Saccharomyces cerevisiae* with NADPH-Specific Alcohol Dehydrogenase," *Applied and Environmental Microbiology* 81(23):8108-8117, 2015.

(Continued)

*Primary Examiner* — Suzanne M Noakes

(74) *Attorney, Agent, or Firm* — Seed Intellectual Property Law Group LLP

(57) ABSTRACT

Acetate is a potent microbial inhibitor which can affect the performance of yeast in ethanolic fermentation. The present disclosure provides a recombinant microbial host cell having (i) a first genetic modification for increasing the activity of one or more proteins that function in a first metabolic pathway to convert acetate into an alcohol in the microbial host cell; (ii) a second genetic modification for increasing the activity of one or more proteins that function in a second metabolic pathway to import glycerol in the recombinant microbial host cell (iii) a third genetic modification for increasing the activity of one or more proteins that function in a third metabolic pathway to convert a C5 carbohydrate into ethanol in the microbial host cell. The recombinant microbial host cell comprises and natively expresses native proteins that function in a fourth native metabolic pathway to produce glycerol in the microbial host cell.

22 Claims, 12 Drawing Sheets

Specification includes a Sequence Listing.

(56) References Cited

OTHER PUBLICATIONS

Wei et al., "Enhanced biofuel production through coupled acetic acid and xylose consumption by engineered yeast," *Nature Communications* 4:2580, 2013, 8 pages.

Zhang et al., "Improving the ethanol yield by reducing glycerol formation using cofactor regulation in *Saccharomyces cerevisiae*," *Biotechnol Lett* 33:1375-1380, 2011.

Zhang et al., "Optimization of an acetate reduction pathway for producing cellulosic ethanol by engineered yeast," *Biotechnology and Bioengineering* 113(12):2587-2596, 2016.

Wei et al., "Simultaneous Utilization of Cellobiose, Xylose, and Acetic Acid from Lignocellulosic Biomass for Biofuel Production by an Engineered Yeast Platform," *ACS Synth.Biol*. 4:707-713, 2015.

* cited by examiner

SEQUENCE LISTING

<160> NUMBER OF SEQ ID NOS: 20

<210> SEQ ID NO 1
<211> LENGTH: 910
<212> TYPE: PRT
<213> ORGANISM: Bifidobacterium adolescentis

<400> SEQUENCE: 1

```
Met Ala Asp Ala Lys Lys Lys Glu Glu Pro Thr Lys Pro Thr Pro Glu
1               5                   10                  15

Glu Lys Leu Ala Ala Ala Glu Ala Glu Val Asp Ala Leu Val Lys Lys
            20                  25                  30

Gly Leu Lys Ala Leu Asp Glu Phe Glu Lys Leu Asp Gln Lys Gln Val
        35                  40                  45

Asp His Ile Val Ala Lys Ala Ser Val Ala Ala Leu Asn Lys His Leu
    50                  55                  60

Val Leu Ala Lys Met Ala Val Glu Glu Thr His Arg Gly Leu Val Glu
65                  70                  75                  80

Asp Lys Ala Thr Lys Asn Ile Phe Ala Cys Glu His Val Thr Asn Tyr
                85                  90                  95

Leu Ala Gly Gln Lys Thr Val Gly Ile Ile Arg Glu Asp Asp Val Leu
            100                 105                 110

Gly Ile Asp Glu Ile Ala Glu Pro Val Gly Val Val Ala Gly Val Thr
        115                 120                 125

Pro Val Thr Asn Pro Thr Ser Thr Ala Ile Phe Lys Ser Leu Ile Ala
    130                 135                 140

Leu Lys Thr Arg Cys Pro Ile Ile Phe Gly Phe His Pro Gly Ala Gln
145                 150                 155                 160

Asn Cys Ser Val Ala Ala Ala Lys Ile Val Arg Asp Ala Ala Ile Ala
                165                 170                 175

Ala Gly Ala Pro Glu Asn Cys Ile Gln Trp Ile Glu His Pro Ser Ile
            180                 185                 190

Glu Ala Thr Gly Ala Leu Met Lys His Asp Gly Val Ala Thr Ile Leu
        195                 200                 205

Ala Thr Gly Gly Pro Gly Met Val Lys Ala Ala Tyr Ser Ser Gly Lys
    210                 215                 220

Pro Ala Leu Gly Val Gly Ala Gly Asn Ala Pro Ala Tyr Val Asp Lys
225                 230                 235                 240

Asn Val Asp Val Val Arg Ala Ala Asn Asp Leu Ile Leu Ser Lys His
                245                 250                 255

Phe Asp Tyr Gly Met Ile Cys Ala Thr Glu Gln Ala Ile Ile Ala Asp
            260                 265                 270

Lys Asp Ile Tyr Ala Pro Leu Val Lys Glu Leu Lys Arg Arg Lys Ala
        275                 280                 285

Tyr Phe Val Asn Ala Asp Glu Lys Ala Lys Leu Glu Gln Tyr Met Phe
    290                 295                 300

Gly Cys Thr Ala Tyr Ser Gly Gln Thr Pro Lys Leu Asn Ser Val Val
305                 310                 315                 320

Pro Gly Lys Ser Pro Gln Tyr Ile Ala Lys Ala Ala Gly Phe Glu Ile
                325                 330                 335

Pro Glu Asp Ala Thr Ile Leu Ala Ala Glu Cys Lys Glu Val Gly Glu
            340                 345                 350

Asn Glu Pro Leu Thr Met Glu Lys Leu Ala Pro Val Gln Ala Val Leu
        355                 360                 365
```

```
Lys Ser Asp Asn Lys Glu Gln Ala Phe Glu Met Cys Glu Ala Met Leu
    370                 375                 380

Lys His Gly Ala Gly His Thr Ala Ala Ile His Thr Asn Asp Arg Asp
385                 390                 395                 400

Leu Val Arg Glu Tyr Gly Gln Arg Met His Ala Cys Arg Ile Ile Trp
                405                 410                 415

Asn Ser Pro Ser Ser Leu Gly Gly Val Gly Asp Ile Tyr Asn Ala Ile
            420                 425                 430

Ala Pro Ser Leu Thr Leu Gly Cys Gly Ser Tyr Gly Gly Asn Ser Val
        435                 440                 445

Ser Gly Asn Val Gln Ala Val Asn Leu Ile Asn Ile Lys Arg Ile Ala
    450                 455                 460

Arg Arg Asn Asn Asn Met Gln Trp Phe Lys Ile Pro Ala Lys Thr Tyr
465                 470                 475                 480

Phe Glu Pro Asn Ala Ile Lys Tyr Leu Arg Asp Met Tyr Gly Ile Glu
                485                 490                 495

Lys Ala Val Ile Val Cys Asp Lys Val Met Glu Gln Leu Gly Ile Val
            500                 505                 510

Asp Lys Ile Ile Asp Gln Leu Arg Ala Arg Ser Asn Arg Val Thr Phe
        515                 520                 525

Arg Ile Ile Asp Tyr Val Glu Pro Glu Pro Ser Val Glu Thr Val Glu
    530                 535                 540

Arg Gly Ala Ala Met Met Arg Glu Glu Phe Glu Pro Asp Thr Ile Ile
545                 550                 555                 560

Ala Val Gly Gly Gly Ser Pro Met Asp Ala Ser Lys Ile Met Trp Leu
                565                 570                 575

Leu Tyr Glu His Pro Glu Ile Ser Phe Ser Asp Val Arg Glu Lys Phe
            580                 585                 590

Phe Asp Ile Arg Lys Arg Ala Phe Lys Ile Pro Pro Leu Gly Lys Lys
        595                 600                 605

Ala Lys Leu Val Cys Ile Pro Thr Ser Ser Gly Thr Gly Ser Glu Val
    610                 615                 620

Thr Pro Phe Ala Val Ile Thr Asp His Lys Thr Gly Tyr Lys Tyr Pro
625                 630                 635                 640

Ile Thr Asp Tyr Ala Leu Thr Pro Ser Val Ala Ile Val Asp Pro Val
                645                 650                 655

Leu Ala Arg Thr Gln Pro Arg Lys Leu Ala Ser Asp Ala Gly Phe Asp
            660                 665                 670

Ala Leu Thr His Ala Phe Glu Ala Tyr Val Ser Val Tyr Ala Asn Asp
        675                 680                 685

Phe Thr Asp Gly Met Ala Leu His Ala Ala Lys Leu Val Trp Asp Asn
    690                 695                 700

Leu Ala Glu Ser Val Asn Gly Glu Pro Gly Glu Glu Lys Thr Arg Ala
705                 710                 715                 720

Gln Glu Lys Met His Asn Ala Ala Thr Met Ala Gly Met Ala Phe Gly
                725                 730                 735

Ser Ala Phe Leu Gly Met Cys His Gly Met Ala His Thr Ile Gly Ala
            740                 745                 750

Leu Cys His Val Ala His Gly Arg Thr Asn Ser Ile Leu Leu Pro Tyr
        755                 760                 765

Val Ile Arg Tyr Asn Gly Ser Val Pro Glu Glu Pro Thr Ser Trp Pro
    770                 775                 780

Lys Tyr Asn Lys Tyr Ile Ala Pro Glu Arg Tyr Gln Glu Ile Ala Lys
```

```
785                 790                 795                 800

Asn Leu Gly Val Asn Pro Gly Lys Thr Pro Glu Glu Gly Val Glu Asn
                805                 810                 815

Leu Ala Lys Ala Val Glu Asp Tyr Arg Asp Asn Lys Leu Gly Met Asn
            820                 825                 830

Lys Ser Phe Gln Glu Cys Gly Val Asp Glu Asp Tyr Tyr Trp Ser Ile
        835                 840                 845

Ile Asp Gln Ile Gly Met Arg Ala Tyr Glu Asp Gln Cys Ala Pro Ala
    850                 855                 860

Asn Pro Arg Ile Pro Gln Ile Glu Asp Met Lys Asp Ile Ala Ile Ala
865                 870                 875                 880

Ala Tyr Tyr Gly Val Ser Gln Ala Glu Gly His Lys Leu Arg Val Gln
                885                 890                 895

Arg Gln Gly Glu Ala Ala Thr Glu Glu Ala Ser Glu Arg Ala
            900                 905                 910


<210> SEQ ID NO 2
<211> LENGTH: 569
<212> TYPE: PRT
<213> ORGANISM: Saccharomyces cerevisiae

<400> SEQUENCE: 2

Met Lys Asp Leu Lys Leu Ser Asn Phe Lys Gly Lys Phe Ile Ser Arg
1               5                   10                  15

Thr Ser His Trp Gly Leu Thr Gly Lys Lys Leu Arg Tyr Phe Ile Thr
            20                  25                  30

Ile Ala Ser Met Thr Gly Phe Ser Leu Phe Gly Tyr Asp Gln Gly Leu
        35                  40                  45

Met Ala Ser Leu Ile Thr Gly Lys Gln Phe Asn Tyr Glu Phe Pro Ala
    50                  55                  60

Thr Lys Glu Asn Gly Asp His Asp Arg His Ala Thr Val Val Gln Gly
65                  70                  75                  80

Ala Thr Thr Ser Cys Tyr Glu Leu Gly Cys Phe Ala Gly Ser Leu Phe
                85                  90                  95

Val Met Phe Cys Gly Glu Arg Ile Gly Arg Lys Pro Leu Ile Leu Met
            100                 105                 110

Gly Ser Val Ile Thr Ile Ile Gly Ala Val Ile Ser Thr Cys Ala Phe
        115                 120                 125

Arg Gly Tyr Trp Ala Leu Gly Gln Phe Ile Ile Gly Arg Val Val Thr
    130                 135                 140

Gly Val Gly Thr Gly Leu Asn Thr Ser Thr Ile Pro Val Trp Gln Ser
145                 150                 155                 160

Glu Met Ser Lys Ala Glu Asn Arg Gly Leu Leu Val Asn Leu Glu Gly
                165                 170                 175

Ser Thr Ile Ala Phe Gly Thr Met Ile Ala Tyr Trp Ile Asp Phe Gly
            180                 185                 190

Leu Ser Tyr Thr Asn Ser Ser Val Gln Trp Arg Phe Pro Val Ser Met
        195                 200                 205

Gln Ile Val Phe Ala Leu Phe Leu Leu Ala Phe Met Ile Lys Leu Pro
    210                 215                 220

Glu Ser Pro Arg Trp Leu Ile Ser Gln Ser Arg Thr Glu Glu Ala Arg
225                 230                 235                 240

Tyr Leu Val Gly Thr Leu Asp Asp Ala Asp Pro Asn Asp Glu Glu Val
                245                 250                 255
```

```
Ile Thr Glu Val Ala Met Leu His Asp Ala Val Asn Arg Thr Lys His
            260                 265                 270

Glu Lys His Ser Leu Ser Ser Leu Phe Ser Arg Gly Arg Ser Gln Asn
        275                 280                 285

Leu Gln Arg Ala Leu Ile Ala Ala Ser Thr Gln Phe Phe Gln Gln Phe
    290                 295                 300

Thr Gly Cys Asn Ala Ala Ile Tyr Tyr Ser Thr Val Leu Phe Asn Lys
305                 310                 315                 320

Thr Ile Lys Leu Asp Tyr Arg Leu Ser Met Ile Ile Gly Gly Val Phe
                325                 330                 335

Ala Thr Ile Tyr Ala Leu Ser Thr Ile Gly Ser Phe Phe Leu Ile Glu
            340                 345                 350

Lys Leu Gly Arg Arg Lys Leu Phe Leu Leu Gly Ala Thr Gly Gln Ala
        355                 360                 365

Val Ser Phe Thr Ile Thr Phe Ala Cys Leu Val Lys Glu Asn Lys Glu
    370                 375                 380

Asn Ala Arg Gly Ala Ala Val Gly Leu Phe Leu Phe Ile Thr Phe Phe
385                 390                 395                 400

Gly Leu Ser Leu Leu Ser Leu Pro Trp Ile Tyr Pro Pro Glu Ile Ala
                405                 410                 415

Ser Met Lys Val Arg Ala Ser Thr Asn Ala Phe Ser Thr Cys Thr Asn
            420                 425                 430

Trp Leu Cys Asn Phe Ala Val Val Met Phe Thr Pro Ile Phe Ile Gly
        435                 440                 445

Gln Ser Gly Trp Gly Cys Tyr Leu Phe Phe Ala Val Met Asn Tyr Leu
    450                 455                 460

Tyr Ile Pro Val Ile Phe Phe Phe Tyr Pro Glu Thr Ala Gly Arg Ser
465                 470                 475                 480

Leu Glu Glu Ile Asp Ile Ile Phe Ala Lys Ala Tyr Glu Asp Gly Thr
                485                 490                 495

Gln Pro Trp Arg Val Ala Asn His Leu Pro Lys Leu Ser Leu Gln Glu
            500                 505                 510

Val Glu Asp His Ala Asn Ala Leu Gly Ser Tyr Asp Asp Glu Met Glu
        515                 520                 525

Lys Glu Asp Phe Gly Glu Asp Arg Val Glu Asp Thr Tyr Asn Gln Ile
    530                 535                 540

Asn Gly Asp Asn Ser Ser Ser Ser Ser Asn Ile Lys Asn Glu Asp Thr
545                 550                 555                 560

Val Asn Asp Lys Ala Asn Phe Glu Gly
                565
```

<210> SEQ ID NO 3
<211> LENGTH: 683
<212> TYPE: PRT
<213> ORGANISM: Saccharomyces cerevisiae

<400> SEQUENCE: 3

```
Met Thr Ile Lys Glu His Lys Val Val Tyr Glu Ala His Asn Val Lys
1               5                   10                  15

Ala Leu Lys Ala Pro Gln His Phe Tyr Asn Ser Gln Pro Gly Lys Gly
            20                  25                  30

Tyr Val Thr Asp Met Gln His Tyr Gln Glu Met Tyr Gln Gln Ser Ile
        35                  40                  45

Asn Glu Pro Glu Lys Phe Phe Asp Lys Met Ala Lys Glu Tyr Leu His
    50                  55                  60
```

```
Trp Asp Ala Pro Tyr Thr Lys Val Gln Ser Gly Ser Leu Asn Asn Gly
65                  70                  75                  80

Asp Val Ala Trp Phe Leu Asn Gly Lys Leu Asn Ala Ser Tyr Asn Cys
                85                  90                  95

Val Asp Arg His Ala Phe Ala Asn Pro Asp Lys Pro Ala Leu Ile Tyr
            100                 105                 110

Glu Ala Asp Asp Glu Ser Asp Asn Lys Ile Ile Thr Phe Gly Glu Leu
        115                 120                 125

Leu Arg Lys Val Ser Gln Ile Ala Gly Val Leu Lys Ser Trp Gly Val
    130                 135                 140

Lys Lys Gly Asp Thr Val Ala Ile Tyr Leu Pro Met Ile Pro Glu Ala
145                 150                 155                 160

Val Ile Ala Met Leu Ala Val Ala Arg Ile Gly Ala Ile His Ser Val
                165                 170                 175

Val Phe Ala Gly Phe Ser Ala Gly Ser Leu Lys Asp Arg Val Val Asp
            180                 185                 190

Ala Asn Ser Lys Val Val Ile Thr Cys Asp Glu Gly Lys Arg Gly Gly
        195                 200                 205

Lys Thr Ile Asn Thr Lys Lys Ile Val Asp Glu Gly Leu Asn Gly Val
    210                 215                 220

Asp Leu Val Ser Arg Ile Leu Val Phe Gln Arg Thr Gly Thr Glu Gly
225                 230                 235                 240

Ile Pro Met Lys Ala Gly Arg Asp Tyr Trp Trp His Glu Glu Ala Ala
                245                 250                 255

Lys Gln Arg Thr Tyr Leu Pro Pro Val Ser Cys Asp Ala Glu Asp Pro
            260                 265                 270

Leu Phe Leu Leu Tyr Thr Ser Gly Ser Thr Gly Ser Pro Lys Gly Val
        275                 280                 285

Val His Thr Thr Gly Gly Tyr Leu Leu Gly Ala Ala Leu Thr Thr Arg
    290                 295                 300

Tyr Val Phe Asp Ile His Pro Glu Asp Val Leu Phe Thr Ala Gly Asp
305                 310                 315                 320

Val Gly Trp Ile Thr Gly His Thr Tyr Ala Leu Tyr Gly Pro Leu Thr
                325                 330                 335

Leu Gly Thr Ala Ser Ile Ile Phe Glu Ser Thr Pro Ala Tyr Pro Asp
            340                 345                 350

Tyr Gly Arg Tyr Trp Arg Ile Ile Gln Arg His Lys Ala Thr His Phe
        355                 360                 365

Tyr Val Ala Pro Thr Ala Leu Arg Leu Ile Lys Arg Val Gly Glu Ala
    370                 375                 380

Glu Ile Ala Lys Tyr Asp Thr Ser Ser Leu Arg Val Leu Gly Ser Val
385                 390                 395                 400

Gly Glu Pro Ile Ser Pro Asp Leu Trp Glu Trp Tyr His Glu Lys Val
                405                 410                 415

Gly Asn Lys Asn Cys Val Ile Cys Asp Thr Met Trp Gln Thr Glu Ser
            420                 425                 430

Gly Ser His Leu Ile Ala Pro Leu Ala Gly Ala Val Pro Thr Lys Pro
        435                 440                 445

Gly Ser Ala Thr Val Pro Phe Phe Gly Ile Asn Ala Cys Ile Ile Asp
    450                 455                 460

Pro Val Thr Gly Val Glu Leu Glu Gly Asn Asp Val Glu Gly Val Leu
465                 470                 475                 480
```

```
Ala Val Lys Ser Pro Trp Pro Ser Met Ala Arg Ser Val Trp Asn His
                485                 490                 495

His Asp Arg Tyr Met Asp Thr Tyr Leu Lys Pro Tyr Pro Gly His Tyr
            500                 505                 510

Phe Thr Gly Asp Gly Ala Gly Arg Asp His Asp Gly Tyr Tyr Trp Ile
        515                 520                 525

Arg Gly Arg Val Asp Asp Val Val Asn Val Ser Gly His Arg Leu Ser
    530                 535                 540

Thr Ser Glu Ile Glu Ala Ser Ile Ser Asn His Glu Asn Val Ser Glu
545                 550                 555                 560

Ala Ala Val Val Gly Ile Pro Asp Glu Leu Thr Gly Gln Thr Val Val
                565                 570                 575

Ala Tyr Val Ser Leu Lys Asp Gly Tyr Leu Gln Asn Asn Ala Thr Glu
            580                 585                 590

Gly Asp Ala Glu His Ile Thr Pro Asp Asn Leu Arg Arg Glu Leu Ile
        595                 600                 605

Leu Gln Val Arg Gly Glu Ile Gly Pro Phe Ala Ser Pro Lys Thr Ile
    610                 615                 620

Ile Leu Val Arg Asp Leu Pro Arg Thr Arg Ser Gly Lys Ile Met Arg
625                 630                 635                 640

Arg Val Leu Arg Lys Val Ala Ser Asn Glu Ala Glu Gln Leu Gly Asp
                645                 650                 655

Leu Thr Thr Leu Ala Asn Pro Glu Val Val Pro Ala Ile Ile Ser Ala
            660                 665                 670

Val Glu Asn Gln Phe Phe Ser Gln Lys Lys Lys
        675                 680


<210> SEQ ID NO 4
<211> LENGTH: 360
<212> TYPE: PRT
<213> ORGANISM: Entamoeba histolytica

<400> SEQUENCE: 4

Met Lys Gly Leu Ala Met Leu Gly Ile Gly Arg Ile Gly Trp Ile Glu
1               5                   10                  15

Lys Lys Ile Pro Glu Cys Gly Pro Leu Asp Ala Leu Val Arg Pro Leu
            20                  25                  30

Ala Leu Ala Pro Cys Thr Ser Asp Thr His Thr Val Trp Ala Gly Ala
        35                  40                  45

Ile Gly Asp Arg His Asp Met Ile Leu Gly His Glu Ala Val Gly Gln
    50                  55                  60

Ile Val Lys Val Gly Ser Leu Val Lys Arg Leu Lys Val Gly Asp Lys
65                  70                  75                  80

Val Ile Val Pro Ala Ile Thr Pro Asp Trp Gly Glu Glu Glu Ser Gln
                85                  90                  95

Arg Gly Tyr Pro Met His Ser Gly Gly Met Leu Gly Gly Trp Lys Phe
            100                 105                 110

Ser Asn Phe Lys Asp Gly Val Phe Ser Glu Val Phe His Val Asn Glu
        115                 120                 125

Ala Asp Ala Asn Leu Ala Leu Leu Pro Arg Asp Ile Lys Pro Glu Asp
    130                 135                 140

Ala Val Met Leu Ser Asp Met Val Thr Thr Gly Phe His Gly Ala Glu
145                 150                 155                 160

Leu Ala Asn Ile Lys Leu Gly Asp Thr Val Cys Val Ile Gly Ile Gly
                165                 170                 175
```

```
Pro Val Gly Leu Met Ser Val Ala Gly Ala Asn His Leu Gly Ala Gly
            180                 185                 190

Arg Ile Phe Ala Val Gly Ser Arg Lys His Cys Cys Asp Ile Ala Leu
        195                 200                 205

Glu Tyr Gly Ala Thr Asp Ile Ile Asn Tyr Lys Asn Gly Asp Ile Val
    210                 215                 220

Glu Gln Ile Leu Lys Ala Thr Asp Gly Lys Gly Val Asp Lys Val Val
225                 230                 235                 240

Ile Ala Gly Gly Asp Val His Thr Phe Ala Gln Ala Val Lys Met Ile
                245                 250                 255

Lys Pro Gly Ser Asp Ile Gly Asn Val Asn Tyr Leu Gly Glu Gly Asp
            260                 265                 270

Asn Ile Asp Ile Pro Arg Ser Glu Trp Gly Val Gly Met Gly His Lys
        275                 280                 285

His Ile His Gly Gly Leu Thr Pro Gly Gly Arg Val Arg Met Glu Lys
    290                 295                 300

Leu Ala Ser Leu Ile Ser Thr Gly Lys Leu Asp Thr Ser Lys Leu Ile
305                 310                 315                 320

Thr His Arg Phe Glu Gly Leu Glu Lys Val Glu Asp Ala Leu Met Leu
                325                 330                 335

Met Lys Asn Lys Pro Ala Asp Leu Ile Lys Pro Val Val Arg Ile His
            340                 345                 350

Tyr Asp Asp Glu Asp Thr Leu His
        355                 360


<210> SEQ ID NO 5
<211> LENGTH: 1710
<212> TYPE: DNA
<213> ORGANISM: Saccharomyces paradoxus
<220> FEATURE:
<221> NAME/KEY: CDS
<222> LOCATION: (1)..(1710)

<400> SEQUENCE: 5

atg aag gac tcc aag ttg tct aag ttc aag ggt aga ttc atg tcc aga       48
Met Lys Asp Ser Lys Leu Ser Lys Phe Lys Gly Arg Phe Met Ser Arg
1               5                   10                  15

act tct cat tgg ggt ttg act ggt caa aag ttg aga tac ttc att acc       96
Thr Ser His Trp Gly Leu Thr Gly Gln Lys Leu Arg Tyr Phe Ile Thr
            20                  25                  30

att gct tct atg acc ggt ttc tct ttg ttt ggt tat gac caa ggt ttg      144
Ile Ala Ser Met Thr Gly Phe Ser Leu Phe Gly Tyr Asp Gln Gly Leu
        35                  40                  45

atg gcc tct ttg att act ggt aag caa ttc aac tac gaa ttc cca gct      192
Met Ala Ser Leu Ile Thr Gly Lys Gln Phe Asn Tyr Glu Phe Pro Ala
    50                  55                  60

acc aaa gaa aac ggt gat cat gat aga cat gct acc gtt gtt caa ggt      240
Thr Lys Glu Asn Gly Asp His Asp Arg His Ala Thr Val Val Gln Gly
65                  70                  75                  80

gct act act tct tgt tat gaa ttg ggt tgt ttc gcc ggt tct ttg ttc      288
Ala Thr Thr Ser Cys Tyr Glu Leu Gly Cys Phe Ala Gly Ser Leu Phe
                85                  90                  95

gtt atg ttt tac ggt gaa aga atc ggt aga aag cca ttg att ttg atg      336
Val Met Phe Tyr Gly Glu Arg Ile Gly Arg Lys Pro Leu Ile Leu Met
            100                 105                 110

ggt tcc att atc acc att atc ggt gct gtt att tct acc tgt gct ttc      384
Gly Ser Ile Ile Thr Ile Ile Gly Ala Val Ile Ser Thr Cys Ala Phe
        115                 120                 125
```

```
aga gat tat tgg gct ttg ggt caa ttc atc gtt ggt aga gtt gtt act      432
Arg Asp Tyr Trp Ala Leu Gly Gln Phe Ile Val Gly Arg Val Val Thr
    130                 135                 140

ggt gtt ggt act ggt ttg aac act tct act att cca gtt tgg caa tcc      480
Gly Val Gly Thr Gly Leu Asn Thr Ser Thr Ile Pro Val Trp Gln Ser
145                 150                 155                 160

gaa atg tct aag gct gaa aac aga ggt ttg ttg gtt aac ttg gaa ggt      528
Glu Met Ser Lys Ala Glu Asn Arg Gly Leu Leu Val Asn Leu Glu Gly
                165                 170                 175

tcc act att gct ttc ggt act atg att gct tac tgg atc gat ttc ggt      576
Ser Thr Ile Ala Phe Gly Thr Met Ile Ala Tyr Trp Ile Asp Phe Gly
            180                 185                 190

ttt tcc tac act aac tct tcc gtt caa tgg aga ttt cca gtc tct atg      624
Phe Ser Tyr Thr Asn Ser Ser Val Gln Trp Arg Phe Pro Val Ser Met
        195                 200                 205

caa atc gtt ttc gcc ttg ttt ttg ttg gcc ttc atg att aag ttg cca      672
Gln Ile Val Phe Ala Leu Phe Leu Leu Ala Phe Met Ile Lys Leu Pro
    210                 215                 220

gaa tct cca aga tgg ttg atc tct caa tct aga act gaa gaa gcc aga      720
Glu Ser Pro Arg Trp Leu Ile Ser Gln Ser Arg Thr Glu Glu Ala Arg
225                 230                 235                 240

tac ttg gtt ggt act ttg gat gat act gat cca aac gat gaa gaa gtt      768
Tyr Leu Val Gly Thr Leu Asp Asp Thr Asp Pro Asn Asp Glu Glu Val
                245                 250                 255

att acc gaa gtt gcc atg ttg cat gat gcc gtt aat aga act aag cac      816
Ile Thr Glu Val Ala Met Leu His Asp Ala Val Asn Arg Thr Lys His
            260                 265                 270

gaa aag cac tca ttg tca tcc ttg ttt tct aga ggt aag tcc caa aac      864
Glu Lys His Ser Leu Ser Ser Leu Phe Ser Arg Gly Lys Ser Gln Asn
        275                 280                 285

ttg caa aga gct ttg att gct gct tct acc caa ttc ttc caa caa ttc      912
Leu Gln Arg Ala Leu Ile Ala Ala Ser Thr Gln Phe Phe Gln Gln Phe
    290                 295                 300

act ggt tgt aat gct gcc atc tac tac tct act gtt ttg ttc aac aag      960
Thr Gly Cys Asn Ala Ala Ile Tyr Tyr Ser Thr Val Leu Phe Asn Lys
305                 310                 315                 320

acc atc aag ttg gac cac aga ttg tcc atg att att ggt ggt gtt ttc     1008
Thr Ile Lys Leu Asp His Arg Leu Ser Met Ile Ile Gly Gly Val Phe
                325                 330                 335

gct act atc tac gcc ttg tct act att ggt tcc ttc ttc ttg atc gaa     1056
Ala Thr Ile Tyr Ala Leu Ser Thr Ile Gly Ser Phe Phe Leu Ile Glu
            340                 345                 350

aaa tta ggt aga aga aag ttg ttc ttg ttg ggt gct act ggt caa gct     1104
Lys Leu Gly Arg Arg Lys Leu Phe Leu Leu Gly Ala Thr Gly Gln Ala
        355                 360                 365

gtt tct ttc act att acc ttt gct tgc ttg gta aaa gaa aac aaa gaa     1152
Val Ser Phe Thr Ile Thr Phe Ala Cys Leu Val Lys Glu Asn Lys Glu
    370                 375                 380

aat gct aga ggt gct gcc gtt ggt ttg ttc tta ttc att act ttc ttc     1200
Asn Ala Arg Gly Ala Ala Val Gly Leu Phe Leu Phe Ile Thr Phe Phe
385                 390                 395                 400

ggt ttg tcc ttg ttg tct ttg cca tgg atc tat cca cca gaa att gct     1248
Gly Leu Ser Leu Leu Ser Leu Pro Trp Ile Tyr Pro Pro Glu Ile Ala
                405                 410                 415

tca atg aag gtt aga gca tct acc aat gct ttc tct act tgt aca aac     1296
Ser Met Lys Val Arg Ala Ser Thr Asn Ala Phe Ser Thr Cys Thr Asn
            420                 425                 430

tgg ttg tgc aat ttc gcc gtt gtt atg ttc acc cca att ttc att ggt     1344
Trp Leu Cys Asn Phe Ala Val Val Met Phe Thr Pro Ile Phe Ile Gly
```

```
        435                 440                 445

caa tct ggt tgg ggt tgt tac ttg ttt ttt gcc gtt atg aac tac ttg      1392
Gln Ser Gly Trp Gly Cys Tyr Leu Phe Phe Ala Val Met Asn Tyr Leu
    450                 455                 460

tat atc cca gtt ata ttc ttt ttc tac cct gaa acc gct ggt aga tcc      1440
Tyr Ile Pro Val Ile Phe Phe Phe Tyr Pro Glu Thr Ala Gly Arg Ser
465                 470                 475                 480

ttg gaa gaa att gat att atc ttc gcc aag gcc tac gaa gat ggt act      1488
Leu Glu Glu Ile Asp Ile Ile Phe Ala Lys Ala Tyr Glu Asp Gly Thr
                485                 490                 495

caa cct tgg aga gtt gct aat cat ttg cca aag ttg tcc ttg caa gaa      1536
Gln Pro Trp Arg Val Ala Asn His Leu Pro Lys Leu Ser Leu Gln Glu
            500                 505                 510

gtt gaa gat cac gct aat gct ttg ggt tct tat gat gac gaa atg gaa      1584
Val Glu Asp His Ala Asn Ala Leu Gly Ser Tyr Asp Asp Glu Met Glu
        515                 520                 525

aag gat gat ttc gcc gaa gat aga gtc gaa gat acc tac aat caa atc      1632
Lys Asp Asp Phe Ala Glu Asp Arg Val Glu Asp Thr Tyr Asn Gln Ile
    530                 535                 540

aac ggt gac aac tcc tct tcc tcc tct aat atc aaa aac gaa gat act      1680
Asn Gly Asp Asn Ser Ser Ser Ser Ser Asn Ile Lys Asn Glu Asp Thr
545                 550                 555                 560

gtt aac gac aag gcc aac tct gaa tct tga                              1710
Val Asn Asp Lys Ala Asn Ser Glu Ser
                565


<210> SEQ ID NO 6
<211> LENGTH: 569
<212> TYPE: PRT
<213> ORGANISM: Saccharomyces paradoxus

<400> SEQUENCE: 6

Met Lys Asp Ser Lys Leu Ser Lys Phe Lys Gly Arg Phe Met Ser Arg
1               5                   10                  15

Thr Ser His Trp Gly Leu Thr Gly Gln Lys Leu Arg Tyr Phe Ile Thr
            20                  25                  30

Ile Ala Ser Met Thr Gly Phe Ser Leu Phe Gly Tyr Asp Gln Gly Leu
        35                  40                  45

Met Ala Ser Leu Ile Thr Gly Lys Gln Phe Asn Tyr Glu Phe Pro Ala
    50                  55                  60

Thr Lys Glu Asn Gly Asp His Asp Arg His Ala Thr Val Val Gln Gly
65                  70                  75                  80

Ala Thr Thr Ser Cys Tyr Glu Leu Gly Cys Phe Ala Gly Ser Leu Phe
                85                  90                  95

Val Met Phe Tyr Gly Glu Arg Ile Gly Arg Lys Pro Leu Ile Leu Met
            100                 105                 110

Gly Ser Ile Ile Thr Ile Ile Gly Ala Val Ile Ser Thr Cys Ala Phe
        115                 120                 125

Arg Asp Tyr Trp Ala Leu Gly Gln Phe Ile Val Gly Arg Val Val Thr
    130                 135                 140

Gly Val Gly Thr Gly Leu Asn Thr Ser Thr Ile Pro Val Trp Gln Ser
145                 150                 155                 160

Glu Met Ser Lys Ala Glu Asn Arg Gly Leu Leu Val Asn Leu Glu Gly
                165                 170                 175

Ser Thr Ile Ala Phe Gly Thr Met Ile Ala Tyr Trp Ile Asp Phe Gly
            180                 185                 190

Phe Ser Tyr Thr Asn Ser Ser Val Gln Trp Arg Phe Pro Val Ser Met
```

```
        195                 200                 205

Gln Ile Val Phe Ala Leu Phe Leu Leu Ala Phe Met Ile Lys Leu Pro
    210                 215                 220

Glu Ser Pro Arg Trp Leu Ile Ser Gln Ser Arg Thr Glu Glu Ala Arg
225                 230                 235                 240

Tyr Leu Val Gly Thr Leu Asp Asp Thr Asp Pro Asn Asp Glu Glu Val
                245                 250                 255

Ile Thr Glu Val Ala Met Leu His Asp Ala Val Asn Arg Thr Lys His
            260                 265                 270

Glu Lys His Ser Leu Ser Ser Leu Phe Ser Arg Gly Lys Ser Gln Asn
        275                 280                 285

Leu Gln Arg Ala Leu Ile Ala Ala Ser Thr Gln Phe Phe Gln Gln Phe
    290                 295                 300

Thr Gly Cys Asn Ala Ala Ile Tyr Tyr Ser Thr Val Leu Phe Asn Lys
305                 310                 315                 320

Thr Ile Lys Leu Asp His Arg Leu Ser Met Ile Ile Gly Gly Val Phe
                325                 330                 335

Ala Thr Ile Tyr Ala Leu Ser Thr Ile Gly Ser Phe Phe Leu Ile Glu
            340                 345                 350

Lys Leu Gly Arg Arg Lys Leu Phe Leu Leu Gly Ala Thr Gly Gln Ala
        355                 360                 365

Val Ser Phe Thr Ile Thr Phe Ala Cys Leu Val Lys Glu Asn Lys Glu
    370                 375                 380

Asn Ala Arg Gly Ala Ala Val Gly Leu Phe Leu Phe Ile Thr Phe Phe
385                 390                 395                 400

Gly Leu Ser Leu Leu Ser Leu Pro Trp Ile Tyr Pro Pro Glu Ile Ala
                405                 410                 415

Ser Met Lys Val Arg Ala Ser Thr Asn Ala Phe Ser Thr Cys Thr Asn
            420                 425                 430

Trp Leu Cys Asn Phe Ala Val Val Met Phe Thr Pro Ile Phe Ile Gly
        435                 440                 445

Gln Ser Gly Trp Gly Cys Tyr Leu Phe Phe Ala Val Met Asn Tyr Leu
    450                 455                 460

Tyr Ile Pro Val Ile Phe Phe Phe Tyr Pro Glu Thr Ala Gly Arg Ser
465                 470                 475                 480

Leu Glu Glu Ile Asp Ile Ile Phe Ala Lys Ala Tyr Glu Asp Gly Thr
                485                 490                 495

Gln Pro Trp Arg Val Ala Asn His Leu Pro Lys Leu Ser Leu Gln Glu
            500                 505                 510

Val Glu Asp His Ala Asn Ala Leu Gly Ser Tyr Asp Asp Glu Met Glu
        515                 520                 525

Lys Asp Asp Phe Ala Glu Asp Arg Val Glu Asp Thr Tyr Asn Gln Ile
    530                 535                 540

Asn Gly Asp Asn Ser Ser Ser Ser Ser Asn Ile Lys Asn Glu Asp Thr
545                 550                 555                 560

Val Asn Asp Lys Ala Asn Ser Glu Ser
                565
```

<210> SEQ ID NO 7
<211> LENGTH: 1713
<212> TYPE: DNA
<213> ORGANISM: Pichia sorbitophila
<220> FEATURE:
<221> NAME/KEY: CDS
<222> LOCATION: (1)..(1713)

```
<400> SEQUENCE: 7

atg gga ttc gaa ctt tgg gga agg acc aac aca ggt ggt ttg aga ggt       48
Met Gly Phe Glu Leu Trp Gly Arg Thr Asn Thr Gly Gly Leu Arg Gly
1               5                   10                  15

aga cct ctt cgt gtt gcc atc acc gct gtt gca act act ggt ttc tcc       96
Arg Pro Leu Arg Val Ala Ile Thr Ala Val Ala Thr Thr Gly Phe Ser
            20                  25                  30

ctt ttc ggt tat gat cag ggt ttg atg tct ggt att att acc ggt act      144
Leu Phe Gly Tyr Asp Gln Gly Leu Met Ser Gly Ile Ile Thr Gly Thr
        35                  40                  45

gaa ttt aac gag gag ttc cct cca acc tgg tcc aag cca cat tac aac      192
Glu Phe Asn Glu Glu Phe Pro Pro Thr Trp Ser Lys Pro His Tyr Asn
    50                  55                  60

gcg tct gag aag aga cat gct act gtt gtt caa ggt gct gtt aca gct      240
Ala Ser Glu Lys Arg His Ala Thr Val Val Gln Gly Ala Val Thr Ala
65                  70                  75                  80

tgt tac gaa att ggt tgt ttc ttc ggt gct ctt ttt gct ttg gtt aga      288
Cys Tyr Glu Ile Gly Cys Phe Phe Gly Ala Leu Phe Ala Leu Val Arg
                85                  90                  95

ggt gac agg atc ggt aga cgt cca ctt gtc att gtt ggt gct gtt ctt      336
Gly Asp Arg Ile Gly Arg Arg Pro Leu Val Ile Val Gly Ala Val Leu
            100                 105                 110

atc atc att ggt act gtt att tct act gct gct ttt ggt gaa cac tgg      384
Ile Ile Ile Gly Thr Val Ile Ser Thr Ala Ala Phe Gly Glu His Trp
        115                 120                 125

ggt ttg ggt caa ttc gtt att ggt aga gtt att act ggt att ggt aac      432
Gly Leu Gly Gln Phe Val Ile Gly Arg Val Ile Thr Gly Ile Gly Asn
    130                 135                 140

ggt atg aac aca gca act atc cca gtc tgg caa tct gag atc tct cgt      480
Gly Met Asn Thr Ala Thr Ile Pro Val Trp Gln Ser Glu Ile Ser Arg
145                 150                 155                 160

cca gaa aac aga ggt aag tta gtc aac ttg gaa ggt tca gtc att gcc      528
Pro Glu Asn Arg Gly Lys Leu Val Asn Leu Glu Gly Ser Val Ile Ala
                165                 170                 175

att ggt act ttc gtt gct tac tgg att gat ttc ggt ctc tcc tac gtt      576
Ile Gly Thr Phe Val Ala Tyr Trp Ile Asp Phe Gly Leu Ser Tyr Val
            180                 185                 190

aac agc tct gta caa tgg aga ttc cct gtt gcg ttc caa att gtt ttt      624
Asn Ser Ser Val Gln Trp Arg Phe Pro Val Ala Phe Gln Ile Val Phe
        195                 200                 205

gct gct gga ctt ctt gga ggt att ctt ttc atg ccg gag tct cct aga      672
Ala Ala Gly Leu Leu Gly Gly Ile Leu Phe Met Pro Glu Ser Pro Arg
    210                 215                 220

tgg ttg ctc gct cat ggc aag aag gag caa gca cac ata gtc tta ggt      720
Trp Leu Leu Ala His Gly Lys Lys Glu Gln Ala His Ile Val Leu Gly
225                 230                 235                 240

gct ttg aat gat ctc gac cct aat gat gac cat gtc ctt gct gag agt      768
Ala Leu Asn Asp Leu Asp Pro Asn Asp Asp His Val Leu Ala Glu Ser
                245                 250                 255

act gtt att acc gat gct att aac aga ttc tcc agg tct caa ctt ggt      816
Thr Val Ile Thr Asp Ala Ile Asn Arg Phe Ser Arg Ser Gln Leu Gly
            260                 265                 270

ttc aag gaa ctt atg tcc ggt ggt aag aac caa cat ttt gct aga atg      864
Phe Lys Glu Leu Met Ser Gly Gly Lys Asn Gln His Phe Ala Arg Met
        275                 280                 285

gtt att ggt tct tcc act caa ttt ttc caa cag ttc act ggt tgt aat      912
Val Ile Gly Ser Ser Thr Gln Phe Phe Gln Gln Phe Thr Gly Cys Asn
    290                 295                 300
```

-continued

```
gct gcc att tac tat tca aca gtt ttg ttc gaa gag acc att ttc gtc      960
Ala Ala Ile Tyr Tyr Ser Thr Val Leu Phe Glu Glu Thr Ile Phe Val
305                 310                 315                 320

ggt gac aga aga ttg tct ttg gtt atg ggt ggt gtt ttc gct tcc gta     1008
Gly Asp Arg Arg Leu Ser Leu Val Met Gly Gly Val Phe Ala Ser Val
                325                 330                 335

tac gcc ctt gcc act att cca tct ttc ttc tta gtc gat aag ctt ggt     1056
Tyr Ala Leu Ala Thr Ile Pro Ser Phe Phe Leu Val Asp Lys Leu Gly
            340                 345                 350

aga aga aac ttg ttc ttg att ggt gct act ggt caa gct ttg tct ttc     1104
Arg Arg Asn Leu Phe Leu Ile Gly Ala Thr Gly Gln Ala Leu Ser Phe
        355                 360                 365

acc att aca ttt gct tgt ttg atc aac cca aca aag caa aat gct aag     1152
Thr Ile Thr Phe Ala Cys Leu Ile Asn Pro Thr Lys Gln Asn Ala Lys
    370                 375                 380

ggt gca gct gtt ggt atc ttc ttg ttt atc acc ttc ttc gcc ttt aca     1200
Gly Ala Ala Val Gly Ile Phe Leu Phe Ile Thr Phe Phe Ala Phe Thr
385                 390                 395                 400

att ttg cca ttg cct tgg att tac cca cca gaa atc aac cca ttg aga     1248
Ile Leu Pro Leu Pro Trp Ile Tyr Pro Pro Glu Ile Asn Pro Leu Arg
                405                 410                 415

aca aga act gtt gcc tct gcc gtt tct aca tgt acc aat tgg ctt aca     1296
Thr Arg Thr Val Ala Ser Ala Val Ser Thr Cys Thr Asn Trp Leu Thr
            420                 425                 430

aac ttt gcc gtc gtt atg ttt act cct att ttc att aac gat gct caa     1344
Asn Phe Ala Val Val Met Phe Thr Pro Ile Phe Ile Asn Asp Ala Gln
        435                 440                 445

tgg ggt tgt tac ttg ttc ttt gct tgt ttg aac tac gct ttc att cca     1392
Trp Gly Cys Tyr Leu Phe Phe Ala Cys Leu Asn Tyr Ala Phe Ile Pro
    450                 455                 460

gtt atc ttc tgg ttc tac cca gaa act gct ggc cgt tcc ttg gaa gaa     1440
Val Ile Phe Trp Phe Tyr Pro Glu Thr Ala Gly Arg Ser Leu Glu Glu
465                 470                 475                 480

att gat atc att ttc gcg aag gct tac act gat gga aga cct cca tgg     1488
Ile Asp Ile Ile Phe Ala Lys Ala Tyr Thr Asp Gly Arg Pro Pro Trp
                485                 490                 495

aga gtt gct gct acc atg cca cac ttg tct ttg aag gaa caa gag gag     1536
Arg Val Ala Ala Thr Met Pro His Leu Ser Leu Lys Glu Gln Glu Glu
            500                 505                 510

caa ggt atg caa ctc gga ctt tat gac aat gaa gct gag aaa cag aag     1584
Gln Gly Met Gln Leu Gly Leu Tyr Asp Asn Glu Ala Glu Lys Gln Lys
        515                 520                 525

ttc gag caa acc gag aac ttg atg tct tct agc tct tct gcg aag ctt     1632
Phe Glu Gln Thr Glu Asn Leu Met Ser Ser Ser Ser Ser Ala Lys Leu
    530                 535                 540

cct gaa gag gga tct aac gta aac gag aat gag aac gaa aac acg aac     1680
Pro Glu Glu Gly Ser Asn Val Asn Glu Asn Glu Asn Glu Asn Thr Asn
545                 550                 555                 560

gaa aag gat caa aca cca aag cca act gat gtt                         1713
Glu Lys Asp Gln Thr Pro Lys Pro Thr Asp Val
                565                 570


<210> SEQ ID NO 8
<211> LENGTH: 571
<212> TYPE: PRT
<213> ORGANISM: Pichia sorbitophila

<400> SEQUENCE: 8

Met Gly Phe Glu Leu Trp Gly Arg Thr Asn Thr Gly Gly Leu Arg Gly
1               5                   10                  15
```

```
Arg Pro Leu Arg Val Ala Ile Thr Ala Val Ala Thr Thr Gly Phe Ser
            20                  25                  30

Leu Phe Gly Tyr Asp Gln Gly Leu Met Ser Gly Ile Ile Thr Gly Thr
        35                  40                  45

Glu Phe Asn Glu Glu Phe Pro Pro Thr Trp Ser Lys Pro His Tyr Asn
    50                  55                  60

Ala Ser Glu Lys Arg His Ala Thr Val Val Gln Gly Ala Val Thr Ala
65                  70                  75                  80

Cys Tyr Glu Ile Gly Cys Phe Phe Gly Ala Leu Phe Ala Leu Val Arg
                85                  90                  95

Gly Asp Arg Ile Gly Arg Arg Pro Leu Val Ile Val Gly Ala Val Leu
            100                 105                 110

Ile Ile Ile Gly Thr Val Ile Ser Thr Ala Ala Phe Gly Glu His Trp
        115                 120                 125

Gly Leu Gly Gln Phe Val Ile Gly Arg Val Ile Thr Gly Ile Gly Asn
    130                 135                 140

Gly Met Asn Thr Ala Thr Ile Pro Val Trp Gln Ser Glu Ile Ser Arg
145                 150                 155                 160

Pro Glu Asn Arg Gly Lys Leu Val Asn Leu Glu Gly Ser Val Ile Ala
                165                 170                 175

Ile Gly Thr Phe Val Ala Tyr Trp Ile Asp Phe Gly Leu Ser Tyr Val
            180                 185                 190

Asn Ser Ser Val Gln Trp Arg Phe Pro Val Ala Phe Gln Ile Val Phe
        195                 200                 205

Ala Ala Gly Leu Leu Gly Gly Ile Leu Phe Met Pro Glu Ser Pro Arg
    210                 215                 220

Trp Leu Leu Ala His Gly Lys Lys Glu Gln Ala His Ile Val Leu Gly
225                 230                 235                 240

Ala Leu Asn Asp Leu Asp Pro Asn Asp Asp His Val Leu Ala Glu Ser
                245                 250                 255

Thr Val Ile Thr Asp Ala Ile Asn Arg Phe Ser Arg Ser Gln Leu Gly
            260                 265                 270

Phe Lys Glu Leu Met Ser Gly Gly Lys Asn Gln His Phe Ala Arg Met
        275                 280                 285

Val Ile Gly Ser Ser Thr Gln Phe Phe Gln Gln Phe Thr Gly Cys Asn
    290                 295                 300

Ala Ala Ile Tyr Tyr Ser Thr Val Leu Phe Glu Glu Thr Ile Phe Val
305                 310                 315                 320

Gly Asp Arg Arg Leu Ser Leu Val Met Gly Gly Val Phe Ala Ser Val
                325                 330                 335

Tyr Ala Leu Ala Thr Ile Pro Ser Phe Phe Leu Val Asp Lys Leu Gly
            340                 345                 350

Arg Arg Asn Leu Phe Leu Ile Gly Ala Thr Gly Gln Ala Leu Ser Phe
        355                 360                 365

Thr Ile Thr Phe Ala Cys Leu Ile Asn Pro Thr Lys Gln Asn Ala Lys
    370                 375                 380

Gly Ala Ala Val Gly Ile Phe Leu Phe Ile Thr Phe Phe Ala Phe Thr
385                 390                 395                 400

Ile Leu Pro Leu Pro Trp Ile Tyr Pro Pro Glu Ile Asn Pro Leu Arg
                405                 410                 415

Thr Arg Thr Val Ala Ser Ala Val Ser Thr Cys Thr Asn Trp Leu Thr
            420                 425                 430

Asn Phe Ala Val Val Met Phe Thr Pro Ile Phe Ile Asn Asp Ala Gln
```

```
        435                 440                 445

Trp Gly Cys Tyr Leu Phe Phe Ala Cys Leu Asn Tyr Ala Phe Ile Pro
    450                 455                 460

Val Ile Phe Trp Phe Tyr Pro Glu Thr Ala Gly Arg Ser Leu Glu Glu
465                 470                 475                 480

Ile Asp Ile Ile Phe Ala Lys Ala Tyr Thr Asp Gly Arg Pro Pro Trp
                485                 490                 495

Arg Val Ala Ala Thr Met Pro His Leu Ser Leu Lys Glu Gln Glu Glu
            500                 505                 510

Gln Gly Met Gln Leu Gly Leu Tyr Asp Asn Glu Ala Glu Lys Gln Lys
        515                 520                 525

Phe Glu Gln Thr Glu Asn Leu Met Ser Ser Ser Ser Ser Ala Lys Leu
    530                 535                 540

Pro Glu Glu Gly Ser Asn Val Asn Glu Asn Glu Asn Glu Asn Thr Asn
545                 550                 555                 560

Glu Lys Asp Gln Thr Pro Lys Pro Thr Asp Val
                565                 570


<210> SEQ ID NO 9
<211> LENGTH: 440
<212> TYPE: PRT
<213> ORGANISM: Catonella morbi

<400> SEQUENCE: 9

Met Ser Glu Leu Phe Gln Asn Ile Pro Lys Ile Lys Tyr Glu Gly Ala
1               5                   10                  15

Asn Ser Lys Asn Pro Leu Ala Phe His Tyr Tyr Asp Ala Glu Lys Ile
            20                  25                  30

Val Leu Gly Lys Thr Met Lys Glu His Leu Pro Phe Ala Met Ala Trp
        35                  40                  45

Trp His Asn Leu Cys Ala Ala Gly Thr Asp Met Phe Gly Arg Asp Thr
    50                  55                  60

Ala Asp Lys Ser Phe Gly Leu Glu Lys Gly Ser Met Glu His Ala Lys
65                  70                  75                  80

Ala Lys Val Asp Ala Gly Phe Glu Phe Met Glu Lys Leu Gly Ile Lys
                85                  90                  95

Tyr Phe Cys Phe His Asp Val Asp Leu Val Pro Glu Ala Cys Asp Ile
            100                 105                 110

Lys Glu Thr Asn Ser Arg Leu Asp Glu Ile Ser Asp Tyr Ile Leu Glu
        115                 120                 125

Lys Met Lys Gly Thr Asp Ile Lys Cys Leu Trp Gly Thr Ala Asn Met
    130                 135                 140

Phe Ser Asn Pro Arg Phe Val Asn Gly Ala Gly Ser Thr Asn Ser Ala
145                 150                 155                 160

Asp Val Tyr Cys Phe Ala Ala Ala Gln Ile Lys Lys Ala Leu Asp Ile
                165                 170                 175

Thr Val Lys Leu Gly Gly Arg Gly Tyr Val Phe Trp Gly Gly Arg Glu
            180                 185                 190

Gly Tyr Glu Thr Leu Leu Asn Thr Asp Val Lys Phe Glu Gln Glu Asn
        195                 200                 205

Ile Ala Asn Leu Met Lys Met Ala Val Glu Tyr Gly Arg Ser Ile Gly
    210                 215                 220

Phe Lys Gly Asp Phe Tyr Ile Glu Pro Lys Pro Lys Glu Pro Met Lys
225                 230                 235                 240
```

```
His Gln Tyr Asp Phe Asp Ala Ala Thr Ala Ile Gly Phe Leu Arg Gln
                245                 250                 255

Tyr Gly Leu Asp Lys Asp Phe Lys Leu Asn Ile Glu Ala Asn His Ala
            260                 265                 270

Thr Leu Ala Gly His Ser Phe Gln His Glu Leu Arg Ile Ser Ser Ile
        275                 280                 285

Asn Gly Met Leu Gly Ser Val Asp Ala Asn Gln Gly Asp Met Leu Leu
    290                 295                 300

Gly Trp Asp Thr Asp Glu Phe Pro Phe Asp Val Tyr Asp Thr Thr Met
305                 310                 315                 320

Cys Met Tyr Glu Val Leu Lys Asn Gly Gly Leu Thr Gly Gly Phe Asn
                325                 330                 335

Phe Asp Ala Lys Asn Arg Arg Pro Ser Tyr Thr Tyr Glu Asp Met Phe
            340                 345                 350

Tyr Gly Phe Ile Leu Gly Met Asp Ser Phe Ala Leu Gly Leu Ile Lys
        355                 360                 365

Ala Ala Lys Leu Ile Glu Glu Gly Thr Leu Asp Asn Phe Ile Lys Glu
    370                 375                 380

Arg Tyr Lys Ser Phe Glu Ser Glu Ile Gly Lys Lys Ile Arg Ser Lys
385                 390                 395                 400

Ser Ala Ser Leu Gln Glu Leu Ala Ala Tyr Ala Glu Glu Met Gly Ala
                405                 410                 415

Pro Ala Met Pro Gly Ser Gly Arg Gln Glu Tyr Leu Gln Ala Ala Leu
            420                 425                 430

Asn Gln Asn Leu Phe Gly Glu Val
        435                 440


<210> SEQ ID NO 10
<211> LENGTH: 509
<212> TYPE: PRT
<213> ORGANISM: Bacteroides thetaiotaomicron

<400> SEQUENCE: 10

Met Asn Asn Val Phe Asp Gln Tyr Glu Val Trp Phe Val Thr Gly Ala
1               5                   10                  15

Gln Leu Leu Tyr Gly Gly Asp Ala Val Ile Ala Val Asp Ala His Ser
            20                  25                  30

Asn Glu Met Val Asn Gly Leu Asn Glu Ser Gly Lys Leu Pro Val Lys
        35                  40                  45

Val Val Tyr Lys Gly Thr Ala Asn Ser Ser Lys Glu Val Glu Ala Val
    50                  55                  60

Phe Lys Ala Ala Asn Asn Asp Asp Lys Cys Val Gly Val Ile Thr Trp
65                  70                  75                  80

Met His Thr Phe Ser Pro Ala Lys Met Trp Ile His Gly Leu Gln Gln
                85                  90                  95

Leu Lys Lys Pro Leu Leu His Leu His Thr Gln Phe Asn Lys Glu Ile
            100                 105                 110

Pro Trp Asp Thr Met Asp Met Asp Phe Met Asn Leu Asn Gln Ser Ala
        115                 120                 125

His Gly Asp Arg Glu Phe Gly His Ile Cys Thr Arg Met Arg Ile Arg
    130                 135                 140

Arg Lys Val Val Val Gly Tyr Trp Lys Glu Glu Glu Thr Leu His Lys
145                 150                 155                 160

Ile Ala Val Trp Met Arg Val Cys Ala Gly Trp Ala Asp Ser Gln Asp
                165                 170                 175
```

```
Met Leu Ile Ile Arg Phe Gly Asp Gln Met Asn Asn Val Ala Val Thr
            180                 185                 190

Asp Gly Asp Lys Val Glu Ala Glu Gln Arg Met Gly Tyr His Val Asp
        195                 200                 205

Tyr Cys Pro Ala Ser Glu Leu Met Glu Tyr His Lys Asp Ile Lys Asn
    210                 215                 220

Ala Asp Val Asp Ala Leu Val Ala Thr Tyr Phe Asn Asp Tyr Asp His
225                 230                 235                 240

Asp Ala Ser Leu Glu Asp Lys Ser Thr Glu Ala Tyr Gln Lys Val Trp
                245                 250                 255

Asn Ala Ala Lys Ala Glu Leu Ala Leu Arg Ala Ile Leu Lys Ala Lys
            260                 265                 270

Gly Ala Lys Gly Phe Thr Thr Asn Phe Asp Asp Leu Gly Gln Thr Asp
        275                 280                 285

Gly Ser Tyr Phe Asp Gln Ile Pro Gly Leu Ala Ser Gln Arg Leu Met
    290                 295                 300

Ala Glu Gly Tyr Gly Phe Gly Ala Glu Gly Asp Trp Lys Ser Ala Ala
305                 310                 315                 320

Leu Tyr Arg Thr Val Trp Val Met Asn Gln Gly Leu Pro Lys Gly Cys
                325                 330                 335

Ser Phe Leu Glu Asp Tyr Thr Leu Asn Phe Asp Gly Ala Asn Ser Ser
            340                 345                 350

Ile Leu Gln Ser His Met Leu Glu Ile Cys Pro Leu Ile Ala Ala Asn
        355                 360                 365

Lys Pro Arg Leu Glu Val His Phe Leu Gly Ile Gly Ile Arg Lys Ser
    370                 375                 380

Gln Thr Ala Arg Leu Val Phe Thr Ser Lys Thr Gly Thr Gly Cys Thr
385                 390                 395                 400

Ala Thr Val Val Asp Met Gly Asn Arg Phe Arg Leu Ile Val Asn Asp
                405                 410                 415

Val Glu Cys Ile Glu Pro Lys Pro Leu Pro Lys Leu Pro Val Ala Ser
            420                 425                 430

Ala Leu Trp Ile Pro Met Pro Asn Leu Glu Val Gly Ala Gly Ala Trp
        435                 440                 445

Ile Leu Ala Gly Gly Thr His His Ser Cys Phe Ser Tyr Asp Leu Thr
    450                 455                 460

Ala Glu Tyr Trp Glu Asp Tyr Ala Glu Ile Ala Gly Ile Glu Met Val
465                 470                 475                 480

His Ile Asn Lys Asp Thr Thr Ile Ser Cys Phe Lys Lys Glu Leu Arg
                485                 490                 495

Met Asn Glu Val Tyr Tyr Met Leu Asn Lys Ala Leu Cys
            500                 505
```

<210> SEQ ID NO 11
<211> LENGTH: 531
<212> TYPE: PRT
<213> ORGANISM: Bacteroides thetaiotaomicron

<400> SEQUENCE: 11

```
Met Lys Leu Asp Ala Lys Ser Thr Ile Glu Thr Gly Lys Ala Ile Leu
1               5                   10                  15

Gly Ile Glu Leu Gly Ser Thr Arg Ile Lys Ala Val Leu Ile Asp Gln
            20                  25                  30

Glu Asn Lys Pro Ile Ala Gln Gly Ser His Thr Trp Glu Asn Gln Leu
```

-continued

```
        35                  40                  45

Val Asn Gly Leu Trp Thr Tyr Ser Ile Asp Ala Ile Trp Ser Gly Leu
    50                  55                  60

Gln Asp Cys Tyr Ala Asp Leu Arg Ser Asn Val Lys Lys Leu Tyr Asp
65                  70                  75                  80

Thr Glu Ile Glu Thr Leu Ala Ala Ile Gly Val Ser Ala Met Met His
                85                  90                  95

Gly Tyr Met Pro Phe Asn Glu Lys Glu Glu Ile Leu Val Pro Phe Arg
            100                 105                 110

Thr Trp Arg Asn Thr Asn Thr Gly Arg Ala Ala Ala Glu Leu Ser Glu
        115                 120                 125

Leu Phe Val Tyr Asn Ile Pro Leu Arg Trp Ser Ile Ser His Leu Tyr
    130                 135                 140

Gln Ala Ile Leu Asp Asn Glu Ala His Val Lys Asp Ile Lys Phe Leu
145                 150                 155                 160

Thr Thr Leu Ala Gly Tyr Val His Trp Gln Ile Thr Gly Glu Lys Val
                165                 170                 175

Leu Gly Ile Gly Asp Ala Ser Gly Met Leu Pro Ile Asp Pro Thr Thr
            180                 185                 190

Asn Asn Tyr Ser Ala Glu Met Val Ala Lys Phe Asn Asn Leu Ile Ala
        195                 200                 205

Ser Lys Glu Tyr Ser Trp Lys Leu Glu Asp Ile Leu Pro Lys Val Leu
    210                 215                 220

Ser Ala Gly Glu Asn Ala Gly Val Leu Thr Pro Glu Gly Cys Lys Lys
225                 230                 235                 240

Leu Asp Ala Ser Gly His Leu Lys Ala Gly Ile Pro Val Cys Pro Pro
                245                 250                 255

Glu Gly Asp Ala Gly Thr Gly Met Val Ala Thr Asn Ala Val Lys Gln
            260                 265                 270

Arg Thr Gly Asn Val Ser Ala Gly Thr Ser Ser Phe Ser Met Ile Val
        275                 280                 285

Leu Glu Lys Glu Leu Ser Lys Pro Tyr Glu Met Ile Asp Met Val Thr
    290                 295                 300

Thr Pro Asp Gly Ser Leu Val Ala Met Val His Cys Asn Asn Cys Thr
305                 310                 315                 320

Ser Asp Leu Asn Ala Trp Val Asn Leu Phe Lys Glu Tyr Gln Glu Leu
                325                 330                 335

Leu Gly Ile Pro Val Asp Met Asp Glu Leu Tyr Gly Lys Leu Tyr Asn
            340                 345                 350

Ile Ala Leu Thr Gly Asp Thr Asp Cys Gly Gly Leu Leu Ser Tyr Asn
        355                 360                 365

Tyr Ile Ser Gly Glu Pro Val Thr Gly Leu Ala Glu Gly Arg Pro Leu
    370                 375                 380

Phe Val Arg Ser Ala Asn Asp Lys Phe Asn Leu Ala Asn Phe Met Arg
385                 390                 395                 400

Ala His Leu Tyr Ala Ser Val Gly Val Leu Lys Ile Gly Asn Asp Ile
                405                 410                 415

Leu Phe Asn Glu Glu Lys Ile Lys Val Asp Arg Ile Thr Gly His Gly
            420                 425                 430

Gly Leu Phe Arg Thr Lys Gly Val Gly Gln Arg Val Leu Ala Ala Ala
        435                 440                 445

Ile Asn Ser Pro Ile Ser Val Met Glu Thr Ala Gly Glu Gly Gly Ala
    450                 455                 460
```

```
Trp Gly Ile Ala Leu Leu Gly Ser Tyr Leu Val Asn Asn Lys Lys Gly
465                 470                 475                 480

Gln Ser Leu Ala Asp Phe Leu Asp Glu Ser Val Phe Val Ser Asp Ala
                485                 490                 495

Gly Val Glu Val Ser Pro Thr Pro Glu Asp Val Ala Gly Phe Asn Thr
            500                 505                 510

Tyr Ile Glu Ser Tyr Lys Ala Gly Leu Pro Ile Glu Glu Ala Ala Val
        515                 520                 525

Lys Phe Lys
    530


<210> SEQ ID NO 12
<211> LENGTH: 227
<212> TYPE: PRT
<213> ORGANISM: Bacteroides thetaiotaomicron

<400> SEQUENCE: 12

Met Leu Glu Glu Leu Lys Glu Lys Val Phe His Ala Asn Leu Glu Leu
1               5                   10                  15

Val Lys His Gly Leu Val Ile Phe Thr Trp Gly Asn Val Ser Ala Ile
            20                  25                  30

Asp Arg Glu Thr Glu Leu Val Val Ile Lys Pro Ser Gly Val Ser Tyr
        35                  40                  45

Asp Asp Met Lys Ala Glu Asp Met Val Val Val Asp Leu Asp Gly Lys
    50                  55                  60

Val Val Glu Gly Arg Leu Lys Pro Ser Ser Asp Thr Pro Thr His Val
65                  70                  75                  80

Val Leu Tyr Lys Ala Phe Pro Glu Ile Gly Gly Val Val His Thr His
                85                  90                  95

Ser Thr Tyr Ala Thr Ala Trp Ala Gln Ala Gly Cys Asp Ile Pro Asn
            100                 105                 110

Ile Gly Thr Thr His Ala Asp Tyr Phe His Asp Ala Ile Pro Cys Thr
        115                 120                 125

Ala Asp Met Thr Glu Ala Glu Val Lys Gly Ala Tyr Glu Leu Glu Thr
    130                 135                 140

Gly Asn Val Ile Val Lys Arg Phe Glu Gly Leu Asn Pro Val His Thr
145                 150                 155                 160

Pro Gly Val Leu Val Lys Asn His Gly Pro Phe Ser Trp Gly Lys Asp
                165                 170                 175

Ala His Asp Ala Val His Asn Ala Val Val Met Glu Gln Val Ala Lys
            180                 185                 190

Met Ala Ser Ile Ala Tyr Ala Val Asn Pro Asn Leu Thr Met Asn Pro
        195                 200                 205

Leu Leu Val Glu Lys His Phe Ser Arg Lys His Gly Pro Asn Ala Tyr
    210                 215                 220

Tyr Gly Gln
225


<210> SEQ ID NO 13
<211> LENGTH: 489
<212> TYPE: PRT
<213> ORGANISM: Saccharomyces cerevisiae

<400> SEQUENCE: 13

Met Ser Ala Asp Phe Gly Leu Ile Gly Leu Ala Val Met Gly Gln Asn
1               5                   10                  15
```

```
Leu Ile Leu Asn Ala Ala Asp His Gly Phe Thr Val Cys Ala Tyr Asn
            20                  25                  30

Arg Thr Gln Ser Lys Val Asp His Phe Leu Ala Asn Glu Ala Lys Gly
        35                  40                  45

Lys Ser Ile Ile Gly Ala Thr Ser Ile Glu Asp Phe Ile Ser Lys Leu
    50                  55                  60

Lys Arg Pro Arg Lys Val Met Leu Leu Val Lys Ala Gly Ala Pro Val
65                  70                  75                  80

Asp Ala Leu Ile Asn Gln Ile Val Pro Leu Leu Glu Lys Gly Asp Ile
                85                  90                  95

Ile Ile Asp Gly Gly Asn Ser His Phe Pro Asp Ser Asn Arg Arg Tyr
            100                 105                 110

Glu Glu Leu Lys Lys Lys Gly Ile Leu Phe Val Gly Ser Gly Val Ser
        115                 120                 125

Gly Gly Glu Glu Gly Ala Arg Tyr Gly Pro Ser Leu Met Pro Gly Gly
    130                 135                 140

Ser Glu Glu Ala Trp Pro His Ile Lys Asn Ile Phe Gln Ser Ile Ser
145                 150                 155                 160

Ala Lys Ser Asp Gly Glu Pro Cys Cys Glu Trp Val Gly Pro Ala Gly
                165                 170                 175

Ala Gly His Tyr Val Lys Met Val His Asn Gly Ile Glu Tyr Gly Asp
            180                 185                 190

Met Gln Leu Ile Cys Glu Ala Tyr Asp Ile Met Lys Arg Leu Gly Gly
        195                 200                 205

Phe Thr Asp Lys Glu Ile Ser Asp Val Phe Ala Lys Trp Asn Asn Gly
    210                 215                 220

Val Leu Asp Ser Phe Leu Val Glu Ile Thr Arg Asp Ile Leu Lys Phe
225                 230                 235                 240

Asp Asp Val Asp Gly Lys Pro Leu Val Glu Lys Ile Met Asp Thr Ala
                245                 250                 255

Gly Gln Lys Gly Thr Gly Lys Trp Thr Ala Ile Asn Ala Leu Asp Leu
            260                 265                 270

Gly Met Pro Val Thr Leu Ile Gly Glu Ala Val Phe Ala Arg Cys Leu
        275                 280                 285

Ser Ala Leu Lys Asn Glu Arg Ile Arg Ala Ser Lys Val Leu Pro Gly
    290                 295                 300

Pro Glu Val Pro Lys Asp Ala Val Lys Asp Arg Glu Gln Phe Val Asp
305                 310                 315                 320

Asp Leu Glu Gln Ala Leu Tyr Ala Ser Lys Ile Ile Ser Tyr Ala Gln
                325                 330                 335

Gly Phe Met Leu Ile Arg Glu Ala Ala Ala Thr Tyr Gly Trp Lys Leu
            340                 345                 350

Asn Asn Pro Ala Ile Ala Leu Met Trp Arg Gly Gly Cys Ile Ile Arg
        355                 360                 365

Ser Val Phe Leu Gly Gln Ile Thr Lys Ala Tyr Arg Glu Glu Pro Asp
    370                 375                 380

Leu Glu Asn Leu Leu Phe Asn Lys Phe Phe Ala Asp Ala Val Thr Lys
385                 390                 395                 400

Ala Gln Ser Gly Trp Arg Lys Ser Ile Ala Leu Ala Thr Thr Tyr Gly
                405                 410                 415

Ile Pro Thr Pro Ala Phe Ser Thr Ala Leu Ser Phe Tyr Asp Gly Tyr
            420                 425                 430
```

```
Arg Ser Glu Arg Leu Pro Ala Asn Leu Leu Gln Ala Gln Arg Asp Tyr
        435                 440                 445

Phe Gly Ala His Thr Phe Arg Val Leu Pro Glu Cys Ala Ser Asp Asn
    450                 455                 460

Leu Pro Val Asp Lys Asp Ile His Ile Asn Trp Thr Gly His Gly Gly
465                 470                 475                 480

Asn Val Ser Ser Ser Thr Tyr Gln Ala
                485


<210> SEQ ID NO 14
<211> LENGTH: 258
<212> TYPE: PRT
<213> ORGANISM: Saccharomyces cerevisiae

<400> SEQUENCE: 14

Met Ala Ala Gly Val Pro Lys Ile Asp Ala Leu Glu Ser Leu Gly Asn
1               5                   10                  15

Pro Leu Glu Asp Ala Lys Arg Ala Ala Ala Tyr Arg Ala Val Asp Glu
            20                  25                  30

Asn Leu Lys Phe Asp Asp His Lys Ile Ile Gly Ile Gly Ser Gly Ser
        35                  40                  45

Thr Val Val Tyr Val Ala Glu Arg Ile Gly Gln Tyr Leu His Asp Pro
    50                  55                  60

Lys Phe Tyr Glu Val Ala Ser Lys Phe Ile Cys Ile Pro Thr Gly Phe
65                  70                  75                  80

Gln Ser Arg Asn Leu Ile Leu Asp Asn Lys Leu Gln Leu Gly Ser Ile
                85                  90                  95

Glu Gln Tyr Pro Arg Ile Asp Ile Ala Phe Asp Gly Ala Asp Glu Val
            100                 105                 110

Asp Glu Asn Leu Gln Leu Ile Lys Gly Gly Gly Ala Cys Leu Phe Gln
        115                 120                 125

Glu Lys Leu Val Ser Thr Ser Ala Lys Thr Phe Ile Val Val Ala Asp
    130                 135                 140

Ser Arg Lys Lys Ser Pro Lys His Leu Gly Lys Asn Trp Arg Gln Gly
145                 150                 155                 160

Val Pro Ile Glu Ile Val Pro Ser Ser Tyr Val Arg Val Lys Asn Asp
                165                 170                 175

Leu Leu Glu Gln Leu His Ala Glu Lys Val Asp Ile Arg Gln Gly Gly
            180                 185                 190

Ser Ala Lys Ala Gly Pro Val Val Thr Asp Asn Asn Asn Phe Ile Ile
        195                 200                 205

Asp Ala Asp Phe Gly Glu Ile Ser Asp Pro Arg Lys Leu His Arg Glu
    210                 215                 220

Ile Lys Leu Leu Val Gly Val Val Glu Thr Gly Leu Phe Ile Asp Asn
225                 230                 235                 240

Ala Ser Lys Ala Tyr Phe Gly Asn Ser Asp Gly Ser Val Glu Val Thr
                245                 250                 255

Glu Lys


<210> SEQ ID NO 15
<211> LENGTH: 238
<212> TYPE: PRT
<213> ORGANISM: Saccharomyces cerevisiae

<400> SEQUENCE: 15

Met Val Lys Pro Ile Ile Ala Pro Ser Ile Leu Ala Ser Asp Phe Ala
```

```
1               5                   10                  15

Asn Leu Gly Cys Glu Cys His Lys Val Ile Asn Ala Gly Ala Asp Trp
            20                  25                  30

Leu His Ile Asp Val Met Asp Gly His Phe Val Pro Asn Ile Thr Leu
        35                  40                  45

Gly Gln Pro Ile Val Thr Ser Leu Arg Arg Ser Val Pro Arg Pro Gly
    50                  55                  60

Asp Ala Ser Asn Thr Glu Lys Lys Pro Thr Ala Phe Phe Asp Cys His
65                  70                  75                  80

Met Met Val Glu Asn Pro Glu Lys Trp Val Asp Asp Phe Ala Lys Cys
                85                  90                  95

Gly Ala Asp Gln Phe Thr Phe His Tyr Glu Ala Thr Gln Asp Pro Leu
            100                 105                 110

His Leu Val Lys Leu Ile Lys Ser Lys Gly Ile Lys Ala Ala Cys Ala
        115                 120                 125

Ile Lys Pro Gly Thr Ser Val Asp Val Leu Phe Glu Leu Ala Pro His
    130                 135                 140

Leu Asp Met Ala Leu Val Met Thr Val Glu Pro Gly Phe Gly Gly Gln
145                 150                 155                 160

Lys Phe Met Glu Asp Met Met Pro Lys Val Glu Thr Leu Arg Ala Lys
                165                 170                 175

Phe Pro His Leu Asn Ile Gln Val Asp Gly Gly Leu Gly Lys Glu Thr
            180                 185                 190

Ile Pro Lys Ala Ala Lys Ala Gly Ala Asn Val Ile Val Ala Gly Thr
        195                 200                 205

Ser Val Phe Thr Ala Ala Asp Pro His Asp Val Ile Ser Phe Met Lys
    210                 215                 220

Glu Glu Val Ser Lys Glu Leu Arg Ser Arg Asp Leu Leu Asp
225                 230                 235


<210> SEQ ID NO 16
<211> LENGTH: 249
<212> TYPE: PRT
<213> ORGANISM: Saccharomyces cerevisiae

<400> SEQUENCE: 16

Met Val Thr Val Gly Val Phe Ser Glu Arg Ala Ser Leu Thr His Gln
1               5                   10                  15

Leu Gly Glu Phe Ile Val Lys Lys Gln Asp Glu Ala Leu Gln Lys Lys
            20                  25                  30

Ser Asp Phe Lys Val Ser Val Ser Gly Gly Ser Leu Ile Asp Ala Leu
        35                  40                  45

Tyr Glu Ser Leu Val Ala Asp Glu Ser Leu Ser Ser Arg Val Gln Trp
    50                  55                  60

Ser Lys Trp Gln Ile Tyr Phe Ser Asp Glu Arg Ile Val Pro Leu Thr
65                  70                  75                  80

Asp Ala Asp Ser Asn Tyr Gly Ala Phe Lys Arg Ala Val Leu Asp Lys
                85                  90                  95

Leu Pro Ser Thr Ser Gln Pro Asn Val Tyr Pro Met Asp Glu Ser Leu
            100                 105                 110

Ile Gly Ser Asp Ala Glu Ser Asn Asn Lys Ile Ala Ala Glu Tyr Glu
        115                 120                 125

His Ile Val Pro Gln Val Leu Asp Leu Val Leu Leu Gly Cys Gly Pro
    130                 135                 140
```

```
Asp Gly His Thr Cys Ser Leu Phe Pro Gly Glu Thr His Arg Tyr Leu
145                 150                 155                 160

Leu Asn Glu Thr Thr Lys Arg Val Ala Trp Cys His Asp Ser Pro Lys
                165                 170                 175

Pro Pro Ser Asp Arg Ile Thr Phe Thr Leu Pro Val Leu Lys Asp Ala
            180                 185                 190

Lys Ala Leu Cys Phe Val Ala Glu Gly Ser Ser Lys Gln Asn Ile Met
        195                 200                 205

His Glu Ile Phe Asp Leu Lys Asn Asp Gln Leu Pro Thr Ala Leu Val
    210                 215                 220

Asn Lys Leu Phe Gly Glu Lys Thr Ser Trp Phe Val Asn Glu Glu Ala
225                 230                 235                 240

Phe Gly Lys Val Gln Thr Lys Thr Phe
                245
```

<210> SEQ ID NO 17
<211> LENGTH: 335
<212> TYPE: PRT
<213> ORGANISM: Saccharomyces cerevisiae

<400> SEQUENCE: 17

```
Met Ser Glu Pro Ala Gln Lys Lys Gln Lys Val Ala Asn Asn Ser Leu
1               5                   10                  15

Glu Gln Leu Lys Ala Ser Gly Thr Val Val Val Ala Asp Thr Gly Asp
            20                  25                  30

Phe Gly Ser Ile Ala Lys Phe Gln Pro Gln Asp Ser Thr Thr Asn Pro
        35                  40                  45

Ser Leu Ile Leu Ala Ala Ala Lys Gln Pro Thr Tyr Ala Lys Leu Ile
    50                  55                  60

Asp Val Ala Val Glu Tyr Gly Lys Lys His Gly Lys Thr Thr Glu Glu
65                  70                  75                  80

Gln Val Glu Asn Ala Val Asp Arg Leu Leu Val Glu Phe Gly Lys Glu
                85                  90                  95

Ile Leu Lys Ile Val Pro Gly Arg Val Ser Thr Glu Val Asp Ala Arg
            100                 105                 110

Leu Ser Phe Asp Thr Gln Ala Thr Ile Glu Lys Ala Arg His Ile Ile
        115                 120                 125

Lys Leu Phe Glu Gln Glu Gly Val Ser Lys Glu Arg Val Leu Ile Lys
    130                 135                 140

Ile Ala Ser Thr Trp Glu Gly Ile Gln Ala Ala Lys Glu Leu Glu Glu
145                 150                 155                 160

Lys Asp Gly Ile His Cys Asn Leu Thr Leu Leu Phe Ser Phe Val Gln
                165                 170                 175

Ala Val Ala Cys Ala Glu Ala Gln Val Thr Leu Ile Ser Pro Phe Val
            180                 185                 190

Gly Arg Ile Leu Asp Trp Tyr Lys Ser Ser Thr Gly Lys Asp Tyr Lys
        195                 200                 205

Gly Glu Ala Asp Pro Gly Val Ile Ser Val Lys Lys Ile Tyr Asn Tyr
    210                 215                 220

Tyr Lys Lys Tyr Gly Tyr Lys Thr Ile Val Met Gly Ala Ser Phe Arg
225                 230                 235                 240

Ser Thr Asp Glu Ile Lys Asn Leu Ala Gly Val Asp Tyr Leu Thr Ile
                245                 250                 255

Ser Pro Ala Leu Leu Asp Lys Leu Met Asn Ser Thr Glu Pro Phe Pro
            260                 265                 270
```

```
Arg Val Leu Asp Pro Val Ser Ala Lys Lys Glu Ala Gly Asp Lys Ile
        275                 280                 285

Ser Tyr Ile Ser Asp Glu Ser Lys Phe Arg Phe Asp Leu Asn Glu Asp
    290                 295                 300

Ala Met Ala Thr Glu Lys Leu Ser Glu Gly Ile Arg Lys Phe Ser Ala
305                 310                 315                 320

Asp Ile Val Thr Leu Phe Asp Leu Ile Glu Lys Lys Val Thr Ala
                325                 330                 335


<210> SEQ ID NO 18
<211> LENGTH: 680
<212> TYPE: PRT
<213> ORGANISM: Saccharomyces cerevisiae

<400> SEQUENCE: 18

Met Thr Gln Phe Thr Asp Ile Asp Lys Leu Ala Val Ser Thr Ile Arg
1               5                   10                  15

Ile Leu Ala Val Asp Thr Val Ser Lys Ala Asn Ser Gly His Pro Gly
            20                  25                  30

Ala Pro Leu Gly Met Ala Pro Ala Ala His Val Leu Trp Ser Gln Met
        35                  40                  45

Arg Met Asn Pro Thr Asn Pro Asp Trp Ile Asn Arg Asp Arg Phe Val
    50                  55                  60

Leu Ser Asn Gly His Ala Val Ala Leu Leu Tyr Ser Met Leu His Leu
65                  70                  75                  80

Thr Gly Tyr Asp Leu Ser Ile Glu Asp Leu Lys Gln Phe Arg Gln Leu
                85                  90                  95

Gly Ser Arg Thr Pro Gly His Pro Glu Phe Glu Leu Pro Gly Val Glu
            100                 105                 110

Val Thr Thr Gly Pro Leu Gly Gln Gly Ile Ser Asn Ala Val Gly Met
        115                 120                 125

Ala Met Ala Gln Ala Asn Leu Ala Ala Thr Tyr Asn Lys Pro Gly Phe
    130                 135                 140

Thr Leu Ser Asp Asn Tyr Thr Tyr Val Phe Leu Gly Asp Gly Cys Leu
145                 150                 155                 160

Gln Glu Gly Ile Ser Ser Glu Ala Ser Ser Leu Ala Gly His Leu Lys
                165                 170                 175

Leu Gly Asn Leu Ile Ala Ile Tyr Asp Asp Asn Lys Ile Thr Ile Asp
            180                 185                 190

Gly Ala Thr Ser Ile Ser Phe Asp Glu Asp Val Ala Lys Arg Tyr Glu
        195                 200                 205

Ala Tyr Gly Trp Glu Val Leu Tyr Val Glu Asn Gly Asn Glu Asp Leu
    210                 215                 220

Ala Gly Ile Ala Lys Ala Ile Ala Gln Ala Lys Leu Ser Lys Asp Lys
225                 230                 235                 240

Pro Thr Leu Ile Lys Met Thr Thr Thr Ile Gly Tyr Gly Ser Leu His
                245                 250                 255

Ala Gly Ser His Ser Val His Gly Ala Pro Leu Lys Ala Asp Asp Val
            260                 265                 270

Lys Gln Leu Lys Ser Lys Phe Gly Phe Asn Gln Asp Lys Ser Phe Val
        275                 280                 285

Val Pro Gln Glu Val Tyr Asp His Tyr Gln Lys Thr Ile Leu Lys Pro
    290                 295                 300

Gly Val Glu Ala Asn Asn Lys Trp Asn Lys Leu Phe Ser Glu Tyr Gln
```

```
305                 310                 315                 320

Lys Lys Phe Pro Glu Leu Gly Ala Glu Leu Ala Arg Arg Leu Ser Gly
                325                 330                 335

Gln Leu Pro Ala Asn Trp Glu Ser Lys Leu Pro Thr Tyr Thr Ala Lys
            340                 345                 350

Asp Ser Ala Val Ala Thr Arg Lys Leu Ser Glu Thr Val Leu Glu Asp
        355                 360                 365

Val Tyr Asn Gln Leu Pro Glu Leu Ile Gly Gly Ser Ala Asp Leu Thr
    370                 375                 380

Pro Ser Asn Leu Thr Arg Trp Lys Glu Ala Leu Asp Phe Gln Pro Pro
385                 390                 395                 400

Ser Ser Gly Ser Gly Asn Tyr Ser Gly Arg Tyr Ile Arg Tyr Gly Ile
                405                 410                 415

Arg Glu His Ala Met Gly Ala Ile Met Asn Gly Ile Ser Ala Phe Gly
            420                 425                 430

Ala Asn Tyr Lys Pro Tyr Gly Gly Thr Phe Leu Asn Phe Val Ser Tyr
        435                 440                 445

Ala Ala Gly Ala Val Arg Leu Ser Ala Leu Ser Gly His Pro Val Ile
    450                 455                 460

Trp Val Ala Thr His Asp Ser Ile Gly Val Gly Glu Asp Gly Pro Thr
465                 470                 475                 480

His Gln Pro Ile Glu Thr Leu Ala His Phe Arg Ser Leu Pro Asn Ile
                485                 490                 495

Gln Val Trp Arg Pro Ala Asp Gly Asn Glu Val Ser Ala Ala Tyr Lys
            500                 505                 510

Asn Ser Leu Glu Ser Lys His Thr Pro Ser Ile Ile Ala Leu Ser Arg
        515                 520                 525

Gln Asn Leu Pro Gln Leu Glu Gly Ser Ser Ile Glu Ser Ala Ser Lys
    530                 535                 540

Gly Gly Tyr Val Leu Gln Asp Val Ala Asn Pro Asp Ile Ile Leu Val
545                 550                 555                 560

Ala Thr Gly Ser Glu Val Ser Leu Ser Val Glu Ala Ala Lys Thr Leu
                565                 570                 575

Ala Ala Lys Asn Ile Lys Ala Arg Val Val Ser Leu Pro Asp Phe Phe
            580                 585                 590

Thr Phe Asp Lys Gln Pro Leu Glu Tyr Arg Leu Ser Val Leu Pro Asp
        595                 600                 605

Asn Val Pro Ile Met Ser Val Glu Val Leu Ala Thr Thr Cys Trp Gly
    610                 615                 620

Lys Tyr Ala His Gln Ser Phe Gly Ile Asp Arg Phe Gly Ala Ser Gly
625                 630                 635                 640

Lys Ala Pro Glu Val Phe Lys Phe Phe Gly Phe Thr Pro Glu Gly Val
                645                 650                 655

Ala Glu Arg Ala Gln Lys Thr Ile Ala Phe Tyr Lys Gly Asp Lys Leu
            660                 665                 670

Ile Ser Pro Leu Lys Lys Ala Phe
        675                 680


<210> SEQ ID NO 19
<211> LENGTH: 600
<212> TYPE: PRT
<213> ORGANISM: Saccharomyces cerevisiae

<400> SEQUENCE: 19
```

```
Met Leu Cys Ser Val Ile Gln Arg Gln Thr Arg Glu Val Ser Asn Thr
1               5                   10                  15

Met Ser Leu Asp Ser Tyr Tyr Leu Gly Phe Asp Leu Ser Thr Gln Gln
            20                  25                  30

Leu Lys Cys Leu Ala Ile Asn Gln Asp Leu Lys Ile Val His Ser Glu
        35                  40                  45

Thr Val Glu Phe Glu Lys Asp Leu Pro His Tyr Asn Thr Lys Lys Gly
    50                  55                  60

Val Tyr Ile His Gly Asp Ala Ile Glu Cys Pro Val Ala Met Trp Leu
65                  70                  75                  80

Glu Ala Leu Asp Leu Val Leu Ser Lys Tyr Arg Glu Ala Lys Phe Pro
                85                  90                  95

Leu Asn Lys Val Met Ala Val Ser Gly Ser Cys Gln Gln His Gly Ser
            100                 105                 110

Val Tyr Trp Ser Ser Gln Ala Glu Ser Leu Leu Glu Gln Leu Asn Lys
        115                 120                 125

Lys Pro Glu Lys Asp Leu Leu His Tyr Val Ser Ser Val Ala Phe Ala
    130                 135                 140

Arg Gln Thr Ala Pro Asn Trp Gln Asp His Ser Thr Ala Lys Gln Cys
145                 150                 155                 160

Gln Glu Phe Glu Glu Cys Ile Gly Gly Pro Glu Lys Met Ala Gln Leu
                165                 170                 175

Thr Gly Ser Arg Ala His Phe Arg Phe Thr Gly Pro Gln Ile Leu Lys
            180                 185                 190

Ile Ala Gln Leu Glu Pro Glu Ala Tyr Glu Lys Thr Lys Thr Ile Ser
        195                 200                 205

Leu Val Ser Asn Phe Leu Thr Ser Ile Leu Met Gly His Leu Val Glu
    210                 215                 220

Leu Glu Glu Ala Asp Ala Cys Gly Met Asn Leu Tyr Asp Ile Arg Glu
225                 230                 235                 240

Arg Lys Phe Ser Asp Glu Leu Leu His Leu Ile Asp Ser Ser Ser Lys
                245                 250                 255

Asp Lys Thr Ile Arg Gln Lys Leu Met Arg Ala Pro Met Lys Asn Leu
            260                 265                 270

Ile Ala Gly Thr Ile Cys Lys Tyr Phe Ile Glu Lys Tyr Gly Phe Asn
        275                 280                 285

Thr Asn Cys Lys Val Ser Pro Met Thr Gly Asp Asn Leu Ala Thr Ile
    290                 295                 300

Cys Ser Leu Pro Leu Arg Lys Asn Asp Val Leu Val Ser Leu Gly Thr
305                 310                 315                 320

Ser Thr Thr Val Leu Leu Val Thr Asp Lys Tyr His Pro Ser Pro Asn
                325                 330                 335

Tyr His Leu Phe Ile His Pro Thr Leu Pro Asn His Tyr Met Gly Met
            340                 345                 350

Ile Cys Tyr Cys Asn Gly Ser Leu Ala Arg Glu Arg Ile Arg Asp Glu
        355                 360                 365

Leu Asn Lys Glu Arg Glu Asn Asn Tyr Glu Lys Thr Asn Asp Trp Ile
    370                 375                 380

Leu Phe Asn Gln Ala Val Leu Asp Asp Ser Glu Ser Ser Glu Asn Glu
385                 390                 395                 400

Leu Gly Val Tyr Phe Pro Leu Gly Glu Ile Val Pro Ser Val Lys Ala
                405                 410                 415

Ile Asn Lys Arg Val Ile Phe Asn Pro Lys Thr Gly Met Ile Glu Arg
```

```
            420                 425                 430

Glu Val Ala Lys Phe Lys Asp Lys Arg His Asp Ala Lys Asn Ile Val
        435                 440                 445

Glu Ser Gln Ala Leu Ser Cys Arg Val Arg Ile Ser Pro Leu Leu Ser
    450                 455                 460

Asp Ser Asn Ala Ser Ser Gln Gln Arg Leu Asn Glu Asp Thr Ile Val
465                 470                 475                 480

Lys Phe Asp Tyr Asp Glu Ser Pro Leu Arg Asp Tyr Leu Asn Lys Arg
                485                 490                 495

Pro Glu Arg Thr Phe Phe Val Gly Gly Ala Ser Lys Asn Asp Ala Ile
            500                 505                 510

Val Lys Lys Phe Ala Gln Val Ile Gly Ala Thr Lys Gly Asn Phe Arg
        515                 520                 525

Leu Glu Thr Pro Asn Ser Cys Ala Leu Gly Gly Cys Tyr Lys Ala Met
    530                 535                 540

Trp Ser Leu Leu Tyr Asp Ser Asn Lys Ile Ala Val Pro Phe Asp Lys
545                 550                 555                 560

Phe Leu Asn Asp Asn Phe Pro Trp His Val Met Glu Ser Ile Ser Asp
                565                 570                 575

Val Asp Asn Glu Asn Trp Asp Arg Tyr Asn Ser Lys Ile Val Pro Leu
            580                 585                 590

Ser Glu Leu Glu Lys Thr Leu Ile
        595                 600


<210> SEQ ID NO 20
<211> LENGTH: 505
<212> TYPE: PRT
<213> ORGANISM: Saccharomyces cerevisiae

<400> SEQUENCE: 20

Met Ser Glu Gly Pro Val Lys Phe Glu Lys Asn Thr Val Ile Ser Val
1               5                   10                  15

Phe Gly Ala Ser Gly Asp Leu Ala Lys Lys Lys Thr Phe Pro Ala Leu
            20                  25                  30

Phe Gly Leu Phe Arg Glu Gly Tyr Leu Asp Pro Ser Thr Lys Ile Phe
        35                  40                  45

Gly Tyr Ala Arg Ser Lys Leu Ser Met Glu Glu Asp Leu Lys Ser Arg
    50                  55                  60

Val Leu Pro His Leu Lys Lys Pro His Gly Glu Ala Asp Asp Ser Lys
65                  70                  75                  80

Val Glu Gln Phe Phe Lys Met Val Ser Tyr Ile Ser Gly Asn Tyr Asp
                85                  90                  95

Thr Asp Glu Gly Phe Asp Glu Leu Arg Thr Gln Ile Glu Lys Phe Glu
            100                 105                 110

Lys Ser Ala Asn Val Asp Val Pro His Arg Leu Phe Tyr Leu Ala Leu
        115                 120                 125

Pro Pro Ser Val Phe Leu Thr Val Ala Lys Gln Ile Lys Ser Arg Val
    130                 135                 140

Tyr Ala Glu Asn Gly Ile Thr Arg Val Ile Val Glu Lys Pro Phe Gly
145                 150                 155                 160

His Asp Leu Ala Ser Ala Arg Glu Leu Gln Lys Asn Leu Gly Pro Leu
                165                 170                 175

Phe Lys Glu Glu Glu Leu Tyr Arg Ile Asp His Tyr Leu Gly Lys Glu
            180                 185                 190
```

-continued

```
Leu Val Lys Asn Leu Leu Val Leu Arg Phe Gly Asn Gln Phe Leu Asn
        195                 200                 205

Ala Ser Trp Asn Arg Asp Asn Ile Gln Ser Val Gln Ile Ser Phe Lys
    210                 215                 220

Glu Arg Phe Gly Thr Glu Gly Arg Gly Gly Tyr Phe Asp Ser Ile Gly
225                 230                 235                 240

Ile Ile Arg Asp Val Met Gln Asn His Leu Leu Gln Ile Met Thr Leu
                245                 250                 255

Leu Thr Met Glu Arg Pro Val Ser Phe Asp Pro Glu Ser Ile Arg Asp
            260                 265                 270

Glu Lys Val Lys Val Leu Lys Ala Val Ala Pro Ile Asp Thr Asp Asp
        275                 280                 285

Val Leu Leu Gly Gln Tyr Gly Lys Ser Glu Asp Gly Ser Lys Pro Ala
    290                 295                 300

Tyr Val Asp Asp Asp Thr Val Asp Lys Asp Ser Lys Cys Val Thr Phe
305                 310                 315                 320

Ala Ala Met Thr Phe Asn Ile Glu Asn Glu Arg Trp Glu Gly Val Pro
                325                 330                 335

Ile Met Met Arg Ala Gly Lys Ala Leu Asn Glu Ser Lys Val Glu Ile
            340                 345                 350

Arg Leu Gln Tyr Lys Ala Val Ala Ser Gly Val Phe Lys Asp Ile Pro
        355                 360                 365

Asn Asn Glu Leu Val Ile Arg Val Gln Pro Asp Ala Ala Val Tyr Leu
    370                 375                 380

Lys Phe Asn Ala Lys Thr Pro Gly Leu Ser Asn Ala Thr Gln Val Thr
385                 390                 395                 400

Asp Leu Asn Leu Thr Tyr Ala Ser Arg Tyr Gln Asp Phe Trp Ile Pro
                405                 410                 415

Glu Ala Tyr Glu Val Leu Ile Arg Asp Ala Leu Leu Gly Asp His Ser
            420                 425                 430

Asn Phe Val Arg Asp Asp Glu Leu Asp Ile Ser Trp Gly Ile Phe Thr
        435                 440                 445

Pro Leu Leu Lys His Ile Glu Arg Pro Asp Gly Pro Thr Pro Glu Ile
    450                 455                 460

Tyr Pro Tyr Gly Ser Arg Gly Pro Lys Gly Leu Lys Glu Tyr Met Gln
465                 470                 475                 480

Lys His Lys Tyr Val Met Pro Glu Lys His Pro Tyr Ala Trp Pro Val
                485                 490                 495

Thr Lys Pro Glu Asp Thr Lys Asp Asn
            500                 505
```

ACETATE TOXICITY TOLERANCE IN RECOMBINANT MICROBIAL HOST CELLS

STATEMENT REGARDING SEQUENCE LISTING

The Sequence Listing associated with this application is provided in text format in lieu of a paper copy, and is hereby incorporated by reference into the specification. The name of the text file containing the Sequence Listing is 580127_410USPC_SEQUENCE_LISTING.txt. The text file is 90.7 KB, was created on Mar. 12, 2020, and is being submitted electronically via EFS-Web.

TECHNOLOGICAL FIELD

The present disclosure concerns recombinant microbial host cells with increased tolerance towards ethanol/robustness and capable of converting acetate into ethanol as well as methods of using such recombinant microbial host cells for the production of ethanol.

BACKGROUND

One of the main technical challenges in producing second-generation biochemicals from cellulosic feedstocks via fermentation is reducing the negative impact of microbial inhibitors released during feedstock hydrolysis, such as acetate. Wild-type strains of *Saccharomyces cerevisiae* are severely limited in their ability to anaerobically (co)-consume acetate, an important potent inhibitor in cellulosic hydrolysates. However, introducing a heterologous NADH-specific acetylating acetaldehyde dehydrogenase (AADH) makes it thermodynamically possible for yeasts to anaerobically convert acetate into ethanol during glucose fermentation (Guadalupe et al., 2010). The authors combined expression of an AADH with a gpd-strain background, which increased ethanol titers in two separate ways: additional ethanol is produced from acetate and the sugar that is no longer directed towards glycerol formation can be fermented to ethanol instead (Guadalupe et al., 2010). However, gpd-strains generally suffer from impaired robustness (Guadalupe et al., 2014), which can make them unsuitable for industrial fermentation of inhibitory hydrolysates. In addition, even if glycerol production is abolished, the amount of acetate that can be converted to ethanol with the amount of biosynthetic surplus NADH thus made available is limited and wild-type *S. cerevisiae* strains are severely restricted in their ability to generate additional cytosolic NADH anaerobically. AADH has also been expressed by itself in a wild-type GPD+ *S. cerevisiae* background, but this only resulted in decreased production of glycerol and acetate during glucose fermentation and did not lead to net acetate consumption (Zhang et al., 2011).

Some progress has already been made to engineer yeast strains that efficiently consume acetate during anaerobic fermentation and increase ethanol titers, while maintaining strong robustness and performance, especially on non-native substrates such as xylose and arabinose. It has been observed that *S. cerevisiae* strains engineered for xylose fermentation are particularly sensitive to acetic acid during xylose fermentation, a combination highly relevant to cellulosic hydrolysates. This effect has been recognized both in strains engineered to ferment xylose through the so-called fungal pathway, through xylose reductase (XR) and xylitol dehydrogenase (XDH), as well as in strains with the bacterial pathway, through xylose isomerase (XI).

Expression of AADH in an *S. cerevisiae* background, an XR/XDH xylose pathway and an ALD6 deletion significantly increased acetate consumption during anaerobic fermentation of a glucose/xylose mixture, while decreasing glycerol and xylitol formation (Wei et al., 2013). Further improvements with this approach were achieved by increasing the expression of AADH and the first enzyme in the acetate-to-ethanol pathway, acetyl-CoA synthetase (ACS) (Zhang et al., 2016). While these studies showed promising results, efficient conversion of acetate into ethanol in the reported strains depends on the redox-imbalanced combination of NAD(P)H-consuming XR and NADH-producing XDH to generate the NADH consumed in the acetate-to-ethanol pathway. This strategy is thus only applicable to XR/XDH strains during the fermentation of xylose. Using XR/XDH strains for xylose fermentation is furthermore complicated by their typical secretion of xylitol, which reduces product yields.

Expression of AADH has also been reported in xylose-fermenting *S. cerevisiae* strains overexpressing XI instead of XR/XDH (Onishi et al., 2016), although no modifications were explored to increase acetate consumption beyond a basic level.

In a distinct approach, conversion of acetate into ethanol was linked to consumption of exogenous glycerol through overexpression of NADH-specific glycerol dehydrogenase and dihydroxyacetone kinase (producing NADH) (WO2011/149353 and US2015/0176032). While this approach is not dependent on the cofermentation of a specific sugar, as is the case for the XR/XDH pathway discussed above (which requires xylose), it does require a significant amount of exogenous glycerol to be co-fed, which may not always be economical.

A further strategy to increase the anaerobic supply of redox equivalents for reducing acetate into ethanol, which relied on the expression of an NADPH-specific primary alcohol dehydrogenase (ADH), showed a significant increase in acetate consumption during glucose fermentation, presumably in part by allowing the yeast to anaerobically produce NADH while consuming NADPH (Henningsen et al., 2015). Acetate consumption was highest when NADPH-ADH expression was combined with overexpression of ACS and the first enzyme in the NADPH-forming oxidative pentose-phosphate pathway, glucose-6-phosphate dehydrogenase (G6PDH).

There thus remains a demand in industry for a metabolic engineering strategy for efficient anaerobic acetate consumption that maintains cellular robustness and that is independent of a particular co-substrate (glycerol for glycerol-consuming strains).

BRIEF SUMMARY

The present disclosure provides a microbial host cell which is especially suited to consume acetate in anaerobia by increasing the activity of one or more proteins that function in a first metabolic pathway (to convert acetate into an alcohol in the microbial host cell), in a second metabolic pathway (to import glycerol in the recombinant microbial host cell) and in a third metabolic pathway (to convert a C5 carbohydrate into the alcohol in the microbial host cell). The microbial host cell is capable of producing glycerol by natively expressing native proteins that function in a fourth native metabolic pathway to produce glycerol.

In a first aspect, the present disclosure provides a recombinant microbial host cell having (i) a first genetic modification for increasing the activity of one or more proteins that function in a first metabolic pathway to convert acetate into an alcohol in the microbial host cell; (ii) a second genetic modification for increasing the activity of one or more proteins that function in a second metabolic pathway to import glycerol in the recombinant microbial host cell; and (iii) a third genetic modification for increasing the activity of one or more proteins that function in a third metabolic pathway to convert a C5 carbohydrate into the alcohol in the microbial host cell. The recombinant microbial host cell comprises and natively expresses native proteins that function in a fourth native metabolic pathway to produce glycerol in the microbial host cell. In an embodiment, the alcohol is ethanol. In yet another embodiments, one or more proteins that function in the first metabolic pathway are heterologous proteins. In still another embodiment, the one or more proteins that function in the first metabolic pathway comprise a protein having acetylating acetaldehyde dehydrogenase activity. In yet a further embodiment, the protein having acetylating acetaldehyde dehydrogenase activity also has alcohol dehydrogenase activity and can be, for example, an ADHE polypeptide (for example from *Bifidobacterium* sp., including *Bifidobacterium adolescentis*). In still another embodiment, the one or more protein that function in the first metabolic pathway further comprises a protein having acetyl-CoA synthetase activity which can be, for example, an ACS2 polypeptide (for example from *Saccharomyces* sp., including *Saccharomyces cerevisiae*). In an embodiment, the one or more proteins that function in the second metabolic pathway are heterologous proteins. In still another embodiment, the protein having glycerol importing activity is an STL1 polypeptide (for example from *Saccharomyces* sp., including *Saccharomyces cerevisiae* or *Pichia* sp., including *Pichia sorbitophila*). In yet another embodiment, the one or more protein that function in the third metabolic pathway are heterologous proteins. In another embodiment, the C5 carbohydrate is xylose and/or arabinose. In still a further embodiment, one or more proteins that function in the third metabolic pathway comprise a protein having xylose isomerase activity, a protein having xylulokinase activity, a protein having transketolase activity, a protein having transaldolase activity, a protein having ribose-5-phosphate isomerase and/or a protein having ribulose-phosphate 3-epimerase activity. In a further embodiment, the one or more proteins that function in the third metabolic pathway comprise the protein having xylose isomerase activity which can be, for example, from *Catonella* sp., including *Catonella morbi*. In yet another embodiment, the one or more proteins that function in the third metabolic pathway comprises an arabinose transporter, an ARAA polypeptide, an ARAB polypeptide and/or an ARAD polypeptide. In an embodiment, the ARAA, ARAB or ARAD polypeptides can be from *Bacteroides* sp., including *Bacteroides thetaiotaomicron*. In another embodiment, the recombinant microbial host cell can further comprise at least one of a first additional genetic modification, wherein the first additional genetic modification is (a) a deletion in at least one an aldose reductase gene; (b) a mutation in a polypeptide encoded by an iron-sulfur cluster gene; and/or (c) a mutation in a RAS2 polypeptide. In an embodiment, the aldose reductase gene is a GRE3 gene and/or a YPR1 gene. In still another embodiment, the iron sulfur cluster gene is a YFH1 gene, a ISU1 gene and/or a NFS1 gene. In an embodiment, the native proteins that function in the fourth native metabolic pathway to produce glycerol comprise a GPD1 protein, a GPD2 protein, a GPP1 protein and a GPP2 protein. In some embodiment, the recombinant microbial host cell further comprises a fifth genetic modification for increasing the activity of one or more heterologous proteins that function in a fifth metabolic pathway for increasing the availability of electrons in the form of a reduced redox cofactor in the microbial host cell. In still another embodiment, the fifth genetic modification is for increasing the activity of a NADPH-dependent alcohol dehydrogenase. For example, the NADPH-dependent alcohol dehydrogenase from a bacteria or a eukaryotic source and can be an ADH1 polypeptide (for example from *Entamoeba* sp., including *Entamoeba histolytica*). In such embodiment, the recombinant microbial host cell can further comprise a second additional genetic modification for increasing the activity of a protein capable of producing NADPH. Such protein can be, for example, at least one of a ZWF1 protein, a SOL3 protein and/or a GND1 protein. In an embodiment, the recombinant microbial host cell can be a yeast host cell, for example from the genus *Saccharomyces* and, in some embodiments, from the species *Saccharomyces cerevisiae.*

BRIEF DESCRIPTION OF THE DRAWINGS

Having thus generally described the nature of the invention, reference will now be made to the accompanying drawings, showing by way of illustration, a preferred embodiment thereof, and in which.

DETAILED DESCRIPTION i) Definitions

Figure 1:
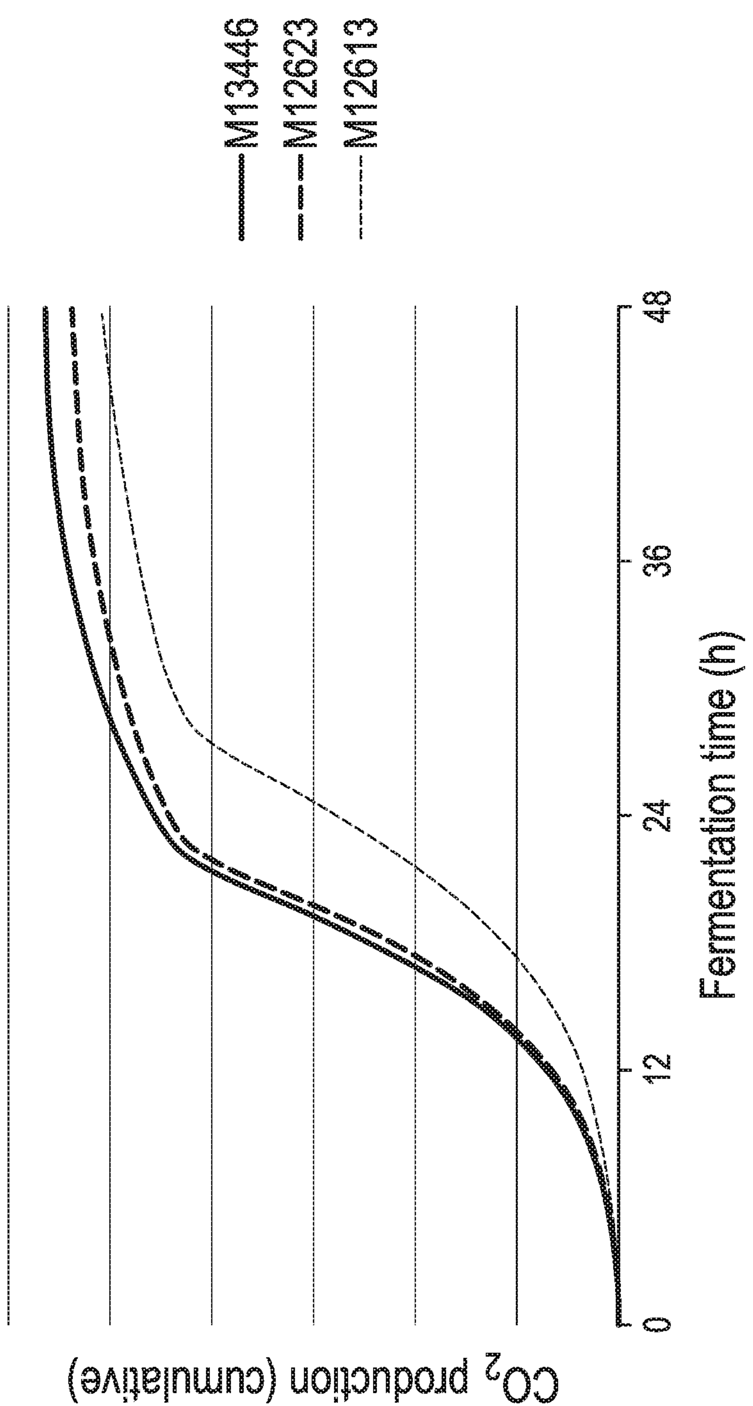
FIG. 1 compares the fermentation rate of different genetically engineered *Saccharomyces cerevisiae* strains on an industrial cellulosic medium. Results are shown as the accumulation of $CO_2$ production (measured as pressure accumulation) in function of fermentation time (measured in hours) for strains M13446, M12623 and M12613.

Unless defined otherwise, all technical and scientific terms used herein have the same meaning as commonly understood by one of ordinary skill in the art to which this invention belongs. Also, unless otherwise required by context, singular terms shall include pluralities and plural terms shall include the singular. All publications, patents and other references mentioned herein are incorporated by reference in their entireties for all purposes.

The term "increasing" when used in reference to the activity of one or more proteins encompasses both providing activity of the protein in the recombinant microbial host cell (in embodiments in which the protein was not natively expressed by the recombinant microbial host cell) and augmenting the activity of the protein in the recombinant microbial host cell (in embodiments in which the protein was natively expressed by the recombinant microbial host cell). Therefore the expression "increasing the activity" generally refers to an heightened activity of the one or more proteins, which can be heterolgous or native to the microbial host cell.

The term "heterologous" when used in reference to a polynucleotide, a gene, a protein, a polypeptide or an enzyme refers to a nucleic acid, a polynucleotide, a gene, a protein, a polypeptide, or an enzyme not normally found in the host organism. "Heterologous" also includes a native coding region, or portion thereof, that is reintroduced into the source organism in a form that is different from the corresponding native gene, e.g., not in its natural location in the organism's genome or not with its native regulatory elements (i.e. promoter and terminator). The heterologous polynucleotide or gene may be introduced into the host organism by, e.g., gene transfer. A heterologous gene/polynucleotide may include a native coding region that is a portion of a chimeric gene including non-native regulatory regions that is reintroduced into the native host. Foreign genes can comprise native genes inserted into a non-native organism, or chimeric genes. The term "heterologous" when used in reference to a nucleic acid molecule (such as a promoter, a terminator or a coding sequence) or a protein refers to a nucleic acid molecule or a protein that is not natively found in the recombinant host cell. For example, a heterologous element could be derived from a different strain of host cell, or from an organism of a different taxonomic group (e.g., different kingdom, phylum, class, order, family genus, or species, or any subgroup within one of these classifications). A heterologous element may be derived from any source, e.g., eukaryotes, prokaryotes, viruses, or synthetic polynucleotide fragments.

The heterologous nucleic acid molecules or polynucleotides present in the recombinant host cell can be integrated in the host cell's genome. The term "integrated" as used herein refers to genetic elements that are placed, through molecular biology techniques, into the genome of a host cell. For example, genetic elements can be placed into the chromosomes of the host cell as opposed to in a vector such as a plasmid carried by the host cell. Methods for integrating genetic elements into the genome of a host cell are well known in the art and include homologous recombination. The heterologous nucleic acid molecule can be present in one or more copies (e.g., 2, 3, 4, 5, 6, 7, 8, 9, 10, 11, 12 or even more copies) in the microbial host cell's genome (at the same or different loci). The heterologous nucleic acid molecule(s) can be integrated at a neutral integration site, e.g., a genomic location which does not negatively affect the growth, robustness, viability or fermentation performances of the recombinant microbial host cell. Alternatively, the heterologous nucleic acid molecule can be independently replicating from the yeast's genome. In such embodiment, the nucleic acid molecule can be stable and/or self-replicating.

In some embodiments, heterologous nucleic acid/polynucleotide molecules which can be introduced into the recombinant microbial host cells are codon-optimized with respect to the intended recipient recombinant microbial host cell. As used herein the term "codon-optimized coding region" means a nucleic acid coding region that has been adapted for expression in the cells of a given organism by replacing at least one, or more than one, codons with one or more codons that are more frequently used in the genes of that organism. In general, highly expressed genes in an organism are biased towards codons that are recognized by the most abundant tRNA species in that organism. One measure of this bias is the "codon adaptation index" or "CAI," which measures the extent to which the codons used to encode each amino acid in a particular gene are those which occur most frequently in a reference set of highly expressed genes from an organism. The CAI of codon optimized heterologous nucleic acid molecules described herein corresponds to between about 0.8 and 1.0, between about 0.8 and 0.9, or about 1.0.

The heterologous nucleic acid molecule can be introduced in the recombinant microbial host cell using a vector. A "vector," e.g., a "plasmid", "cosmid" or "artificial chromosome" (such as, for example, a yeast artificial chromosome) refers to an extra chromosomal element and is usually in the form of a circular double-stranded DNA molecule. Such vectors may be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

The heterologous polypeptides of the present disclosure can be encoded by a gene ortholog or a gene paralog. In the context of the present disclosure, a "gene ortholog" is understood to be a gene in a different species that evolved from a common ancestral gene by speciation. It is understood that the protein encoded by a gene ortholog retains the same function as the protein encoded by the original gene. Alternatively, a "gene paralog" is understood to be a gene related by duplication within the genome. In the context of the present invention, a gene paralog encodes an enzyme that could exhibit additional biological function than the native enzyme.

The heterologous nucleic acid molecules/polynucleotides described herein can comprise transcriptional and/or translational control regions. "Transcriptional and translational control regions" are DNA regulatory regions, such as promoters, enhancers, terminators, and the like, that provide for the expression of a coding region in a host cell. In eukaryotic cells, polyadenylation signals are control regions.

The terms "promoter" is intended to include a polynucleotide that can transcriptionally control a gene-of-interest that it does not transcriptionally control in nature. In certain embodiments, the transcriptional control of a promoter results in an increase in expression of the gene-of-interest under certain circumstances. In certain embodiments, a promoter is placed 5' to the gene-of-interest. A promoter may be used to replace the natural promoter, or may be used in addition to the natural promoter. A surrogate promoter may be endogenous with regard to the host cell in which it is used, or it may be a heterologous polynucleotide sequence introduced into the host cell, e.g., exogenous with regard to the host cell in which it is used.

The terms "gene(s)" or "polynucleotide(s)" or "polynucleotide sequence(s)" are intended to include nucleic acid molecules, e.g., polynucleotides which include an open reading frame encoding a polypeptide, and can further include non-coding regulatory sequences, and introns. In addition, the terms are intended to include one or more genes that map to a functional locus. In addition, the terms are intended to include a specific gene for a selected purpose. The gene may be endogenous to the host cell or may be recombinantly introduced into the host cell, e.g., as a plasmid maintained episomally or a plasmid (or fragment thereof) that is stably integrated into the genome. In addition to the plasmid form, a gene may, for example, be in the form of linear DNA. In certain embodiments, the gene or polynucleotide is involved in at least one step in the bioconversion of biomass to, e.g., ethanol.

The heterologous proteins or polypeptides of the present disclosure can be a variant of a known/native protein or polypeptide. A variant comprises at least one amino acid difference when compared to the amino acid sequence of the native protein or polypeptide. As used herein, a variant refers to alterations in the amino acid sequence that do not adversely affect the biological functions of the protein or polypeptide. A substitution, insertion or deletion is said to adversely affect the protein when the altered sequence prevents or disrupts a biological function associated with the native protein or polypeptide. For example, the overall charge, structure or hydrophobic-hydrophilic properties of the protein can be altered without adversely affecting a biological activity. Accordingly, the amino acid sequence can be altered, for example to render the peptide more hydrophobic or hydrophilic, without adversely affecting the biological activities of the food and/or feed enzyme. The protein or polypeptides variants have at least 50%, 55%, 60%, 65%, 70%, 75%, 80%, 85%, 90%, 95%, 96%, 97%, 98% or 99% identity to the native proteins and polypeptides described herein. The term "percent identity", as known in the art, is a relationship between two or more polypeptide sequences or two or more polynucleotide sequences, as determined by comparing the sequences. The level of identity can be determined conventionally using known computer programs. Identity can be readily calculated by known methods, including but not limited to those described in: Computational Molecular Biology (Lesk, $A_4$. M., ed.) Oxford University Press, N Y (1988); Biocomputing: Informatics and Genome Projects (Smith, D. W., ed.) Academic Press, N Y (1993); Computer Analysis of Sequence Data, Part I (Griffin, A. M., and Griffin, H. G., eds.) Humana Press, N J (1994); Sequence Analysis in Molecular Biology (von Heinje, G., ed.) Academic Press (1987); and Sequence Analysis Primer (Gribskov, M. and Devereux, J., eds.) Stockton Press, NY (1991). Preferred methods to determine identity are designed to give the best match between the sequences tested. Methods to determine identity and similarity are codified in publicly available computer programs. Sequence alignments and percent identity calculations may be performed using the MegAlign program of the Lasergene bioinformatics computing suite (DNASTAR Inc., Madison, Wis.). Multiple alignments of the sequences disclosed herein were performed using the Clustal method of alignment (Higgins and Sharp (1989) CABIOS. 5:151-153) with the default parameters (GAP PENALTY=10, GAP LENGTH PEN ALT Y=10). Default parameters for pairwise alignments using the Clustal method were KTUPLB 1, GAP PENALTY=3, WINDOW=5 and DIAGONALS SAVED=5.

The variant proteins or polypeptides described herein may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide for purification of the polypeptide. A "variant" of the protein or polypeptide can be a conservative variant or an allelic variant.

The heterologous proteins or polypeptides can be a fragment of a known/native/variant protein or polypeptide. A fragment comprises at least one fewer amino acid residue when compared to the amino acid sequence of the known/native/variant protein or polypeptide and still possesses the biological activity of the native protein or polypeptide. In some embodiments, protein or polypeptide "fragments" have at least at least 100, 200, 300, 400, 500, 600, 700 or more consecutive amino acids of the known/native/variant protein or polypeptide. In some embodiments, fragments have at least 50%, 55%, 60%, 65%, 70%, 75%, 80%, 85%, 90%, 95%, 96%, 97%, 98% or 99% identity to the known/native/variant proteins and polypeptides described herein. In some embodiments, fragments can be employed for producing the corresponding full-length protein or polypeptide by peptide synthesis. Therefore, the fragments can be employed as intermediates for producing the full-length proteins.

The term "transcriptional control" is intended to include the ability to modulate gene expression at the level of transcription. In certain embodiments, transcription, and thus gene expression, is modulated by replacing or adding a surrogate promoter near the 5' end of the coding region of a gene-of-interest, thereby resulting in altered gene expression. In certain embodiments, the transcriptional control of one or more genes is engineered to result in the optimal expression of such genes, e.g., in a desired ratio. The term also includes inducible transcriptional control as recognized in the art.

In the context of the present disclosure, the recombinant host cell is a microorganism and includes, without limitations, bacteria, yeasts, fungi, plant and mammalian cells. In an embodiment, the recombinant microbial host cell is a yeast and, in some additional embodiments, the yeast can be used in the production of biofuels. Suitable yeast host cells can be, for example, from the genus *Saccharomyces, Kluyveromyces, Arxula, Debaryomyces, Candida, Pichia, Phaffia, Schizosaccharomyces, Hansenula, Kloeckera, Schwanniomyces, Torula, Issatchenkia* or *Yarrowia*. Suitable yeast species can include, for example, *S. cerevisiae, S. bulderi, S. barnetti, S. exiguus, S. uvarum, S. diastaticus, C. utilis, K. lactis, K. marxianus* or *K. fragilis*. In some embodiments, the yeast is selected from the group consisting of *Saccharomyces cerevisiae, Schizosaccharomyces pombe, Candida albicans, Issatchenkia orientalis* (*Candida krusei*), *Pichia pastoris, Scheffersomyces stipitis, Yarrowia lipolytica, Ogataea polymorpha, Phaffia rhodozyma, Candida utilis, Arxula adeninivorans, Debaryomyces hansenii, Debaryomyces polymorphus, Schizosaccharomyces pombe* and *Schwanniomyces occidentalis*. In some embodiment, the host cell can be an oleaginous yeast cell. For example, the oleaginous yeast host cell can be from the genus *Blakeslea, Candida, Cryptococcus, Cunninghamella, Lipomyces, Mortierella, Mucor, Phycomyces, Pythium, Rhodosporidum, Rhodotorula, Trichosporon* or *Yarrowia*. In some alternative embodiment, the host cell can be an oleaginous microalgae host cell (e.g., for example, from the genus *Thraustochytrium* or *Schizochytrium*). In an embodiment, the recombinant yeast host cell is from the genus *Saccharomyces* and, in some embodiments, from the species *Saccharomyces cerevisiae.* ii) First Metabolic Pathway

In the context of the present disclosure, the recombinant microbial host cell comprises at least one first genetic modification for increasing the activity of one or more native and/or heterologous protein in a first (engineered) metabolic pathway to convert acetate into an alcohol such as ethanol or isopropanol. In some embodiments, this allows the recombinant microbial host cell to comprise one or more recombinantly expressed heterologous proteins that function in a first engineered metabolic pathway to convert acetate into an alcohol in the microbial host cell. For example, in an embodiment in which the one or more protein is a native protein, the first genetic modification can comprise including an heterologous promoter which increases the expression (and ultimately the activity) of the native protein to convert acetate into an alcohol. In still another example, the first genetic modification can include a mutation in the coding sequence of the protein that functions to increase the conversion of acetate into an alcohol which increases the activity of the mutated protein (when compared to the native protein). In yet another example, in an embodiment in which the one or more protein is a heterologous protein, the first genetic modification can include one or more copies of the heterologous protein to increase the expression (and ultimately the activity) of the heterologous protein to convert acetate into an alcohol. Increasing the conversion of acetate into ethanol is advantageous to reduce acetate toxicity as well as to increase ethanol production, while maintaining robustness.

In order to increase the activity of the one or more protein functioning to convert acetate into ethanol, it is possible to include, in the recombinant microbial host cell, one or more copies of a heterologous nucleic acid molecule encoding the protein functioning to convert acetate into an alcohol. For example, the recombinant microbial host cell can have one, two, three, four, five, six, seven, eight, nine, ten, eleven, twelve or more copies of the heterologous nucleic acid molecule encoding the protein functioning to convert acetate into an alcohol. In an embodiment, the recombinant microbial host cell comprises at least (and in some additional embodiments no more than) one copy of the heterologous nucleic acid molecule encoding the protein functioning to convert acetate into an alcohol. In an embodiment, the recombinant microbial host cell comprises at least (and in some additional embodiments no more than) two copies of the heterologous nucleic acid molecule encoding the protein functioning to convert acetate into an alcohol. In another embodiment, the recombinant microbial host cell comprises at least (and in some additional embodiments no more than) three copies of the heterologous nucleic acid molecule encoding the protein functioning to convert acetate into an alcohol. In yet another embodiment, the recombinant microbial host cell comprises at least (and in some additional embodiments no more than) four copies of the heterologous nucleic acid molecule encoding the protein functioning to convert acetate into an alcohol. In still another embodiment, the recombinant microbial host cell comprises at least (and in some additional embodiments no more than) five copies of the heterologous nucleic acid molecule encoding the protein functioning to convert acetate into an alcohol. In a further embodiment, the recombinant microbial host cell comprises at least (and in some additional embodiments no more than) six copies of the heterologous nucleic acid molecule encoding the protein functioning to convert acetate into an alcohol. In yet a further embodiment, the recombinant microbial host cell comprises at least (and in some additional embodiments no more than) seven copies of the heterologous nucleic acid molecule encoding the protein functioning to convert acetate into an alcohol. In still a further embodiment, the recombinant microbial host cell comprises at least (and in some additional embodiments no more than) eight copies of the heterologous nucleic acid molecule encoding the protein functioning to convert acetate into an alcohol. In still a further embodiment, the recombinant microbial host cell comprises at least (and in some additional embodiments no more than) nine copies of the heterologous nucleic acid molecule encoding the protein functioning to convert acetate into an alcohol. In still a further embodiment, the recombinant microbial host cell comprises at least (and in some additional embodiments no more than) ten copies of the heterologous nucleic acid molecule encoding the protein functioning to convert acetate into an alcohol. In still a further embodiment, the recombinant microbial host cell comprises at least (and in some additional embodiments no more than) eleven copies of the heterologous nucleic acid molecule encoding the protein functioning to convert acetate into an alcohol. In still a further embodiment, the recombinant microbial host cell comprises at least (and in some additional embodiments no more than) twelve copies of the heterologous nucleic acid molecule encoding the protein functioning to convert acetate into an alcohol. In an embodiment, the recombinant microbial host cell comprises twelve copies of the heterologous nucleic acid molecule encoding the protein functioning to convert acetate into an alcohol. The heterologous nucleic acid molecule can be independently replicating or integrated in the recombinant microbial host cell. When the heterologous nucleic acid molecule is integrated in the recombinant microbial host cell, it can be positioned at neutral integration site. When more than one copy of the heterologous nucleic acid molecule encoding the protein functioning to convert acetate is introduced in the recombinant microbial host cell, each of the copies can be integrated at one or more (the same or different) integration sites.

Acetate can be converted in ethanol by first converting acetate into acetyl-coA by the enzymatic activity of an acetyl-coA synthase (ACS). Acetyl-coA can then be converted to acetaldehyde by the enzymatic activity of an acetylating acetaldehyde dehydrogenase (AADH). Finally, acetaldehyde can be converted to ethanol by the enzymatic activity of an alcohol dehydrogenase (ADH).

As indicated above, an exemplary protein capable of functioning to convert acetate into ethanol can be an acetyl-coA synthase (ACS). Acetyl-coA synthases (ACS) catalyze the conversion of acetate into acetyl-coA and are classified in the Enzyme Commission Number class 6.2.1.1. As such, the one or more proteins that function to convert acetate into ethanol can be an acetyl-coA synthase, an acetyl-coA synthase variant, an acetyl-coA synthase fragment or be encoded by a gene ortholog of the gene encoding the acetyl-coA synthase. Exemplary proteins having acetyl-coA synthase activity can be encoded, for example by one of the following genes *Saccharomyces cerevisiae* Gene ID: 850846, *Arabidopsis thaliana* Gene ID: 837082, *Solanum lycopersicum* Gene ID: 606304, *Sugiyamaella lignohabitans* Gene ID: 30035839 and 30034559, *Triticum aestivum* Gene ID: 543237, *Scheffersomyces stipitis* Gene ID: 4840021, *Volvox carteri* f. *nagariensis* Gene ID: 9624764, *Chlamydomonas reinhardtii* Gene ID: 5725731 and *Candida albicans* Gene ID: 3644710. In an embodiment, the protein having acetyl-coA synthase activity is an ACS2 protein (derived from *Saccharomyces cerevisiae* for example) that can have the amino acid sequence of SEQ ID NO: 3, an ACS2 protein variant, an ACS2 protein fragment or a protein encoded by an ACS2 gene ortholog/paralog. In yet another embodiment, the heterologous gene coding for the ACS2 protein is present in a single copy in the recombinant microbial host cell.

In addition, the one or more proteins that function to convert acetate into ethanol can be an acetylating acetaldehyde dehydrogenase, an acetylating acetaldehyde dehydrogenase variant, an acetylating acetaldehyde dehydrogenase fragment or be encoded by a gene ortholog of the gene encoding the acetylating acetaldehyde dehydrogenase. Exemplary proteins having acetaldehyde dehydrogenase can be encoded, for example by one of the following genes *Escherichia coli* Gene ID: 945837, *Shewanella oneidensis* Gene ID: 1169879, *Streptococcus mutans* Gene ID: 1029722, *Clostridium acetobutylicum* Gene ID: 1116040, *Enterococcus faecalis* Gene ID: 1199789, *Yersinia pestis* Gene ID: 1175014, *Lactobacillus acidophilus* Gene ID: 3252921, *Lactobacillus plantarum* Gene ID: 1061605, *Clostridioides difficile* Gene ID: 4915990 and 4913165, *Vibrio fischeri* Gene ID: 3278124, *Yersinia enterocolitica* subsp. *enterocolitica* Gene ID: 4715506, *Streptococcus mitis* Gene ID: 8797547, *Streptococcus suis* Gene ID: 8154061, *Streptococcus pneumoniae* Gene ID: 933809, *Streptococcus sanguinis* Gene ID: 4808056, *Lactococcus lactis* subsp. *lactis* Gene ID: 1115832, *Streptococcus agalactiae* Gene ID: 1012803, *Clostridium botulinum* Gene ID: 5400197, *Shigella dysenteriae* Gene ID: 3796690, *Salmonella enterica* subsp. *enterica serovar Typhimurium* Gene ID: 1253268, *Shigella flexneri* Gene ID: 1024221, *Escherichia coli* Gene ID: 7158044, 7151810, 7150297 and 7150296, *Clostridium botulinum* Gene ID: 5184600, *Gossypium hirsutum* Gene ID: 107924008 and 107911678, *Gossypium raimondii* Gene ID: 105802323, *Cryptosporidium parvum* Gene ID: 3374407, *Danio rerio* Gene ID: 492710, *Alligator sinensis* Gene ID: 102375576, *Odobenus rosmarus divergens* Gene ID: 101383414, *Felis catus* Gene ID: 101082028, *Staphylococcus epidermidis* (GenBank Accession Number WP_002505668.1), *Shewanella oneidensis* (GenBank Accession Number WP_011072193.10), *Citrobacter pasteurii* (GenBank Accession Number WP_005126398.1), *Lactobacillus sakei* (GenBank Accession Number WP_011374088.1), *Lactobacillus plantarum* (GenBank Accession Number WP_003643605.1), *Brevibacillus laterosporus* (GenBank Accession Number WP_003339465.1), *Olsenella uli* (GenBank Accession Number WP_013251192.1), *Lactobacillus plantarum* (GenBank Accession Number WP_015379735.1), *Entamoeba histolytica* (GenBank Accession Number Q24803.1), *Clostridium ljungdahlii* (GenBank Accession Number WP_013238313.1), *Piromyces* sp. (GenBank Accession Number AAQ22352) and *Bifidobacterium adolescentis* (GenBank Accession Number CUN50402 or SEQ ID NO: 1). In embodiments, the one or more proteins that function to convert acetate into ethanol is a bifunctional acetaldehyde-coA/alcohol dehydrogenase.

As indicated above, the protein having acetylating acetaldehyde dehydrogenase activity can be a bifunctional protein which can also exhibit an alcohol dehydrogenase activity such as, for example, an ADHE protein from *Bifidobacterium adolescentis*. The protein having acetylating acetaldehyde dehydrogenase activity can be an ADHE protein (such as, for example, the one having the amino acid sequence of SEQ ID NO: 1), an ADHE protein variant, an ADHE protein fragment or a protein encoded by an ADHE gene ortholog/paralog. In yet another embodiment, the heterologous gene coding for the ADHE protein can be present in one, two, three, four, five, six, seven, eight, nine, ten, eleven, twelve copies or more copies in the recombinant microbial host cell. In an embodiment, the heterologous gene coding for the ADHE protein can be present in four copies in the recombinant microbial host cell. In another embodiment, the heterologous gene coding for the ADHE protein can be present in eight copies in the recombinant microbial host cell. In a further embodiment, the heterologous gene coding for the ADHE protein can be present in ten copies in the recombinant microbial host cell. In still another embodiment, the heterologous gene coding for the ADHE protein can be present in twelve copies in the recombinant microbial host cell.

In addition, the one or more proteins that function to convert acetate into ethanol can be an alcohol dehydrogenase, an alcohol dehydrogenase variant, an alcohol dehydrogenase fragment or be encoded by a gene ortholog of the gene encoding the alcohol dehydrogenase. Exemplary proteins having alcohol dehydrogenase can be encoded, for example by one of the following genes *Mus musculus* Gene ID: 11522, *Saccharomyces cerevisiae* Gene ID: 854068, *Rattus norvegicus* Gene ID: 24172, *Arabidopsis thaliana* Gene ID: 844047, *Zea mays* Gene ID: 542363, *Schizosaccharomyces pombe* Gene ID: 2538902, *Chlamydomonas reinhardtii* Gene ID: 5729132, *Solanum tuberosum* Gene ID: 102577519, *Xenopus tropicalis* Gene ID: 496861, *Vitis vinifera* Gene ID: 100232853, *Candida albicans* Gene ID: 3636489, *Volvox carteri* f. *nagariensis* Gene ID: 9620963, *Cucumis melo* Gene ID: 103500074, *Lactobacillus plantarum* Gene ID: 1061600, *Aquifex aeolicus* Gene ID: 1192812, *Scheffersomyces stipitis* Gene ID: 4836752, *Spathaspora passalidarum* Gene ID: 18875210, *Serpula lacrymans* var. *lacrymans* Gene ID: 18820813, *Glycine max* Gene ID: 100801552, *Neurospora crassa* Gene ID: 3873329, *Drosophila virilis* Gene ID: 6634390, *Drosophila mojavensis* Gene ID: 6576953, *Homo sapiens* Gene ID: 124, *Rattus norvegicus* Gene ID: 29646, *Gallus gallus* Gene ID: 771920, *Bos taurus Gene ID:* 280982, *Oryctolagus cuniculus* Gene ID: 100009283, *Oryza sativa* Gene ID: 4350053, *Hipposideros armiger* Gene ID: 109392935, *Anas platyrhynchos* Gene ID: 101804666, *Xenopus laevis* Gene ID: 398377, *Ceratitis capitata* Gene ID: 101454300, *Oryza brachyantha* Gene ID: 102719808, *Gorilla gorilla* Gene ID: 101142845, *Bactrocera oleae* Gene ID: 106621040, *Musa acuminata* Gene ID: 103995941 and 103982733, *Castor canadensis* Gene ID: 109695326, *Rhinolophus sinicus* Gene ID: 109461442, *Brassica napus* Gene ID: 106392161, *Brassica oleracea* Gene ID: 106300708, *Brassica rapa* Gene ID: 103832166, *Pelodiscus sinensis* Gene ID: 102452388, *Mus musculus* 110997 and 110991, *Saccharomyces eubayanus* Gene ID: 28931457, *Schizosaccharomyces cryophilus* Gene ID: 25036848 and 25036707, *Schizosaccharomyces octosporus* Gene ID: 25031898, *Schizosaccharomyces japonicus* Gene ID: 7050092, 7049104 and 7048162, *Candida orthopsilosis* Gene ID: 14541766, *Aspergillus nidulans* Gene ID: 2868277, *Xenopus laevis* Gene ID: 373778, *Pyrococcus furiosus* Gene ID: 1467904, *Clostridioides difficile* Gene ID: 31354717, *Clostridioides difficile* Gene ID: 31351817, *Methanococcus maripaludis* Gene ID: 2762190, *Thermotoga petrophila* Gene ID: 29653443, *Vibrio tubiashii* Gene ID: 23447604, *Clostridium botulinum* Gene ID: 19965636, *Pyrococcus furiosus* Gene ID: 13301033, *Methanococcus maripaludis* Gene ID: 10982346, *Vibrio orientalis* Gene ID: 25686470, *Bacteroides vulgatus* Gene ID: 5301727, *Caldicellulosiruptor bescii* Gene ID: 31773596, *Brachyspira hyodysenteriae* Gene ID: 31720359, *Methanobrevibacter* sp. Gene ID: 1579878, *Vibrio tasmaniensis* Gene ID: 7159841, *Clostridioides difficile* Gene ID: 4916648 and 4913210, *Thermotoga maritima* Gene ID: 896938, *Desulfovibrio vulgaris* str. *Hildenborough* Gene ID: 2793915, *Bacteroides cellulosilyticus* Gene ID: 29610521, *Eisenbergiella tayi* Gene ID: 31715080, *Clostridium beijerinckii* Gene ID: 31665570, *Dictyoglomus turgidum* Gene ID: 7083157, *Homo sapiens* Gene ID: 125, *Mus musculus* Gene ID: 26876, *Saccharomyces cerevisiae* Gene ID: 852442, *Mus musculus* Gene ID: 11668, *Homo sapiens* Gene ID: 131, *Mus musculus* Gene ID: 11529, *Saccharomyces cerevisiae* Gene ID: 852636 and 851386, *Schizosaccharomyces pombe* Gene ID: 2542714, *Streptomyces coelicolor* Gene ID: 1095683, *Nicotiana tabacum* Gene ID: 107830910, *Morus notabilis* Gene ID: 21387053 and 21384487, *Candida dubliniensis* Gene ID: 8048415, 8045940 and 8044976, *Nicotiana attenuata* Gene ID: 109208159 and 109207487, *Zeugodacus cucurbitae* Gene ID: 105211861, *Bactrocera latifrons* Gene ID: 108965731, *Malus domestica* Gene ID: 103428551 and 103409572 and *Entamoeba histolytica* (SEQ ID NO: 4).

As indicated above, in an embodiment, the protein having alcohol dehydrogenase activity can be a bifunctional protein which can also exhibit an acetaldehyde dehydrogenase activity such as, for exam, an ADHE protein from *Bifidobacterium adolescentis*. The protein having alcohol dehydrogenase activity can be an ADHE protein (such as, for example, the one having the amino acid sequence of SEQ ID NO: 1), an ADHE protein variant, an ADHE protein fragment or a protein encoded by an ADHE gene ortholog/paralog. In yet another embodiment, the heterologous gene coding for the ADHE protein can be present in one, two, three, four, five, six, seven, eight, nine, ten, eleven, twelve copies in the recombinant microbial host cell.

Acetate can be converted to isopropanol by first converting acetate into acetyl-coA by the enzymatic activity of an acetyl-coA synthase (ACS). Acetyl-coA can then be converted into acetoacetyl-coA by the enzymatic activity of an acetyl-coA acetyltransferase (AcoAAT). Acetoacetyl-coA can then be converted into acetoacetate by the enzymatic activity of an acetoacetyl-coA transferase (ACoAT). Acetoacetate can then be converted into acetone by the enzymatic activity of an acetaacetate decarboxylase (ADC). Acetone can then be converted into isopropanol by the enzymatic activity of a secondary alcohol dehydrogenase (SADH). As such, the one of more proteins that function to convert acetate into isopropanol can be an acetyl-coA synthase (ACS), an acetyl-coA acetyltransferase (AcoAAT), an acetoacetyl-coA transferase (ACoAT), an acetaacetate decarboxylase (ADC) and/or a secondary alcohol dehydrogenase (SADH) as well as corresponding variants and fragments thereof.

iii) Second Metabolic Pathway

In the context of the present disclosure, the recombinant microbial host cell has a second genetic modification for increasing the activity of one or more native and/or heterologous proteins that function in a second (engineered) metabolic pathway to import glycerol inside the recombinant microbial host cell. In some embodiments, this allows the recombinant microbial host cell to comprise one or more recombinantly expressed heterologous proteins that function in a second engineered metabolic pathway to import glycerol in the recombinant microbial host cell. For example, in an embodiment in which the one or more protein is a native protein, the second genetic modification can comprise including an heterologous promoter which increases the expression (and ultimately the activity) of the native protein capable of importing glycerol. In still another example, the second genetic recombination can cause a mutation in the coding sequence of the protein that function to import glycerol which increases the activity of the mutated protein (when compared to the native protein). In yet another example, in an embodiment in which the one or more protein is an heterologous protein, the second genetic modification can comprising introducing one or more copies of the heterologous protein to increase the expression (and ultimately the activity) of the heterologous protein to increase the import of glycerol. As shown in the Examples below, increasing the import of glycerol is advantageous to decrease glycerol production while maintaining adequate robustness (growth rates in the presence of acetate). In the context of the present disclosure, the one or more proteins that function to import glycerol specifically excludes the proteins of the fourth native metabolic pathway (described below).

In order to increase the activity of the protein functioning to import glycerol, it is possible to include, in the recombinant microbial host cell, one or more copies of an heterologous nucleic acid molecule encoding the protein functioning to import glycerol. For example, the recombinant microbial host cell can have one, two, three, four, five, six, seven, eight, nine, ten, eleven, twelve or more copies of the heterologous nucleic acid molecule encoding the protein functioning to import glycerol. In an embodiment, the recombinant microbial host cell comprises between four and eight copies of the heterologous nucleic acid molecule encoding the protein functioning to import glycerol. In an embodiment, the recombinant microbial host cell comprises at least (and in some additional embodiments no more than) two copies of the heterologous nucleic acid molecule encoding the protein functioning to import glycerol. In another embodiment, the recombinant microbial host cell comprises at least (and in some additional embodiments no more than) three copies of the heterologous nucleic acid molecule encoding the protein functioning to import glycerol. In yet another embodiment, the recombinant microbial host cell comprises at least (and in some additional embodiments no more than) four copies of the heterologous nucleic acid molecule encoding the protein functioning to import glycerol. In still another embodiment, the recombinant microbial host cell comprises at least (and in some additional embodiments no more than) five copies of the heterologous nucleic acid molecule encoding the protein functioning to import glycerol. In a further embodiment, the recombinant microbial host cell comprises at least (and in some additional embodiments no more than) six copies of the heterologous nucleic acid molecule encoding the protein functioning to import glycerol. In yet a further embodiment, the recombinant microbial host cell comprises at least (and in some additional embodiments no more than) seven copies of the heterologous nucleic acid molecule encoding the protein functioning to import glycerol. In still a further embodiment, the recombinant microbial host cell comprises at least (and in some additional embodiments no more than) eight copies of the heterologous nucleic acid molecule encoding the protein functioning to import glycerol. In an embodiment, the recombinant microbial host cell comprises four copies of the heterologous nucleic acid molecule encoding the protein functioning to import glycerol. The heterologous nucleic acid molecule can be independently replicating or integrated in the recombinant microbial host cell. When the heterologous nucleic acid molecule is integrated in the recombinant microbial host cell, it is preferably positioned at neutral integration site. When more than one copy of the heterologous nucleic acid molecule encoding the protein functioning to import glycerol is introduced in the recombinant microbial host cell, each of the copy can be integrated at one or more (the same or different) integration sites.

Exemplary proteins capable of functioning to import glycerol include aquaporins as well as glycerol facilitators. The FPS1/FPS2 protein (encoded by Gene ID 850683 in *Saccharomyces cerevisiae*) is a glycerol facilitator capable of importing glycerol inside the cell. As such, the protein capable of functioning to import glycerol can be a FPS1 protein, a FPS1 protein variant, a FPS1 protein fragment or a protein encoded by a FPS1 gene ortholog. The FPS1 protein can be derived, for example, from *Saccharomyces cerevisiae* or a corresponding ortholog found in *Pachysolen tannophilus, Komagataella pastoris, Yarrowia lipolytica* and/or *Cyberlindnera jadinii.*

Another exemplary protein capable of functioning to import glycerol is the glucose-inactivated glycerol/proton symporter STL1. The native function of the STL1 protein is the uptake of glycerol from the extracellular environment. STL1 is a member of the Sugar Porter Family which is part of the Major Facilitator Superfamily (MFS). STL1 transports glycerol by proton symport meaning that the glycerol and protons are cotransported through STL1 into the cell. In *S. cerevisiae*, STL1 expression and glycerol uptake is typically repressed when carbon sources such as glucose are available. When the cells undergo high osmotic shock, STL1 is expressed in order to help deal with the osmotic shock by transporting the osmoprotectant glycerol into the cell and increasing the intracellular glycerol concentration. In the context of the present disclosure, the protein functioning to import glycerol can be the STL1 protein, a variant of the STL1 protein, a fragment of the STL1 protein or a protein encoded by a STL1 gene ortholog/paralog.

The heterologous protein functioning to import glycerol can be encoded by a STL1 gene. The STL1 protein is natively expressed in yeasts and fungi, therefore the heterologous protein functioning to import glycerol can be derived from yeasts and fungi. STL1 genes encoding the STL1 protein include, but are not limited to, *Saccharomyces cerevisiae* Gene ID: 852149, *Candida albicans* Gene ID 3703976, *Kluyveromyces lactis* Gene ID: 2896463, *Ashbya gossypii* Gene ID: 4620396, *Eremothecium sinecaudum* Gene ID: 28724161, *Torulaspora delbrueckii* Gene ID: 11505245, *Lachancea thermotolerans* Gene ID: 8290820, *Phialophora attae* Gene ID: 28742143, *Penicillium digitatum* Gene ID: 26229435, *Aspergillus oryzae* Gene ID: 5997623, *Aspergillus fumigatus* Gene ID: 3504696, *Talaromyces atroroseus* Gene ID: 31007540, *Rasamsonia emersonii* Gene ID: 25315795, *Aspergillus flavus* Gene ID: 7910112, *Aspergillus terreus* Gene ID: 4322759, *Penicillium chrysogenum* Gene ID: 8310605, *Alternaria alternata* Gene ID: 29120952, *Paraphaeosphaeria sporulosa* Gene ID: 28767590, *Pyrenophora tritici-repentis* Gene ID: 6350281, *Metarhizium robertsii* Gene ID: 19259252, *Isaria fumosorosea* Gene ID: 30023973, *Cordyceps militaris* Gene ID: 18171218, *Pochonia chlamydosporia* Gene ID: 28856912, *Metarhizium majus* Gene ID: 26274087, *Neofusicoccum parvum* Gene ID: 19029314, *Diplodia corticola* Gene ID: 31017281, *Verticillium dahliae* Gene ID: 20711921, *Colletotrichum gloeosporioides* Gene ID: 18740172, *Verticillium albo-atrum* Gene ID: 9537052,

*Paracoccidioides lutzii* Gene ID: 9094964, *Trichophyton rubrum* Gene ID: 10373998, *Nannizzia gypsea* Gene ID: 10032882, *Trichophyton verrucosum* Gene ID: 9577427, *Arthroderma benhamiae* Gene ID: 9523991, *Magnaporthe oryzae* Gene ID: 2678012, *Gaeumannomyces graminis* var. *tritici* Gene ID: 20349750, *Togninia minima* Gene ID: 19329524, *Eutypa lata* Gene ID: 19232829, *Scedosporium apiospermum* Gene ID: 27721841, *Aureobasidium namibiae* Gene ID: 25414329, *Sphaerulina musiva* Gene ID: 27905328 as well as *Pachysolen tannophilus* GenBank Accession Numbers JQ481633 and JQ481634, *Saccharomyces paradoxus* STL1 (encoded by SEQ ID NO: 5 and shown in SEQ ID NO: 6) and *Pichia sorbitophila* (encoded by SEQ ID NO: 7 and shown in SEQ ID NO: 8). In an embodiment, the STL1 protein is encoded by *Saccharomyces cerevisiae* Gene ID: 852149 and can have, for example, the amino acid sequence of SEQ ID: 2 (a variant thereof or a fragment thereof). In still another embodiment, one, two, three, four, five, six, seven, eight, nine, ten, eleven or twelve copies of a heterologous gene coding for the STL1 protein are included in the recombinant microbial host cell. In yet another embodiment, four copies of a heterologous gene coding for the STL1 protein are included in the recombinant microbial host cell.

The heterologous protein functioning to import glycerol can be encoded by a STL1 gene as indicated herein or a STL1 gene ortholog. The heterologous protein functioning to import glycerol can be a STL1 protein as defined herein, a variant of the STL1 protein and/or a fragment of the STL1 protein. In addition, when more than one copy of the heterologous STL1 is included in the recombinant microbial cell, the plurality of heterologous nucleic acid molecules encoding the STL1 protein could be the same or different, integrated at the same or different integration sites.

Optionally, the microbial host can have a further genetic modification for decreasing the (biological) activity of a protein which functions to export glycerol (e.g., actively transport glycerol from inside the cell). The recombinant microbial host cells can have at least one genetic modification allowing it to decrease the (biological) activity of a protein which functions to export glycerol (e.g., actively transport glycerol to outside the cell). Still in the context of the present disclosure, the activity of the protein functioning to export glycerol in the recombinant microbial host cell is decreased in glycolytic conditions. The FPS1 protein is an exemplary protein which functions to export glycerol. The FPS1 protein is a channel protein located in the plasma membrane that controls the accumulation and release of glycerol in yeast osmoregulation. As such, the first genetic modification can include reducing or deleting the expression of the gene encoding the FPS1 protein during glycolytic conditions.

iv) Third Metabolic Pathway

In the context of the present disclosure, the recombinant microbial host cell comprises a third genetic modification for increasing the activity of one or more native and/or heterologous protein in a third (engineered) metabolic pathway to convert C5 carbohydrate (such as arabinose, xylose or a combination thereof) into ethanol. In some embodiments, this allows the recombinant microbial host cell to comprise one or more recombinantly expressed heterologous proteins that function in a third metabolic pathway to convert a C5 carbohydrate into the alcohol in the microbial host cell.

In an embodiment, the C5 carbohydrate is xylose and the recombinant microbial host cell is capable of converting xylose into ethanol. Xylose is a five-carbon monosaccharide that can be metabolized into useful products by a variety of organisms. There are two main pathways of xylose metabolism, each unique in the characteristic enzymes they utilize. One pathway is called the "Xylose Reductase-Xylitol Dehydrogenase" or XR-XDH pathway. Xylose reductase (XR) and xylitol dehydrogenase (XDH) are the two main enzymes used in this method of xylose degradation. XR is responsible for the reduction of xylose to xylitol and is aided by cofactors NADH or NADPH. Xylitol is then oxidized to xylulose by XDH and accomplished generally with the cofactor NAD+ (this can be done, for example, by the activity of an L-xylulose reductase (E.C. 1.1.1.10)). The second pathway is called "Xylose Isomerase" or XI pathway. The enzyme XI is responsible for direct conversion of xylose into xylulose and does not proceed via xylitol as an intermediate. Both pathways create xylulose, although the enzymes utilized are different. After production of xylulose both the XR-XDH and XI pathways proceed through enzyme xylulokinase (XKS), to further modify xylulose into xylulose-5-phosphate where it then enters the pentose phosphate pathway for further catabolism, and e.g. generate ethanol.

As such, the present disclosure provides that the microbial recombinant host cells comprises a third genetic modification for increasing the activity of one or more native or heterologous proteins that function in the third engineered metabolic pathway to convert xylose into ethanol. For example, in an embodiment in which the one or more protein is a native protein, the third genetic modification can include an heterologous promoter which increases the expression (and ultimately the activity) of the native protein to convert xylose into ethanol. In still another example, in an embodiment in which the one or more protein is a native protein, the third genetic modification can cause a mutation in the coding sequence of the protein that function to convert xylose into ethanol which increases the activity of the mutated protein (when compared to the native protein). In yet another example, in an embodiment in which the one or more protein is an heterologous protein, the third genetic modification can include one or more copies of the heterologous protein to increase the expression (and ultimately the activity) of the heterologous protein to convert xylose into ethanol.

In order to increase the activity of the protein functioning to convert xylose into ethanol, it is possible to include, in the recombinant microbial host cell, one or more copies of an heterologous nucleic acid molecule encoding the protein functioning to convert xylose into ethanol. For example, the recombinant microbial host cell can have one, two, three, four, five, six, seven, eight, nine, ten, eleven, twelve, thirteen, fourteen, fifteen, sixteen or more copies of the heterologous nucleic acid molecule encoding the protein functioning to convert xylose into ethanol. In an embodiment, the recombinant microbial host cell comprises between four and eight copies of the heterologous nucleic acid molecule encoding the protein functioning to convert xylose into ethanol. In an embodiment, the recombinant microbial host cell comprises at least (and in some additional embodiments no more than) two copies of the heterologous nucleic acid molecule encoding the protein functioning to convert xylose into ethanol. In another embodiment, the recombinant microbial host cell comprises at least (and in some additional embodiments no more than) three copies of the heterologous nucleic acid molecule encoding the protein functioning to convert xylose into ethanol. In yet another embodiment, the recombinant microbial host cell comprises at least (and in some additional embodiments no more than) four copies of the heterologous nucleic acid molecule encoding the protein functioning to convert xylose into ethanol. In still another embodiment, the recombinant microbial host cell comprises at least (and in some additional embodiments no more than) five copies of the heterologous nucleic acid molecule encoding the protein functioning to convert xylose into ethanol. In a further embodiment, the recombinant microbial host cell comprises at least (and in some additional embodiments no more than) six copies of the heterologous nucleic acid molecule encoding the protein functioning to convert xylose into ethanol. In yet a further embodiment, the recombinant microbial host cell comprises at least (and in some additional embodiments no more than) seven copies of the heterologous nucleic acid molecule encoding the protein functioning to convert xylose into ethanol. In still a further embodiment, the recombinant microbial host cell comprises at least (and in some additional embodiments no more than) eight copies of the heterologous nucleic acid molecule encoding the protein functioning to convert xylose into ethanol. In still a further embodiment, the recombinant microbial host cell comprises at least (and in some additional embodiments no more than) nine copies of the heterologous nucleic acid molecule encoding the protein functioning to convert xylose into ethanol. In still a further embodiment, the recombinant microbial host cell comprises at least (and in some additional embodiments no more than) ten copies of the heterologous nucleic acid molecule encoding the protein functioning to convert xylose into ethanol. In still a further embodiment, the recombinant microbial host cell comprises at least (and in some additional embodiments no more than) eleven copies of the heterologous nucleic acid molecule encoding the protein functioning to convert xylose into ethanol. In still a further embodiment, the recombinant microbial host cell comprises at least (and in some additional embodiments no more than) twelve copies of the heterologous nucleic acid molecule encoding the protein functioning to convert xylose into ethanol. In still a further embodiment, the recombinant microbial host cell comprises at least (and in some additional embodiments no more than) thirteen copies of the heterologous nucleic acid molecule encoding the protein functioning to convert xylose into ethanol. In still a further embodiment, the recombinant microbial host cell comprises at least (and in some additional embodiments no more than) fourteen copies of the heterologous nucleic acid molecule encoding the protein functioning to convert xylose into ethanol. In still a further embodiment, the recombinant microbial host cell comprises at least (and in some additional embodiments no more than) fifteen copies of the heterologous nucleic acid molecule encoding the protein functioning to convert xylose into ethanol. In still a further embodiment, the recombinant microbial host cell comprises at least (and in some additional embodiments no more than) sixteen copies of the heterologous nucleic acid molecule encoding the protein functioning to convert xylose into ethanol. In an embodiment, the recombinant microbial host cell comprises sixteen copies of the heterologous nucleic acid molecule encoding the protein functioning to convert xylose into ethanol. The heterologous nucleic acid molecule can be independently replicating or integrated in the recombinant microbial host cell. When the heterologous nucleic acid molecule is integrated in the recombinant microbial host cell, it is preferably positioned at neutral integration site. When more than one copy of the heterologous nucleic acid molecule encoding the protein functioning to convert xylose into ethanol is introduced in the recombinant microbial host cell, each of the copy can be integrated at one or more (the same or different) integration sites.

As indicated above, an exemplary protein capable of functioning to convert xylose into ethanol is a xylose reductase. Xylose reductases catalyze the conversion of xylose and NADP+ to NADPH and xylitol and are classified in Enzyme Commission Number class 1.1.1.307. The protein having xylose reductase activity can be native or heterologous to the recombinant microbial host cell. As such, the one or more proteins that function to convert xylose into ethanol can be a xylose reductase, a xylose reductase variant, a xylose reductase fragment or be encoded by a gene ortholog of the gene encoding the xylose reductase. Exemplary proteins having xylose reductase activity can be encoded, for example, by one of the following genes *Saccharomyces cerevisiae* Gene ID: 856504, *Candida albicans* Gene ID: 3637811, *Spathaspora passalidarum* Gene ID: 18873850, *Spathaspora passalidarum* Gene ID: 18873849, *Neurospora crassa* Gene ID: 3880080, *Rhodotorula graminis* Gene ID: 28979189, *Rhodotorula toruloides* Gene ID: 27367976, *Coccidioides posadasii* Gene ID: 9696920, *Neurospora tetrasperma* Gene ID: 20825713, *Eutypa lata* Gene ID: 19231177, *Brugia malayi* Gene ID: 6102456, *Cyberlindnera jadinii* Gene ID: 30989853, *Cyberlindnera jadinii* Gene ID: 30987720, *Gloeophyllum trabeum* Gene ID: 19299660, *Dichomitus squalens* Gene ID: 18845177, *Sugiyamaella lignohabitans* Gene ID: 30035130, *Escherichia coli* Gene ID: 14575, *Enterobacter aerogenes* Gene ID: 10792723, *Shigella dysenteriae* Gene ID: 3799695, *Klebsiella pneumoniae* subsp. *pneumoniae* Gene ID: 11849430, *Klebsiella pneumoniae* subsp. *pneumoniae* Gene ID: 11846109, *Chaetomium globosum* Gene ID: 4387651, *Xylona heveae* Gene ID: 28894354, *Sphaerulina musiva* Gene ID: 27899106, *Aspergillus fumigatus* Gene ID: 3507406, *Phialocephala scopiformis* Gene ID: 28822177, *Scheffersomyces stipitis* Gene ID: 4839234, *Marssonina brunnea* f. sp. '*multigermtubi*' Gene ID: 18765662, *Marssonina brunnea* f. sp. '*multigermtubi*' Gene ID: 18760177, *Fusarium verticillioides* Gene ID: 30067248, *Fusarium oxysporum* f. sp. *lycopersici* Gene ID: 28952604, *Magnaporthe oryzae* Gene ID: 2679231, *Magnaporthe oryzae* Gene ID: 2676633, *Metarhizium robertsii* Gene ID: 19254828, *Salmo salar* Gene ID: 100196319, *Scedosporium apiospermum* Gene ID: 27728550, *Grosmannia clavigera* Gene ID: 25974877, *Chaetomium thermophilum* var. *thermophilum* Gene ID: 18259733, *Penicillium digitatum* Gene ID: 26230358, *Fusarium graminearum* Gene ID: 23548958, *Togninia minima* Gene ID: 19327575, *Togninia minima* Gene ID: 19324058, *Eutypa lata* Gene ID: 19225623, *Colletotrichum fioriniae* Gene ID: 1903145, *Trichoderma reesei* Gene ID: 18481522, *Coprinopsis cinerea okayama* Gene ID: 6016721, *Aspergillus oryzae* Gene ID: 5991970, *Purpureocillium lilacinum* Gene ID: 28891088, *Pochonia chlamydosporia* Gene ID: 28845024, *Phialocephala scopiformis* Gene ID: 28819819, *Moniliophthora roreri* Gene ID: 19287580, *Candida tropicalis* Gene ID: 8298564, *Candida tropicalis* Gene ID: 8298550, *Aspergillus clavatus* Gene ID: 4701691, *Neosartorya fischeri* Gene ID: 4591084, *Fusarium verticillioides* Gene ID: 30065949, *Fusarium oxysporum* f. sp. *lycopersici* Gene ID: 28944059, *Metarhizium majus* Gene ID: 26274458, *Metarhizium brunneum* Gene ID: 26242741, *Hyphopichia burtonii* Gene ID: 30995750, *Trametes versicolor* Gene ID: 19410447, *Gloeophyllum trabeum* Gene ID: 19308234, *Pichia kudriavzevii* Gene ID:

31691310, *Diplodia corticola* Gene ID: 31011414, *Talaromyces atroroseus* Gene ID: 31005086, *Colletotrichum higginsianum* Gene ID: 28864958, *Debaryomyces fabryi* Gene ID: 26839549, *Aspergillus nomius* Gene ID: 26811375, *Ogataea parapolymorpha* Gene ID: 25770833, *Wickerhamomyces ciferrii* Gene ID: 23465359, *Verticillium dahliae* Gene ID: 20706550, 20702536 and 20701874, *Gaeumannomyces graminis* Gene ID: 20348746 and 20344199, *Exophiala dermatitidis* Gene ID: 20305335, *Coniosporium apollinis* Gene ID: 19904082, *Pestalotiopsis fici* Gene ID: 19272170, *Pestalotiopsis fici* Gene ID: 19269538, *Pestalotiopsis fici* Gene ID: 19266700, *Capronia epimyces* Gene ID: 19168745, *Colletotrichum gloeosporioides Nara* Gene ID: 18744050, 18735990 and 18735559, *Candida orthopsilosis* Gene ID: 14541546, *Nannizzia gypsea* Gene ID: 10029154 and 10025413, *Verticillium albo-atrum* Gene ID: 9537026, 9536837 and 9530694, *Arthroderma otae* Gene ID: 9229156 and 9223336, *Ajellomyces dermatitidis* Gene ID: 8508433, *Uncinocarpus reesii* Gene ID: 8444043, *Talaromyces stipitatus* Gene ID: 8100993, *Candida dubliniensis* Gene ID: 8048448, *Aspergillus flavus* Gene ID: 7917889, *Talaromyces marneffei* Gene ID: 7027728, *Pyrenophora tritici-repentis* Gene ID: 6347932, *Ajellomyces capsulatus* Gene ID: 5446848, *Aspergillus niger* Gene ID: 88 4977114, *Coccidioides immitis* Gene ID: 4563516, *Aspergillus terreus* Gene ID: 4317317, *Legionella pneumophila* subsp. *pneumophila* Gene ID: 19833631, *Drosophila serrata* Gene ID: 110180493, *Drosophila kikkawai* Gene ID: 108085888, *Drosophila biarmipes* Gene ID: 108031656, *Lingula anatina* Gene ID: 106181656, *Lingula anatina* Gene ID: 106171375, *Wasmannia auropunctata* Gene ID: 105461757, *Aspergillus nidulans* Gene ID: 2876201 and *Gossypium arboreum* Gene ID: 108452823.

As indicated above, an exemplary protein capable of functioning to convert xylose into ethanol is a xylitol dehydrogenase. Xylitol dehydrogenases catalyze the conversion of xylitol and NAD(P)+ to NAD(P)H and xylulose and are classified in Enzyme Commission Number classes 1.1.1.9, 1.1.1.10, and 1.1.1.B19. The protein having xylitol dehydrogenase activity can be native or heterologous to the recombinant microbial host cell. As such, the one or more proteins that function to convert xylose into ethanol can be a xylitol dehydrogenase, a xylitol dehydrogenase variant, a xylitol dehydrogenase fragment or be encoded by a gene ortholog of the gene encoding the xylitol dehydrogenase. Exemplary proteins having xylitol dehydrogenase activity can be encoded, for example, by one of the following genes *Scheffersomyces stipitis* Gene ID: 4852013, *Aspergillus fumigatus* Gene ID: 3504379, *Neosartorya fischeri* Gene ID: 4588723, *Aspergillus flavus* Gene ID: 7916321, *Burkholderia pseudomallei* Gene ID: 3096519, *Spathaspora passalidarum* Gene ID: 18873119, *Marssonina brunnea* f. sp. '*multigermtubi*' Gene ID: 18762909, *Aspergillus fumigatus* Gene ID: 3510018, *Trichosporon asahii* var. *asahii* Gene ID: 25989339, *Grosmannia clavigera* Gene ID: 25976562, *Togninia minima* Gene ID: 19323828, *Eutypa lata* Gene ID: 19231523, *Zymoseptoria tritici* Gene ID: 13400430, *Metarhizium acridum* Gene ID: 19248315, *Metarhizium brunneum* Gene ID: 26237334, *Colletotrichum gloeosporioides* Gene ID: 18746313, *Colletotrichum gloeosporioides* Gene ID: 18744455, *Trichophyton verrucosum* Gene ID: 9581453, *Candida tenuis* Gene ID: 18248090, *Neurospora crassa* Gene ID: 3880931, *Kalmanozyma brasiliensis* Gene ID: 27418672, *Rhodotorula toruloides* Gene ID: 27365983, *Pseudozyma antarctica* Gene ID: 26304285, *Grosmannia clavigera* Gene ID: 25977209, *Grosmannia clavigera* Gene ID: 25977138, *Tilletiaria anomala* Gene ID: 25266716, *Tilletiaria anomala* Gene ID: 25262877, *Cryptococcus neoformans* var. *grubii* Gene ID: 23890423 and 23888063, *Ustilago maydis* Gene ID: 23562964 and 23561726, *Cryptococcus gattii* Gene ID: 10189635 and 10186924, *Cryptococcus neoformans* var. *neoformans* Gene ID: 3256238 and 3254324, *Penicillium digitatum* Gene ID: 26232154, *Beauveria bassiana* Gene ID: 19887394, *Togninia minima* Gene ID: 19329338, *Togninia minima* Gene ID: 19326215, *Eutypa lata* Gene ID: 19232345, *Neofusicoccum parvum* Gene ID: 19019499, *Spathaspora passalidarum* Gene ID: 18872743, *Trichoderma reesei* Gene ID: 18489305, *Cordyceps militaris* Gene ID: 18169004, 18167411 and 18165647, *Aspergillus fumigatus* Gene ID: 3510395, *Aspergillus fumigatus* Gene ID: 3504124, *Moniliophthora roreri* Gene ID: 19295526, *Paracoccidioides lutzii* Gene ID: 9096001, *Aspergillus clavatus* Gene ID: 4700891, *Neosartorya fischeri* Gene ID: 4591951, *Metarhizium majus* Gene ID: 26277956 and 26273006, *Metarhizium brunneum* Gene ID: 26244190, *Trametes versicolor* Gene ID: 19409382, *Coniophora puteana* Gene ID: 19200989, *Punctularia strigosozonata* Gene ID: 18887059, *Auricularia subglabra* Gene ID: 18846596, *Dichomitus squalens* Gene ID: 18844667 and 18835513, *Fomitiporia mediterranea* Gene ID: 18674855, 18670465 and 8670457, *Colletotrichum gloeosporioides* Gene ID: 18748503, 18748273 and 18737879, *Salpingoeca rosetta* Gene ID: 16074109, *Ajellomyces dermatitidis* Gene ID: 8506409, *Talaromyces stipitatus* Gene ID: 8110045, *Aspergillus flavus* Gene ID: 7910668, *Talaromyces marneffei* Gene ID: 7023775, *Botryotinia fuckeliana* Gene ID: 5432604, *Cryptococcus gattii* Gene ID: 10190105, *Penicillium digitatum* Gene ID: 26233981, *Neofusicoccum parvum* Gene ID: 19029447, *Coprinopsis cinerea* Gene ID: 6013820, *Moniliophthora roreri* Gene ID: 19281434, *Aspergillus clavatus* Gene ID: 4704682, *Trichophyton rubrum* Gene ID: 10375531, *Arthroderma benhamiae* Gene ID: 9522667, *Arthroderma otae* Gene ID: 9228403, *Talaromyces stipitatus* Gene ID: 8105295, *Candida dubliniensis* CD36Gene ID: 8049664, *Aspergillus flavus* Gene ID: 7910657, *Talaromyces marneffei* Gene ID: 7030599, *Agrobacterium fabrum* Gene ID: 1136192, *Serratia fonticola* Gene ID: 32347422, *Salmonella* sp. Gene ID: 13920602, *Aspergillus flavus* Gene ID: 7914649, *Candida dubliniensis* Gene ID: 8048370, *Gluconobacter oxydans* Gene ID: 29878874, *Ruegeria mobilis* Gene ID: 28251902, *Gluconobacter oxydans* Gene ID: 29878967, *Aspergillus terreus* Gene ID: 4317086, *Malassezia pachydermatis* Gene ID: 28726616, *Rhodotorula graminis* Gene ID: 28974966, *Xylona heveae* Gene ID: 28900298, *Candida auris* Gene ID: 28880885, *Galdieria sulphuraria* Gene ID: 17088923, *Isaria fumosorosea* Gene ID: 30026285 and 30021036, *Purpureocillium lilacinum* Gene ID: 28892276 and 28891262, *Pochonia chlamydosporia* Gene ID: 28851412 and 28851146, *Metarhizium majus* Gene ID: 26277955, *Metarhizium brunneum* Gene ID: 26237333, *Hyphopichia burtonii* Gene ID: 30993894, *Ascoidea rubescens* Gene ID: 30968501, *Kwoniella bestiolae* Gene ID: 30208129 and 30205267, *Tsuchiyaea wingfieldii* Gene ID: 30196836 and 30189647, *Kwoniella pini* Gene ID: 30175369 and 30171228, *Kwoniella mangroviensis* Gene ID: 30165268 and 30161756, *Cutaneotrichosporon oleaginosus* Gene ID: 28983728 and 28981978, *Kwoniella dejecticola* Gene ID: 28966656 and 28965491, *Aspergillus nidulans* Gene ID: 2868103, *Aspergillus terreus* Gene ID: 4317242, *Gluconobacter oxydans* Gene ID: 29878913 and *Saccharomyces cerevisiae* Gene ID: 850759.

As indicated above, an exemplary protein capable of functioning to convert xylose into ethanol is a xylose isomerase. Xyloses isomerases catalyze the conversion of D-xylose to D-xylulose and are classified with the Enzymatic Commission class 5.3.1.5. The protein having xylose isomerase activity can be native or heterologous to the recombinant microbial host cell. As such, the one or more proteins that function to convert xylose into ethanol can be a xylose isomerase, a xylose isomerase variant, a xylose isomerase fragment or be encoded by a gene ortholog of the gene encoding the xylose isomerase. The xylose isomeras can be derived from a prokaryotic or a eukaryotic cell such as, for example, *Bacteroides thetaiotamicron, Parabacteroides distasonis, Cyllamyces aberensis, Abiotrophia defectiva, Chitinophaga pinensis, Prevotella ruminicola, Piromyces equi, Lachnoclostridium phytofermentans, Clostridium phytofermentans* and/or *Catonella morbi*. Exemplary proteins having xylose isomerase activity can be encoded, for example, by one of the following genes *Escherichia coli* Gene ID: 948141, *Streptomyces coelicolor* Gene ID: 1096592, *Bacillus licheniformis* Gene ID: 3030684, *Pseudomonas syringae* Gene ID: 1184658, *Yersinia enterocolitica* subsp. *enterocolitica* Gene ID: 4716464, *Piromyces* sp. (GenBank Accession Number CAB76571), *Catonella morbi* (GenBank Accession Number WP_023355929) and *Bacteroides* thetaiotamicron (GenBank Accession Number WP_055217966). In some embodiments, the protein having xylose isomerase activity can be provided in a chimeric form (e.g., a chimeric xylose isomerase), such as, for example, those described in US Patent Application published under 2016/040152. In an embodiment, the xylose isomerase can be from *Catonella morbi* (GenBank Accession Number WP_023355929 or SEQ ID NO: 9, a variant thereof or a fragment thereof).

As indicated above, an exemplary protein capable of functioning to convert xylose into ethanol is an xylulokinase (XKS). Xylulokinases catalyze the conversion of ATP and D-xylulose into ADP and D-xylulose 5-phosphate and are classified in the Enzyme Commission Number class 2.7.1.17. The protein having xylulokinase activity can be native or heterologous to the recombinant microbial host cells. As such, the one or more proteins that function to convert xylose into ethanol can be a xylulokinase, a xylulokinase variant, a xylulokinase fragment or be encoded by a gene ortholog of the gene encoding the xylulokinase. Exemplary proteins having xylulokinase activity can be encoded, for example by one of the following genes *Saccharomyces cerevisiae* Gene ID: 853108, *Candida albicans* Gene ID: 3648306, *Scheffersomyces stipitis* Gene ID: 4850923, *Spathaspora passalidarum* Gene ID: 18872670, *Sugiyamaella lignohabitans* Gene ID: 30034300, *Saccharomyces eubayanus* Gene ID: 28931298, *Candida orthopsilosis* Gene ID: 14538150 and *Candida dubliniensis* Gene ID: 8047525. In an embodiment, the protein having xylulokinase activity is a XKS1 protein, a XKS1 protein variant, a XKS1 protein fragment or a protein encoded by a XKS1 gene ortholog/paralog. In still another embodiment, the XKS1 protein is derived from *Saccharomyces cerevisiae*. In still a further embodiment, the XKS1 protein has the amino acid sequence of SEQ ID NO: 19, is a variant thereof or is a fragment thereof. In yet another embodiment, the heterologous gene coding for the XKS1 protein is present in two copies in the recombinant microbial host cell.

Once D-xylulose 5-phosphate is formed, it can enter the pentose phosphate pathway and be processed (directly or indirectly) by one or more of a transketolase, a transaldolase, a ribose-5-phosphate isomerase and ribulose-5-phosphate epimerase.

As indicated above, an exemplary protein capable of functioning to convert xylose into ethanol is a transketolase (TLK). Transketolases catalyze the conversion of D-xylulose-5-phosphate and aldose erythrose-4-phosphate into fructose 6-phosphate and glyceraldehyde-3-phosphate as well as the conversion of D-xylulose-5-phosphate and D-ribose-5-phosphate into sedoheptulose-7-phosphate and glyceraldehyde-3-phosphate. Transketolases are classified in the Enzyme Commission Number class 2.2.1.1. The protein having transketolase activity can be native or heterologous to the recombinant microbial host cell. As such, the one or more proteins that function to convert xylose into ethanol can be a transketolase, a transketolase variant, a transketolase fragment or be encoded by a gene ortholog/paralog of the gene encoding the transketolase. Exemplary proteins having transketolase activity can be encoded, for example by one of the following genes *Saccharomyces cerevisiae* Gene ID: 856188 and *Saccharomyces cerevisiae* Gene ID: 852414. In an embodiment, the protein having transketolase activity is a TLK1 protein, a TLK1 protein variant, a TLK1 protein fragment or a protein encoded by a TLK1 gene ortholog. In still another embodiment, the TLK1 protein is derived from *Saccharomyces cerevisiae*. In still a further embodiment, the TLK1 protein has the amino acid sequence of SEQ ID NO: 18, is a variant thereof or is a fragment thereof. In yet another embodiment, the heterologous gene coding for the TLK1 protein is present in a single copy in the recombinant microbial host cell.

As indicated above, an exemplary protein capable of functioning to convert xylose into ethanol is a transaldolase (TAL), such as, for example a sedoheptulose-7-phosphate: D-glyceraldehyde-3-phosphate transaldolase. Transaldolases catalyze the conversion of sedoheptulose 7-phosphate and glyceraldehyde 3-phosphate into erythrose 4-phosphate and fructose 6-phosphate and are classified in the Enzyme Commission Number class 2.2.1.2. The protein having transaldose activity can be native or endogenous to the recombinant microbial host cell. As such, the one or more proteins that function to convert xylose into ethanol can be encoded, for example, by one of the following genes *Saccharomyces cerevisiae* Gene ID: 851068 and 852934. In an embodiment, the protein having transaldose activity is a TAL1 protein, a TAL1 protein variant, a TAL1 protein fragment or a protein encoded by a TAL1 gene ortholog/paralog. In still another embodiment, the TAL1 protein is derived from *Saccharomyces cerevisiae*. In still another embodiment, the TAL1 protein has the amino acid sequence of SEQ ID NO: 17, is a variant thereof or a fragment thereof. In yet another embodiment, the heterologous gene coding for the TAL1 protein is present in a single copy in the recombinant microbial host cell.

As indicated above, an exemplary protein capable of functioning to convert xylose into ethanol is a ribose-5-phosphate isomerase. Ribose-5-phosphate isomerases catalyze the conversion between ribose-5-phosphate and ribulose-5-phosphate and are classified in the Enzyme Commission Number class 5.3.1.6. The protein having ribose-5-phosphate isomerase can be native or heterologous to the recombinant microbial host cell. As such, the one or more proteins that function to convert xylose into ethanol can be encoded, for example, by one of the following genes *Saccharomyces cerevisiae* Gene ID: 854262, *Sugiyamaella lignohabitans* Gene ID: 30035791, *Spathaspora passalidarum* Gene ID: 18870249, *Candida albicans* Gene ID: 3636574, *Scheffersomyces stipitis* Gene ID: 4837111 and *Zymoseptoria tritici* Gene ID: 13398936. In an embodiment, the protein having ribose-5-phosphate isomerase activity is a RKI1 protein, a RKI1 protein variant, a RKI1 protein fragment or a protein encoded by a RKI1 gene ortholog/paralog. In still another embodiment, the RKI1 protein is derived from *Saccharomyces cerevisiae*. In a further embodiment, the RKI1 protein has the amino acid sequence of SEQ ID NO 13, is a variant thereof or a fragment thereof. In yet another embodiment, the heterologous gene coding for the RKI1 protein is present in a single copy in the recombinant microbial host cell.

As indicated above, an exemplary protein capable of functioning to convert xylose into ethanol is a ribulose-phosphate 3-epimerase. Ribulose-phosphate 3-epimerases catalyze the conversion of conversion between D-ribulose 5-phosphate and D-xylulose 5-phosphate and are classified in the Enzyme Commission Number class 5.1.3.1. The protein having ribulose-phosphate 3-epimerase activity can be native or heterologous to the recombinant microbial host cell. As such, the one or more proteins that function to convert xylose into ethanol can be encoded, for example, by one of the following genes *Saccharomyces cerevisiae* Gene ID: 853322, *Sugiyamaella lignohabitans* Gene ID: 30033351, *Thalassiosira pseudonana* Gene ID: 7446232, *Chlamydomonas reinhardtii* Gene ID: 5716597, *Scheffersomyces stipitis* Gene ID: 4840854, *Aureococcus anophagefferens* Gene ID: 20229018 and *Zymoseptoria tritici* Gene ID: 13398961. In an embodiment, the protein having ribulose-5-phosphate 3-epimerase activity is a RPE1 protein, a RPE1 protein variant, a RPE1 protein fragment or a protein encoded by a RPE1 gene ortholog. In still another embodiment, the RPE1 protein is derived from *Saccharomyces cerevisiae*. In still another embodiment, the RPE1 protein has the amino acid sequence of SEQ ID NO: 15, is a variant thereof or is a fragment thereof. In yet another embodiment, the heterologous gene coding for the RPE1 protein is present in a single copy in the recombinant microbial host cell.

In another complementary or alternative embodiment, the C5 carbohydrate is arabinose. Much like xylose, arabinose can be metabolized into useful products by a variety of organisms. The conversion of arabinose into xylose may require the activity of one or more of an arabinose transporter, an arabinose isomerase (AI), a ribulokinase (RK) and a ribulose 5-phosphate epimerase (R5PE).

As such, the present disclosure provides a third genetic modification for increasing the activity of one or more proteins that function in the third engineered metabolic pathway to convert arabinose into ethanol. For example, in an embodiment in which the one or more protein is a native protein, the third genetic modification can include an heterologous promoter which increases the expression (and ultimately the activity) of the native protein to convert arabinose into ethanol. In still another example, in an embodiment in which the one or more protein is a native protein, the third genetic modification can cause a mutation in the coding sequence of the protein that function to convert arabinose into ethanol which increases the activity of the mutated protein (when compared to the native protein). In yet another example, in an embodiment in which the one or more protein is an heterologous protein, the third genetic modification can include one or more copies of the heterologous protein to increase the expression (and ultimately the activity) of the heterologous protein to convert arabinose into ethanol.

In order to increase the activity of the protein functioning to convert arabinose into ethanol, it is possible to include, in the recombinant microbial host cell, one or more copies of an heterologous nucleic acid molecule encoding the protein functioning to convert arabinose into ethanol. For example, the recombinant microbial host cell can have one, two, three, four, five, six, seven, eight, nine, ten, eleven, twelve, thirteen, fourteen, fifteen, sixteen or more copies of the heterologous nucleic acid molecule encoding the protein functioning to convert arabinose into ethanol. In an embodiment, the recombinant microbial host cell comprises between four and eight copies of the heterologous nucleic acid molecule encoding the protein functioning to convert arabinose into ethanol. In an embodiment, the recombinant microbial host cell comprises at least (and in some additional embodiments no more than) two copies of the heterologous nucleic acid molecule encoding the protein functioning to convert arabinose into ethanol. In another embodiment, the recombinant microbial host cell comprises at least (and in some additional embodiments no more than) three copies of the heterologous nucleic acid molecule encoding the protein functioning to convert arabinose into ethanol. In yet another embodiment, the recombinant microbial host cell comprises at least (and in some additional embodiments no more than) four copies of the heterologous nucleic acid molecule encoding the protein functioning to convert arabinose into ethanol. In still another embodiment, the recombinant microbial host cell comprises at least (and in some additional embodiments no more than) five copies of the heterologous nucleic acid molecule encoding the protein functioning to convert arabinose into ethanol. In a further embodiment, the recombinant microbial host cell comprises at least (and in some additional embodiments no more than) six copies of the heterologous nucleic acid molecule encoding the protein functioning to convert arabinose into ethanol. In yet a further embodiment, the recombinant microbial host cell comprises at least (and in some additional embodiments no more than) seven copies of the heterologous nucleic acid molecule encoding the protein functioning to convert arabinose into ethanol. In still a further embodiment, the recombinant microbial host cell comprises at least (and in some additional embodiments no more than) eight copies of the heterologous nucleic acid molecule encoding the protein functioning to convert arabinose into ethanol. In still a further embodiment, the recombinant microbial host cell comprises at least (and in some additional embodiments no more than) nine copies of the heterologous nucleic acid molecule encoding the protein functioning to convert arabinose into ethanol. In still a further embodiment, the recombinant microbial host cell comprises at least (and in some additional embodiments no more than) ten copies of the heterologous nucleic acid molecule encoding the protein functioning to convert arabinose into ethanol. In still a further embodiment, the recombinant microbial host cell comprises at least (and in some additional embodiments no more than) eleven copies of the heterologous nucleic acid molecule encoding the protein functioning to convert arabinose into ethanol. In still a further embodiment, the recombinant microbial host cell comprises at least (and in some additional embodiments no more than) twelve copies of the heterologous nucleic acid molecule encoding the protein functioning to convert arabinose into ethanol. In still a further embodiment, the recombinant microbial host cell comprises at least (and in some additional embodiments no more than) thirteen copies of the heterologous nucleic acid molecule encoding the protein functioning to convert arabinose into ethanol. In still a further embodiment, the recombinant microbial host cell comprises at least (and in some additional embodiments no more than) fourteen copies of the heterologous nucleic acid molecule encoding the protein functioning to convert arabinose into ethanol. In still a further embodiment, the recombinant microbial host cell comprises at least (and in some additional embodiments no more than) fifteen copies of the heterologous nucleic acid molecule encoding the protein functioning to convert arabinose into ethanol. In still a further embodiment, the recombinant microbial host cell comprises at least (and in some additional embodiments no more than) sixteen copies of the heterologous nucleic acid molecule encoding the protein functioning to convert arabinose into ethanol. In an embodiment, the recombinant microbial host cell comprises sixteen copies of the heterologous nucleic acid molecule encoding the protein functioning to convert arabinose into ethanol. The heterologous nucleic acid molecule can be independently replicating or integrated in the recombinant microbial host cell. When the heterologous nucleic acid molecule is integrated in the recombinant microbial host cell, it is preferably positioned at neutral integration site. When more than one copy of the heterologous nucleic acid molecule encoding the protein functioning to convert arabinose into ethanol is introduced in the recombinant microbial host cell, each of the copy can be integrated at one or more (the same or different) integration sites.

As indicated above, an exemplary protein capable of functioning to convert arabinose into ethanol is an arabinose transporter. An "arabinose transporter" as used herein is meant to refer to an enzyme that is capable of efficiently transporting arabinose across a membrane. In general, arabinose transporters are transmembrane proteins that selectively transport pentoses, specifically arabinose, into the cell. In the context of the present disclosure, the one or more protein for converting arabinose into ethanol can be an arabinose transporter, an arabinose transporter variant or an arabinose transporter fragment. Arabinose transporters can be derived from a number of species. These include without limitations transporters derived from *Saccharomyces cerevisiae* (GAL2), *Ambrosiozyma monospora, Candida arabinofermentans, Ambrosiozyma monospora, Kluveromyces marxianus, Pichia guillermondii* (LAT1), *Pichia guillermondii* (LAT2), *Pichia stipites, Ambrosiozyma monospora* (LAT2), *Debaryomyces hensenii, Apergillus flavus, Aspergillus terreus, Neosartorya fischeri, Aspergillus niger, Penicillium marneffei, Coccidioides posadasii, Gibberella zeae, Magnaporthe oryzae, Schizophyllum commune, Pichia stipites, Saccaharomyces cerevisiae* (HXT2), *Aspergillus clavatus* (ACLA_032060), *Sclerotinia sclerotiorum* (SS 1G_01302), *Arthroderma benhamiae* (ARB 03323), *Trichophyton equinum* (TEQG_03356), *Trichophyton tonsurans* (G_04876), *Coccidioides immitis* (CIMG_09387), *Coccidioides posadasii* (CPSG_03942), *Coccidioides posadasii* (CPC735_017640), *Botryotinia fuckeliana* (BC1G_08389), *Pyrenophora tritici-repentis* (PTRG_10527), *Ustilago maydis* (UM03895.1), *Clavispora lusitaniae* (CLUG_02297), *Pichia guillermondii* (LAT1), *Pichia guillermondii* (LAT2), *Debaryomyces hansenii* (DEHA2E01 166 g), *Pichia stipites, Candida albicans, Debaryomyces hansenii* (DEHA2B 16082g), *Kluveromyces marxianus* (LAT1), *Kluyveromyces lactis* (KLLA-ORF10059), *Lachancea thermotolerans* (KLTH0H13728g), *Kluveromyces thermotolerans, Vandenvaltozyma polyspora* (Kpol_281p3), *Zygosaccharomyces rouxii* (ZYRO0E03916g), *Pichia pastoris* (0.1833), *Candida arabinofermentans* (0.1378), *Ambrosiozyma monospora* (LAT1), *Aspergillus clavatus* (ACLA_044740), *Neosartorya fischeri* (NFIA_094320), *Aspergillus flavus* (AFLA_1 16400), *Aspergillus terreus* (ATEG_08609), *Aspergillus niger* (ANI_1 1064034), *Telaromyces stipitatus* (TSTA_124770), *Penicillium chrysogenum* (Pc20g01790), *Penicillium chrysogenum* (Pc20g01790) #2, *Gibberella zeae* (FG10921.1), *Nectria hematococco, Glomerella graminicola* (GLRG_10740), *Arabidopsis thaliana, Vandenvaltozyma polyspora, Debaryomyces hanseii, Aspergillus niger, Penicillium chrysogenum, Pichia guilermondii, Aspergillus flavus, Candida lusitnaea, Candida albicans, Kluveromyces marxianus, Pichia stipites, Candida arabinofermentans* or any suitable source of the enzyme.

In an embodiment, the one or more protein for converting arabinose into ethanol can be an inhibitor of an arabinose transporter and the third genetic modification is for decreasing or preventing the expression of such inhibitor. For example, the inhibitor can be a transcription factor which limits the expression of the arabinose transporter under certain circumstances. In some embodiments, the inhibitor is a GAL2 inhibitor, for example, a GAL80 transcription factor protein which limits the expression of the GAL2 protein. The third genetic modification can thus be a deletion in the gal80 gene which would cause a constitutive expression of the GAL2 protein (an arabinose transporter).

As indicated above, an exemplary protein capable of functioning to convert arabinose into ethanol is an arabinose isomerase (AI). An arabinose isomerase refers to an enzyme that is capable of catalyzing the chemical conversion of arabinose to ribulose (EC 5.3.1.3). Arabinose isomerase belongs to the oxidoreductase family of enzymes capable of interconverting aldoses and ketoses. In an embodiment, the arabinose isomerase can be an L-arabinose isomerase. Arabinose isomerases of the present disclosure include those derived from various species including both prokaryotic and eukaryotic species. Arabinose isomerases may be derived from *Bacillus subtilis, Mycobacterium smegmatis, Bacillus licheniformis, Lactobacillus plantarum* (AraA), *Arthrobacter aurescens* (AraA), *Clavibacter michiganensis* (AraA), *Gramella forsetii* (AraA), *Bacteroides thetaiotamicron* (AraA), *Escherichia coli* (AraA) or any other suitable source of the enzyme. In an embodiment, the arabinose isomerase is AraA from *Bacteroides thetaiotamicron* and can have the amino acid sequence of SEQ ID NO: 10 (a variant thereof or a fragment thereof). In an embodiment, the heterologous AraA is present in a single copy in the recombinant microbial host cell's genome.

As indicated above, an exemplary protein capable of functioning to convert arabinose into ethanol is a ribulokinase (RK). A ribulokinase refers to an enzyme that is capable of catalyzing the chemical reaction that phosphorylates ribulose to yield ribulose-5-phosphate (EC 2.7.1.16). In an embodiment, the ribulokinase can be an L-ribulokinase. Ribulokinases of the present disclosure include those derived from various species including both prokaryotic and eukaryotic species. Ribulokinases may be derived from *Escherichia coli* (AraB), *Lactobacillus plantarum* (AraB), *Arthrobacter aurescens* (AraB), *Clavibacter michiganensis* (AraB), *Gramella forsetii* (AraB), *Bacteroides thetaiotamicron* (AraB) or any other suitable source of the enzyme. In an embodiment, the ribulokinase is AraB from *Bacteroides thetaiotamicron* and can have the amino acid sequence of SEQ ID NO: 11 (a variant thereof or a fragment thereof). In an embodiment, the heterologous AraB is present in a single copy in the recombinant microbial host cell's genome.

As indicated above, an exemplary protein capable of functioning to convert arabinose into ethanol is and a ribulose 5-phosphate epimerase (RSPE). The ribulose 5-phosphate epimerase enzyme capable of catalyzing the interconversion of ribulose-5-phosphate and xylulose-5-phosphate (EC 5.1.3.4). In an embodiment, the ribulose 5-phosphate epimerase can be an L-ribulose 5-phosphate epimerase. Ribulose 5-phosphate epimerases of the present disclosure include those derived from various species including both prokaryotic and eukaryotic species. Ribulose 5-phosphate epimerases may be derived from *Escherichia coli* (AraD), *Lactobacillus plantarum* (AraD), *Arthrobacter aurescens* (AraD), *Clavibacter michiganensis* (AraD), *Gramella forsetti* (AraD), *Bacteroides thetaiotamicron* (AraD) or any other suitable source of the enzyme. In an embodiment, the R5PE is AraD from *Bacteroides thetaiotamicron* and can have the amino acid sequence of SEQ ID NO: 12 (a variant thereof or a fragment thereof). In an embodiment, the heterologous AraB is present in a single copy in the recombinant microbial host cell's genome.

Further genetic modifications can be introduced in the microbial host cell to facilitate or increase the conversion of a C5 carbohydrate into ethanol in genes which are not directly associated with the conversion of the carbohydrate into ethanol. Such modifications have been described in WO 2016/024215 and include one or more deletion in an aldose reductase gene (such as, form example, the GRE3 gene and/or the YPR1 gene), a mutation in a polypeptide encoded by an iron-sulfur cluster gene (such as, for example, the YFH1 polypeptide (including the T163P mutation), the ISU1 polypeptide (including the D71N, the D71G and/or the S98F mutation(s)) as well as the NFS1 polypeptide (including the L115W and/or the E458D mutation(s))) as well as a mutation in a RAS2 polypeptide (including the A66T mutation, such as, for example, those described in PCT/EP2017/056456).

v) Fourth Native Metabolic Pathway

In the context of the present disclosure, the recombinant microbial host cell comprises all native proteins that function in a fourth native metabolic pathway to produce glycerol. In the recombinant microbial host cell of the present disclosure, the biological activity of the one or more native proteins functioning to produce glycerol are not genetically modified or engineered and as such, the recombinant microbial host cell expresses natively the proteins involved in the production of glycerol. As shown in the Examples below, maintaining the native ability of the microbial host cell to produce glycerol allows it to also maintain adequate robustness (growth rate kinetics in the presence of acetate).

As used in the context of the present disclosure, the proteins that function to produce glycerol specifically excludes the proteins of the second engineered metabolic pathway. The one or more proteins that function to produce glycerol are involved in the conversion of DHAP to glycerol-3-phosphate (G3P) and the conversion of G3P to glycerol. The proteins that function to produce glycerol can be involved in the conversion of dihydroxyacetone phosphate (DHAP also known as glycerone phosphate) to G3P (such as, for example, the GPD proteins). The term "glycerol-3-phosphate dehydrogenase" or "GPD" is intended to include the enzymes capable of converting dihydroxyacetone phosphate to glycerol-3-phosphate. GPD includes those enzymes that correspond to Enzyme Commission Number 1.1.1.8. Alternatively or in combination, the one or more proteins that function to produce glycerol can be involved in the conversion of G3P to glycerol (such as, for example, the GPP proteins). The term "glycerol-3-phosphate phosphatase" or "GPP" is intended to include the enzymes capable of converting glycerol-3-phosphate to glycerol. GPP includes those enzymes that corresponding to Enzyme Commission Number 3.1.3.21.

Most eukaryotic cells express two different glycerol-3-phosphate dehydrogenases (GPDs) which are necessary for glycerol production and they are expressed in response to different cellular signals: the GPD1 and the GPD2 proteins. Both proteins share 75% amino acid identity and, while they catalyze the same reaction, the differences in their promoter sequence make them more efficient enzymes under the environmental conditions that induce their expression.

The recombinant microbial host cell of the present disclosure can natively express the NAD-dependent glycerol-3-phosphate dehydrogenase GPD1 protein or a GPD1 gene ortholog. The GPD1 protein is natively expressed in yeasts, fungi, mammalian and plant cells. GPD1 genes encoding the GPD1 protein include, but are not limited to *Saccharomyces cerevisiae* Gene ID: 851539, *Schizosaccharomyces pombe* Gene ID: 2540547, *Schizosaccharomyces pombe* Gene ID: 2540455, *Neurospora crassa* Gene ID: 3873099, *Candida albicans* Gene ID: 3643924, *Scheffersomyces stipitis* Gene ID: 4840320, *Spathaspora passalidarum* Gene ID: 18874668, *Trichoderma reesei* Gene ID: 18482691, *Nectria haematococca* Gene ID: 9668637, *Candida dubliniensis* Gene ID: 8046432, *Chlamydomonas reinhardtii* Gene ID: 5716580, *Brassica napus* Gene ID: 106365675, *Chlorella variabilis* Gene ID: 17355036, *Brassica napus* Gene ID: 106352802, *Mus musculus* Gene ID: 14555, *Homo sapiens* Gene ID: 2819, *Rattus norvegicus* Gene ID: 60666, *Sus scrofa* Gene ID: 100153250, *Gallus gallus* Gene ID: 426881, *Bos taurus* Gene ID: 525042, *Xenopus tropicalis* Gene ID: 448519, *Pan troglodytes* Gene ID: 741054, *Canis lupus familiaris* Gene ID: 607942, *Callorhinchus milii* Gene ID: 103188923, *Columba livia* Gene ID: 102088900, *Macaca fascicularis* Gene ID: 101865501, *Myotis brandtii* Gene ID: 102257341, *Heterocephalus glaber* Gene ID: 101702723, *Nannospalax galili* Gene ID: 103746543, *Mustela putorius furo* Gene ID: 101681348, *Callithrix jacchus* Gene ID: 100414900, *Labrus bergylta* Gene ID: 109980872, *Monopterus albus* Gene ID: 109969143, *Castor canadensis* Gene ID: 109695417, *Paralichthys olivaceus* Gene ID: 109635348, *Bos indicus* Gene ID: 109559120, *Hippocampus comes* Gene ID: 109507993, *Rhinolophus sinicus* Gene ID: 109443801, *Hipposideros armiger* Gene ID: 109393253, *Crocodylus porosus* Gene ID: 109324424, *Gavialis gangeticus* Gene ID: 109293349, *Panthera pardus* Gene ID: 109249099, *Cyprinus carpio* Gene ID: 109094445, *Scleropages formosus* Gene ID: 108931403, *Nanorana parkeri* Gene ID: 108789981, *Rhinopithecus bieti* Gene ID: 108543924, *Lepidothrix coronata* Gene ID: 108509436, *Pygocentrus nattereri* Gene ID: 108444060, *Manis javanica* Gene ID: 108406536, *Cebus capucinus imitator* Gene ID: 108316082, *Ictalurus punctatus* Gene ID: 108255083, *Kryptolebias marmoratus* Gene ID: 108231479, *Miniopterus natalensis* Gene ID: 107528262, *Rousettus aegyptiacus* Gene ID: 107514265, *Coturnix japonica* Gene ID: 107325705, *Protobothrops mucrosquamatus* Gene ID: 107302714, *Parus major* Gene ID: 107215690, *Marmota marmota marmota* Gene ID: 107148619, *Gekko japonicus* Gene ID: 107122513, *Cyprinodon variegatus* Gene ID: 107101128, *Acinonyx jubatus* Gene ID: 106969233, *Poecilia latipinna* Gene ID: 106959529, *Poecilia mexicana* Gene ID: 106929022, *Calidris pugnax* Gene ID: 106891167, *Sturnus vulgaris* Gene ID: 106863139, *Equus asinus* Gene ID: 106845052, *Thamnophis sirtalis* Gene ID: 106545289, *Apteryx australis mantelli* Gene ID: 106499434, *Anser cygnoides domesticus* Gene ID: 106047703, *Dipodomys ordii* Gene ID: 105987539, *Clupea harengus* Gene ID: 105897935, *Microcebus murinus* Gene ID: 105869862, *Propithecus coquereli* Gene ID: 105818148, *Aotus nancymaae*

Gene ID: 105709449, *Cercocebus atys* Gene ID: 105580359, *Mandrillus leucophaeus* Gene ID: 105527974, *Colobus angolensis palliates* Gene ID: 105507602, *Macaca nemestrina* Gene ID: 105492851, *Aquila chrysaetos canadensis* Gene ID: 105414064, *Pteropus vampyrus* Gene ID: 105297559, *Camelus dromedarius* Gene ID: 105097186, *Camelus bactrianus* Gene ID: 105076223, *Esox lucius* Gene ID: 105016698, *Bison bison bison* Gene ID: 105001494, *Notothenia coriiceps* Gene ID: 104967388, *Larimichthys crocea* Gene ID: 104928374, *Fukomys damarensis* Gene ID: 04861981, *Haliaeetus leucocephalus* Gene ID: 104831135, *Corvus cornix cornix* Gene ID: 104683744, *Rhinopithecus roxellana* Gene ID: 104679694, *Balearica regulorum gibbericeps* Gene ID: 104630128, *Tinamus guttatus* Gene ID: 104575187, *Mesitornis unicolor* Gene ID: 104539793, *Antrostomus carolinensis* Gene ID: 104532747, *Buceros rhinoceros silvestris* Gene ID: 104501599, *Chaetura pelagica* Gene ID: 104385595, *Leptosomus discolor* Gene ID: 104353902, *Opisthocomus hoazin* Gene ID: 104326607, *Charadrius vociferus* Gene ID: 104284804, *Struthio camelus australis* Gene ID: 104144034, *Egretta garzetta* Gene ID: 104132778, *Cuculus canorus* Gene ID: 104055090, *Nipponia nippon* Gene ID: 104011969, *Pygoscelis adeliae* Gene ID: 103914601, *Aptenodytes forsteri* Gene ID: 103894920, *Serinus canaria* Gene ID: 103823858, *Manacus vitellinus* Gene ID: 103760593, *Ursus maritimus* Gene ID: 103675473, *Corvus brachyrhynchos* Gene ID: 103613218, *Galeopterus variegatus* Gene ID: 103598969, *Equus przewalskii* Gene ID: 103546083, *Calypte anna* Gene ID: 103536440, *Poecilia reticulata* Gene ID: 103464660, *Cynoglossus semilaevis* Gene ID: 103386748, *Stegastes partitus* Gene ID: 103355454, *Eptesicus fuscus* Gene ID: 103285288, *Chlorocebus sabaeus* Gene ID: 103238296, *Orycteropus afer afer* Gene ID: 103194426, *Poecilia formosa* Gene ID: 103134553, *Erinaceus europaeus* Gene ID: 103118279, *Lipotes vexillifer* Gene ID: 103087725, *Python bivittatus* Gene ID: 103049416, *Astyanax mexicanus* Gene ID: 103021315, *Balaenoptera acutorostrata scammoni* Gene ID: 103006680, *Physeter catodon* Gene ID: 102996836, *Panthera tigris altaica* Gene ID: 102961238, *Chelonia mydas* Gene ID: 102939076, *Peromyscus maniculatus bairdii* Gene ID: 102922332, *Pteropus alecto* Gene ID: 102880604, *Elephantulus edwardii* Gene ID: 102844587, *Chrysochloris asiatica* Gene ID: 102825902, *Myotis davidii* Gene ID: 102754955, *Leptonychotes weddellii* Gene ID: 102730427, *Lepisosteus oculatus* Gene ID: 102692130, *Alligator mississippiensis* Gene ID: 102576126, *Vicugna pacos* Gene ID: 102542115, *Camelus ferus* Gene ID: 102507052, *Tupaia chinensis* Gene ID: 102482961, *Pelodiscus sinensis* Gene ID: 102446147, *Myotis lucifugus* Gene ID: 102420239, *Bubalus bubalis* Gene ID: 102395827, *Alligator sinensis* Gene ID: 102383307, *Latimeria chalumnae* Gene ID: 102345318, *Pantholops hodgsonii* Gene ID: 102326635, *Haplochromis burtoni* Gene ID: 102295539, *Bos mutus* Gene ID: 102267392, *Xiphophorus maculatus* Gene ID: 102228568, *Pundamilia nyererei* Gene ID: 102192578, *Capra hircus* Gene ID: 102171407, *Pseudopodoces humilis* Gene ID: 102106269, *Zonotrichia albicollis* Gene ID: 102070144, *Falco cherrug* Gene ID: 102047785, *Geospiza fortis* Gene ID: 102037409, *Chinchilla lanigera* Gene ID: 102014610, *Microtus ochrogaster* Gene ID: 101990242, *Ictidomys tridecemlineatus* Gene ID: 101955193, *Chrysemys picta* Gene ID: 101939497, *Falco peregrinus* Gene ID: 101911770, *Mesocricetus auratus* Gene ID: 101824509, *Ficedula albicollis* Gene ID: 101814000, *Anas platyrhynchos* Gene ID: 101789855, *Echinops telfairi* Gene ID: 101641551, *Condylura cristata* Gene ID: 101622847, *Jaculus jaculus* Gene ID: 101609219, *Octodon degus* Gene ID: 101563150, *Sorex araneus* Gene ID: 101556310, *Ochotona princeps* Gene ID: 101532015, *Maylandia zebra* Gene ID: 101478751, *Dasypus novemcinctus* Gene ID: 101446993, *Odobenus rosmarus divergens* Gene ID: 101385499, *Tursiops truncatus* Gene ID: 101318662, *Orcinus orca* Gene ID: 101284095, *Oryzias latipes* Gene ID: 101154943, *Gorilla gorilla* Gene ID: 101131184, *Ovis aries* Gene ID: 101119894, *Felis catus* Gene ID: 101086577, *Takifugu rubripes* Gene ID: 101079539, *Saimiri boliviensis* Gene ID: 101030263, *Papio anubis* Gene ID: 101004942, *Pan paniscus* Gene ID: 100981359, *Otolemur garnettii* Gene ID: 100946205, *Sarcophilus harrisii* Gene ID: 100928054, *Cricetulus griseus* Gene ID: 100772179, *Cavia porcellus* Gene ID: 100720368, *Oreochromis niloticus* Gene ID: 100712149, *Loxodonta africana* Gene ID: 100660074, *Nomascus leucogenys* Gene ID: 100594138, *Anolis carolinensis* Gene ID: 100552972, *Meleagris gallopavo* Gene ID: 100542199, *Ailuropoda melanoleuca* Gene ID: 100473892, *Oryctolagus cuniculus* Gene ID: 100339469, *Taeniopygia guttata* Gene ID: 100225600, *Pongo abelii* Gene ID: 100172201, *Ornithorhynchus anatinus* Gene ID: 100085954, *Equus caballus* Gene ID: 100052204, *Mus musculus* Gene ID: 100198, *Xenopus laevis* Gene ID: 399227, *Danio rerio* Gene ID: 325181, *Danio rerio* Gene ID: 406615, *Melopsittacus undulatus* Gene ID: 101872435, *Ceratotherium simum* simum Gene ID: 101408813, *Trichechus manatus* latirostris Gene ID: 101359849 and *Takifugu rubripes* Gene ID: 101071719).

The recombinant microbial host cells of the present disclosure can natively express the NAD-dependent glycerol-3-phosphate dehydrogenase GPD2 protein or a GPD2 gene ortholog. The GPD2 protein is expressed in bacteria, yeasts, fungi, mammalian and plant cells. GPD2 genes encoding the GPD2 protein include, but are not limited to *Mus musculus* Gene ID: 14571, *Homo sapiens* Gene ID: 2820, *Saccharomyces cerevisiae* Gene ID: 854095, *Rattus norvegicus* Gene ID: 25062, *Schizosaccharomyces pombe* Gene ID: 2541502, *Mus musculus* Gene ID: 14380, *Danio rerio* Gene ID: 751628, *Caenorhabditis elegans* Gene ID: 3565504, *Mesocricetus auratus* Gene ID: 101825992, *Xenopus tropicalis* Gene ID: 779615, *Macaca mulatta* Gene ID: 697192, *Bos taurus* Gene ID: 504948, *Canis lupus familiaris* Gene ID: 478755, *Cavia porcellus* Gene ID: 100721200, *Gallus gallus* Gene ID: 424321, *Pan troglodytes* Gene ID: 459670, *Oryctolagus cuniculus* Gene ID: 100101571, *Candida albicans* Gene ID: 3644563, *Xenopus laevis* Gene ID: 444438, *Macaca fascicularis* Gene ID: 102127260, *Ailuropoda melanoleuca* Gene ID: 100482626, *Cricetulus griseus* Gene ID: 100766128, *Heterocephalus glaber* Gene ID: 101715967, *Scheffersomyces stipitis* Gene ID: 4838862, *Ictalurus punctatus* Gene ID: 108273160, *Mustela putorius furo* Gene ID: 101681209, *Nannospalax galili* Gene ID: 103741048, *Callithrix jacchus* Gene ID: 100409379, *Lates calcarifer* Gene ID: 108873068, *Nothobranchius furzeri* Gene ID: 07384696, *Acanthisitta chloris* Gene ID: 103808746, *Acinonyx jubatus* Gene ID: 106978985, *Alligator mississippiensis* Gene ID: 102562563, *Alligator sinensis* Gene ID: 102380394, *Anas platyrhynchos*, *Anolis carolinensis* Gene ID: 100551888, *Anser cygnoides domesticus* Gene ID: 106043902, *Aotus nancymaae* Gene ID: 105719012, *Apaloderma vittatum* Gene ID: 104281080, *Aptenodytes forsteri* Gene ID: 103893867, *Apteryx australis mantelli* Gene ID: 106486554, *Aquila chrysaetos canadensis* Gene ID: 105412526, *Astyanax mexicanus* Gene ID: 103029081, *Austrofundulus limnaeus* Gene ID: 106535816,

*Balaenoptera acutorostrata scammoni* Gene ID: 103019768, *Balearica regulorum* gibbericeps, *Bison bison* bison Gene ID: 104988636, *Bos indicus* Gene ID: 109567519, *Bos mutus* Gene ID: 102277350, *Bubalus bubalis* Gene ID: 102404879, *Buceros rhinoceros silvestris* Gene ID: 104497001, *Calidris pugnax* Gene ID: 106902763, *Callorhinchus milii* Gene ID: 103176409, *Calypte anna* Gene ID: 103535222, *Camelus bactrianus* Gene ID: 105081921, *Camelus dromedarius* Gene ID: 105093713, *Camelus ferus* Gene ID: 102519983, *Capra hircus* Gene ID: 102176370, *Cariama cristata* Gene ID: 104154548, *Castor canadensis* Gene ID: 109700730, *Cebus capucinus imitator* Gene ID: 108316996, *Cercocebus atys* Gene ID: 105576003, *Chaetura pelagica* Gene ID: 104391744, *Charadrius vociferus* Gene ID: 104286830, *Chelonia mydas* Gene ID: 102930483, *Chinchilla lanigera* Gene ID: 102017931, *Chlamydotis macqueenii* Gene ID: 104476789, *Chlorocebus sabaeus* Gene ID: 103217126, *Chrysemys picta* Gene ID: 101939831, *Chrysochloris asiatica* Gene ID: 102831540, *Clupea harengus* Gene ID: 105902648, *Colius striatus* Gene ID: 104549356, *Colobus angolensis palliates* Gene ID: 105516852, *Columba livia* Gene ID: 102090265, *Condylura cristata* Gene ID: 101619970, *Corvus brachyrhynchos, Coturnix japonica* Gene ID: 107316969, *Crocodylus porosus* Gene ID: 109322895, *Cuculus canorus* Gene ID: 104056187, *Cynoglossus semilaevis* Gene ID: 103389593, *Dasypus novemcinctus* Gene ID: 101428842, *Dipodomys ordii* Gene ID: 105996090, *Echinops telfairi* Gene ID: 101656272, *Egretta garzetta* Gene ID: 104135263, *Elephantulus edwardii* Gene ID: 102858276, *Eptesicus fuscus* Gene ID: 103283396, *Equus asinus* Gene ID: 106841969, *Equus caballus* Gene ID: 100050747, *Equus przewalskii* Gene ID: 103558835, *Erinaceus europaeus* Gene ID: 103114599, *Eurypyga helias* Gene ID: 104502666, *Falco cherrug* Gene ID: 102054715, *Falco peregrinus* Gene ID: 101912742, *Felis catus* Gene ID: 101089953, *Ficedula albicollis* Gene ID: 101816901, *Fukomys damarensis* Gene ID: 104850054, *Fundulus heteroclitus* Gene ID: 105936523, *Galeopterus variegatus* Gene ID: 103586331, *Gavia stellata* Gene ID: 104250365, *Gavialis gangeticus* Gene ID: 109301301, *Gekko japonicus* Gene ID: 107110762, *Geospiza fortis* Gene ID: 102042095, *Gorilla gorilla* Gene ID: 101150526, *Haliaeetus albicilla* Gene ID: 104323154, *Haliaeetus leucocephalus* Gene ID: 104829038, *Haplochromis burtoni* Gene ID: 102309478, *Hippocampus comes* Gene ID: 109528375, *Hipposideros armiger* Gene ID: 109379867, ktidomys *tridecemlineatus* Gene ID: 101965668, *Jaculus jaculus* Gene ID: 101616184, *Kryptolebias marmoratus* Gene ID: 108251075, *Labrus bergylta* Gene ID: 109984158, *Larimichthys crocea* Gene ID: 104929094, *Latimeria chalumnae* Gene ID: 102361446, *Lepidothrix coronata* Gene ID: 108501660, *Lepisosteus oculatus* Gene ID: 102691231, *Leptonychotes weddellii* Gene ID: 102739068, *Leptosomus discolor* Gene ID: 104340644, *Lipotes vexillifer* Gene ID: 103074004, *Loxodonta africana* Gene ID: 100654953, *Macaca nemestrina* Gene ID: 105493221, *Manacus vitellinus* Gene ID: 103757091, *Mandrillus leucophaeus* Gene ID: 105548063, *Manis javanica* Gene ID: 108392571, *Marmota marmota* marmota Gene ID: 107136866, *Maylandia zebra* Gene ID: 101487556, *Mesitornis unicolor* Gene ID: 104545943, *Microcebus murinus* Gene ID: 105859136, *Microtus ochrogaster* Gene ID: 101999389, *Miniopterus natalensis* Gene ID: 107525674, *Monodelphis domestica* Gene ID: 100014779, *Monopterus albus* Gene ID: 109957085, *Myotis brandtii* Gene ID: 102239648, *Myotis davidii* Gene ID: 102770109, *Myotis lucifugus* Gene ID: 102438522, *Nanorana parkeri* Gene ID: 108784354, *Nestor notabilis* Gene ID: 104399051, *Nipponia nippon* Gene ID: 104012349, *Nomascus leucogenys* Gene ID: 100590527, *Notothenia coriiceps* Gene ID: 104964156, *Ochotona princeps* Gene ID: 101530736, *Octodon degus* Gene ID: 101591628, *Odobenus rosmarus* divergens Gene ID: 101385453, *Oncorhynchus kisutch* Gene ID: 109870627, *Opisthocomus hoazin* Gene ID: 104338567, *Orcinus orca* Gene ID: 101287409, *Oreochromis niloticus* Gene ID: 100694147, *Ornithorhynchus anatinus* Gene ID: 100081433, *Orycteropus afer* afer Gene ID: 103197834, *Oryzias latipes* Gene ID: 101167020, *Otolemur garnettii* Gene ID: 100966064, *Ovis aries* Gene ID: 443090, *Pan paniscus* Gene ID: 100970779, *Panthera pardus* Gene ID: 109271431, *Panthera tigris altaica* Gene ID: 102957949, *Pantholops hodgsonii* Gene ID: 102323478, *Papio anubis* Gene ID: 101002517, *Paralichthys olivaceus* Gene ID: 109631046, *Pelodiscus sinensis* Gene ID: 102454304, *Peromyscus maniculatus bairdii* Gene ID: 102924185, *Phaethon lepturus* Gene ID: 104624271, *Phalacrocorax carbo* Gene ID: 104049388, *Physeter catodon* Gene ID: 102978831, *Picoides pubescens* Gene ID: 104296936, *Poecilia latipinna* Gene ID: 106958025, *Poecilia mexicana* Gene ID: 106920534, *Poecilia reticulata* Gene ID: 103473778, *Pongo abelii* Gene ID: 100452414, *Propithecus coquereli* Gene ID: 105807399, *Protobothrops mucrosquamatus* Gene ID: 107289584, *Pseudopodoces humilis* Gene ID: 102109711, *Pterocles gutturalis* Gene ID: 104461236, *Pteropus alecto* Gene ID: 102879110, *Pteropus vampyrus* Gene ID: 105291402, *Pundamilia nyererei* Gene ID: 102200268, *Pygocentrus nattereri* Gene ID: 108411786, *Pygoscelis adeliae* Gene ID: 103925329, *Python bivittatus* Gene ID: 103059167, *Rhincodon typus* Gene ID: 109920450, *Rhinolophus sinicus* Gene ID: 109445137, *Rhinopithecus bieti* Gene ID: 108538766, *Rhinopithecus roxellana* Gene ID: 104654108, *Rousettus aegyptiacus* Gene ID: 107513424, *Saimiri boliviensis* Gene ID: 101027702, *Salmo salar* Gene ID: 106581822, *Sarcophilus harrisii* Gene ID: 100927498, *Scleropages formosus* Gene ID: 108927961, *Serinus canaria* Gene ID: 103814246, *Sinocyclocheilus grahami*Gene ID: 107555436, *Sorex araneus* Gene ID: 101543025, *Stegastes partitus* Gene ID: 103360018, *Struthio camelus australis* Gene ID: 104138752, *Sturnus vulgaris* Gene ID: 106861926, *Sugiyamaella lignohabitans* Gene ID: 30033324, *Sus scrofa* Gene ID: 397348, *Taeniopygia guttata* Gene ID: 100222867, *Takifugu rubripes* Gene ID: 101062218, *Tarsius syrichta* Gene ID: 103254049, *Tauraco erythrolophus* Gene ID: 104378162, *Thamnophis sirtalis* Gene ID: 106538827, *Tinamus guttatus* Gene ID: 104572349, *Tupaia chinensis* Gene ID: 102471148, *Tursiops truncatus* Gene ID: 101330605, *Ursus maritimus* Gene ID: 103659477, *Vicugna pacos* Gene ID: 102533941, *Xiphophorus maculatus* Gene ID: 102225536, *Zonotrichia albicollis* Gene ID: 102073261, *Ciona intestinalis* Gene ID: 100183886, *Meleagris gallopavo* Gene ID: 100546408, *Trichechus manatus latirostris* Gene ID: 101355771, *Ceratotherium simum* simum Gene ID: 101400784, *Melopsittacus undulatus* Gene ID: 101871704, *Esox lucius* Gene ID: 10502249 and *Pygocentrus nattereri* Gene ID: 108411786. In an embodiment, the GPD2 protein is encoded by *Saccharomyces cerevisiae* Gene ID: 854095.

The recombinant microbial host cells of the present disclosure can natively express the glycerol-1-phosphatase 1 (GPP1) protein or a GPP1 gene ortholog/paralog. The GPP1 protein is expressed in eukaryotic cells (including yeasts, animals and humans) as well as in plants. GPP1 genes encoding the GPP1 protein include, but are not limited to *Saccharomyces cerevisiae* Gene ID: 854758, *Arabidopsis*

*thaliana* Gene ID: 828690, *Scheffersomyces stipitis* Gene ID: 4836794, *Chlorella variabilis* Gene ID: 17352997, *Solanum tuberosum* Gene ID: 102585195, *Homo sapiens* Gene ID: 7316, *Millerozyma farinosa* Gene ID: 14521241, 14520178, 1451927 and 14518181, *Sugiyamaella lignohabitans* Gene ID: 30035078, *Candida dubliniensis* Gene ID: 8046759.

The recombinant microbial host cells of the present disclosure can natively express the glycerol-1-phosphatase GPP2 protein or a GPP2 gene ortholog/paralog. The GPP2 protein is expressed in eukaryotic cells (including yeasts) as well as in plants. GPP2 genes encoding the GPP2 protein include, but are not limited to *Saccharomyces cerevisiae* Gene ID: 856791, *Sugiyamaella lignohabitans* Gene ID: 30035078, *Arabidopsis thaliana* Gene ID: 835849, *Nicotiana attenuata* Gene ID: 109234217, *Candida albicans* Gene ID: 3640236, *Candida glabrata* Gene ID: 2891433, 2891243 and 2889223.

In an embodiment, the recombinant microbial host cell natively expresses at least one (and in an embodiment no more than one) of the GPD1, GPD2, GPP1 and/or GPP2 protein. In another embodiment, the recombinant microbial host cell natively expresses has at least two (and in an embodiment no more than two) of the GPD1, GPD2, GPP1 and/or GPP2 protein. In a further embodiment, the recombinant microbial host cell natively expresses has at least three (and in an embodiment no more than three) of the GPD1, GPD2, GPP1 and/or GPP2 protein. In a further embodiment, the recombinant microbial host cell natively expresses the GPD1, GPD2, GPP1 and GPP2 proteins.

In still another embodiment, the recombinant microbial host cell natively expresses at least one NAD-dependent glycerol-3-phosphate dehydrogenase GPD protein and at least one glycerol-1-phosphatase (GPP) protein. For example, the recombinant microbial host cell can natively express the GPD1 and the GPP1 proteins but not the GPD2 and the GPP2 proteins. In another example, the recombinant microbial host cell can natively express the GPD1 and GPP2 proteins but not the GPD2 and GPP1 proteins. In still another example, the recombinant microbial host cell can natively express the GPD2 and GPP1 proteins but not the GPD1 and the GPP2 proteins. In still a further example, the recombinant microbial host cell can natively express the GPD2 and GPP2 proteins but not the GPD1 and GPP1 proteins. In another embodiment, the recombinant microbial host cell can natively express both GPD proteins (GPD1 and GPD2) and only one GPP protein (GPP1 or GPP2). In still a further embodiment, the recombinant microbial host cell can natively express only one GPD protein (GPD1 or GPD2) and both GPP proteins (GPP1 and GPP2).

vi) Fifth Metabolic Pathway

In the context of the present disclosure, the recombinant microbial host cell can have a fifth and optional genetic modification for increasing the activity of one or more native and/or heterologous proteins that function in a fifth (engineered) metabolic pathway to increase the availability of electrons in the form of reduced redox cofactors such as, for example, NADH or NAD(P)H. In some embodiments, this allows the recombinant microbial host cell to comprise one or more recombinantly expressed heteterologous proteins that function in the fifth metabolic pathway. The heterologous proteins that function in the fifth engineered metabolic pathway were described in WO2014074895. For example, in an embodiment in which the one or more protein is a native protein, the fifth genetic modification can include an heterologous promoter which increases the expression (and ultimately the activity) of the native protein to increase the availability of electrons in the form of reduced redox cofactors. In still another example, in an embodiment in which the one or more protein is a native protein, the fifth genetic modification can include a mutation in the coding sequence of the protein that function to increase the availability of electrons in the form or reduced redox cofactors which increases the activity of the mutated protein (when compared to the native protein). In yet another example, in an embodiment in which the one or more protein is an heterologous protein, the fifth genetic modification can include one or more copies of the heterologous protein to increase the expression (and ultimately the activity) of the heterologous protein to increase the availability of electrons in the form of a reduced redox cofactors.

When the microbial recombinant host cell includes a first genetic modification for increasing the activity of a protein having both acetylating acetaldehyde dehydrogenase activity and alcohol dehydrogenase activity, the fifth genetic modification can be made to increase the activity of an NADPH-dependent alcohol dehydrogenase. The protein having NADPH-dependent alcohol dehydrogenase activity can be an ADH1 polypeptide (for example from *Entamoeba* sp., including *Entamoeba histolytica* (such as, for example, the one having the amino acid sequence of SEQ ID NO: 4), an ADH1 polypeptide variant, an ADH1 polypeptide fragment or a polypeptide encoded by an ADH1 gene ortholog/paralog. In yet another embodiment, the heterologous gene coding for the NADPH-dependent alcohol dehydrogenase protein is present in one, two, three, four or more copies in the recombinant microbial host cell.

In order to increase the activity of one or more proteins functioning to increase the availability of electrons in the form of a reduced redox cofactor, it is possible to include, in the recombinant microbial host cell, one or more copies of an heterologous nucleic acid molecule encoding the protein functioning in the fifth engineered metabolic pathway. For example, the recombinant microbial host cell can have one, two, three, four, five, six, seven, eight, nine, ten, eleven, twelve or more copies of the heterologous nucleic acid molecule encoding the protein in the fifth engineered metabolic pathway. In an embodiment, the recombinant microbial host cell comprises between one and four copies of the heterologous nucleic acid molecule encoding the protein functioning in the fifth engineered metabolic pathway. In an embodiment, the recombinant microbial host cell comprises at least (and in some additional embodiments no more than) one copy of the heterologous nucleic acid molecule encoding the protein functioning in the fifth engineered metabolic pathway. In an embodiment, the recombinant microbial host cell comprises at least (and in some additional embodiments no more than) two copies of the heterologous nucleic acid molecule encoding the protein functioning in the fifth engineered metabolic pathway. In another embodiment, the recombinant microbial host cell comprises at least (and in some additional embodiments no more than) three copies of the heterologous nucleic acid molecule encoding the protein functioning in the fifth engineered metabolic pathway. In yet another embodiment, the recombinant microbial host cell comprises at least (and in some additional embodiments no more than) four copies of the heterologous nucleic acid molecule encoding the protein functioning in the fifth engineered metabolic pathway. In still another embodiment, the recombinant microbial host cell comprises at least (and in some additional embodiments no more than) five copies of the heterologous nucleic acid molecule encoding the protein functioning in the fifth engineered metabolic pathway. In a further embodiment, the recombinant microbial host cell comprises at least (and in some additional embodiments no more than) six copies of the heterologous nucleic acid molecule encoding the protein functioning in the fifth engineered metabolic pathway. In yet a further embodiment, the recombinant microbial host cell comprises at least (and in some additional embodiments no more than) seven copies of the heterologous nucleic acid molecule encoding the protein functioning in the fifth engineered metabolic pathway. In still a further embodiment, the recombinant microbial host cell comprises at least (and in some additional embodiments no more than) eight copies of the heterologous nucleic acid molecule encoding the protein functioning in the fifth engineered metabolic pathway. In an embodiment, the recombinant microbial host cell comprises one copy of the heterologous nucleic acid molecule encoding the protein functioning in the fifth engineered metabolic pathway. The heterologous nucleic acid molecule can be independently replicating or integrated in the recombinant microbial host cell. When the heterologous nucleic acid molecule is integrated in the recombinant microbial host cell, it is preferably positioned at neutral integration site. When more than one copy of the heterologous nucleic acid molecule encoding the protein functioning in the fifth engineered metabolic pathway is introduced in the recombinant microbial host cell, each of the copy can be integrated at one or more (the same or different) integration sites.

In some instances, it may be advisable to support the enzymatic activity of the protein having NADPH-dependent alcohol dehydrogenase activity by increasing the activity of one or more proteins capable of producing NADPH by introducing a second additional genetic modification. For example, the second additional genetic modification can be made to one or more proteins capable of increasing the flux through an oxidative pentose phosphate pathway. As shown in the Examples below, increasing the flux through an oxidative pentose phosphate pathway is advantageous to increase conversion of acetate into ethanol while maintaining adequate robustness (growth rates, kinetics in the presence of acetate).

The one or more proteins capable of producing NADPH can be involved in the conversion of glucose-6-phosphate to ribulose-5-phosphate. The one or more proteins capable of producing NADPH can include a glucose-6-phosphate dehydrogenase which catalyzes the conversion of glucose-6-phosphate to D-6-phospho-glucono-δ-lactone and thereby produces NAD(P)H. Existing glucose-6-phosphate dehydrogenases are classified in the Enzyme Commission Number class 1.1.1.49. The glucose-6-phosphate dehydrogenases that can be overexpressed include, but are not limited to, *Saccharomyces cerevisiae* Gene ID: 855480, *Schizosaccharomyces pombe* Gene ID: 2543200, *Mycobacterium tuberculosis* Gene ID: 885817, *Candida albicans* Gene ID: 3634913, *Scheffersomyces stipitis* Gene ID: 4840428, *Spathaspora passalidarum* Gene ID: 18873881, *Trichoderma reesei* Gene ID: 18488529, *Sugiyamaella lignohabitans* Gene ID: 30033743, *Pseudomonas syringae* Gene ID: 1182936, *Saccharomyces eubayanus* Gene ID: 28933643, *Tilletiaria anomala* Gene ID: 25263324, *Candida orthopsilosis* Gene ID: 14536750, *Candida dubliniensis* Gene ID: 8045036, *Ashbya gossypii* Gene ID: 4618820, *Yarrowia lipolytica* Gene ID: 2912994, *Debaryomyces hansenii* Gene ID: 2900295, *Eremothecium sinecaudum* Gene ID: 28721758, *Lachancea thermotolerans* Gene ID: 8294207, *Vandenvaltozyma polyspora* Gene ID: 5543493, *Torulaspora delbrueckii* Gene ID: 11503674, *Naumovozyma dairenensis* Gene ID: 11497048, *Naumovozyma dairenensis* Gene ID: 11496104, *Candida glabrata* Gene ID: 2889898, *Millerozyma farinosa* Gene ID: 14524780, *Millerozyma farinosa* Gene ID: 14523985, *Tetrapisispora blattae* Gene ID: 14497097, *Kazachstania africana* Gene ID: 13886105, *Kazachstania africana* Gene ID: 13885322, *Tetrapisispora phaffii* Gene ID: 11530753 and/or *Kluyveromyces lactis* Gene ID: 3293693. In an embodiment, the glucose-6-phosphate dehydrogenase is a ZWF1 protein (for example from *Saccharomyces* sp., including *Saccharomyces cerevisiae* for example), a ZWF1 protein variant, a ZWF1 protein fragment or a protein encoded by a ZWF1 gene ortholog/paralog. In still a further embodiment, the ZWF1 protein has the amino acid sequence of SEQ ID NO: 20, is a variant thereof or is a fragment thereof. In yet another embodiment, a single copy of an heterologous gene coding for the ZWF1 protein is included in the recombinant microbial host cell.

The one or more proteins capable of producing NADPH can include a 6-phosphogluconolactonase which catalyzes the conversion of D-6-phospho-glucono-δ-lactone in 6-phospho-D-gluconate. Existing 6-phosphogluconolactonases are classified in the Enzyme Commission Number class 3.1.1.31. The 6-phosphogluconolactonases that can be overexpressed include, but are not limited to *Saccharomyces cerevisiae* Gene ID: 856568, *Candida albicans* Gene ID: 3646625, *Saccharomyces eubayanus* Gene ID: 28931703, *Candida orthopsilosis* Gene ID: 14540431, *Saccharomyces cerevisiae* Gene ID: 853163, *Millerozyma farinosa* Gene ID: 14522418, *Saccharomyces cerevisiae* S288c Gene ID: 853155, *Saccharomyces eubayanus* Gene ID: 28931348. In an embodiment, the 6-phosphogluconolactonase is a SOL3 or SOL4 protein (from *Saccharomyces cerevisiae* for example), a SOL3 or SOL4 protein variant, a SOL3 or SOL4 protein fragment or a protein encoded by a SOL3 or SOL4 gene ortholog. In another embodiment, the 6-phosphogluconolactonase is a SOL3 protein, a SOL3 protein variant, a SOL3 protein fragment or a protein encoded by a SOL3 gene ortholog/paralog. In still another embodiment, the 6-phosphogluconolactonase is a SOL3 protein (for example from *Saccharomyces* sp., including *Saccharomyces cerevisiae* for example). In yet another embodiment, the SOL3 protein has the amino acid sequence of SEQ ID NO: 16, a variant thereof or a fragment thereof. In still another embodiment, a single copy of a heterologous gene coding for a SOL3 protein is included in the recombinant microbial host cell.

The one or more proteins capable of producing NADPH can include a 6-phosphogluconate dehydrogenase which catalyzes the conversion of 6-phospho-D-gluconate in ribulose-5-phosphate and thus produces $CO_2$. Existing 6-phosphogluconate dehydrogenases are classified in the Enzyme Commission Number class 1.1.1.44. The 6-phosphogluconate dehydrogenases that can be overexpressed include, but are not limited to *Saccharomyces cerevisiae* Gene ID: 856589, *Mycobacterium tuberculosis* Gene ID: 885755, *Candida albicans* Gene ID: 3636131, *Scheffersomyces stipitis* Gene ID: 4851939, *Spathaspora passalidarum* Gene ID: 18871521, *Zymoseptoria tritici* Gene ID: 13402018, *Ascoidea rubescens* Gene ID: 30968350, *Aspergillus fumigatus* Gene ID: 3508701, *Saitoella complicata* Gene ID: 30186746, *Sphaerulina musiva* Gene ID: 27902722, *Candida orthopsilosis* Gene ID: 14540072, *Talaromyces stipitatus* Gene ID: 8102542, *Aspergillus flavus* Gene ID: 7913831, *Talaromyces marneffei* Gene ID: 7024375, *Saccharomyces eubayanus* Gene ID: 28931722, *Clavispora lusitaniae* Gene ID: 8496367, *Clavispora lusitaniae* Gene ID: 8496118, *Saccharomyces cerevisiae* Gene ID: 853172, *Sugiyamaella lignohabitans* Gene ID: 30035723, *Mycobac-*

*terium tuberculosis* Gene ID: 885820, *Lactobacillus plantarum* Gene ID: 1062157, *Gardnerella vaginalis* Gene ID: 9904914, *Enterococcus faecium* Gene ID: 13000204, *Mycobacterium leprae* Gene ID: 909952, *Saccharomyces eubayanus* Gene ID: 28931358*, Synechococcus phage* Gene ID: 4239176 and *Meyerozyma guilliermondii* Gene ID: 5124800. In an embodiment, the 6-phosphogluconate dehydrogenase is a GND1 or GND2 protein (from *Saccharomyces cerevisiae* for example), a GND1 or GND2 protein variant, a GND1 or GND2 protein fragment or a protein encoded by a GND1 or GND2 gene ortholog/paralog. In another embodiment, the 6-phosphogluconate dehydrogenase is a GND1 protein, a GND1 protein variant, a GND1 protein fragment or a protein encoded by a GND1 gene ortholog/paralog. In still another embodiment, the GND1 protein has the amino acid sequence of SEQ ID NO: 13, is a variant thereof or is a fragment thereof. In yet another embodiment, a single copy of an heterologous gene coding for the GND1 protein is included in the recombinant microbial host cell.

The recombinant microbial host cell of the present disclosure can include a second additional genetic modification to express at least one of a glucose-6-phosphate dehydrogenase (the ZWF1 protein for example), a 6-phosphogluconolactonase (the SOL3 protein for example) and a 6-phosphogluconate dehydrogenase (the GND1 protein for example). In still another embodiment, the recombinant microbial host cell of the present disclosure can include a second additional genetic modification to express at least two of a glucose-6-phosphate dehydrogenase (the ZWF1 protein for example), a 6-phosphogluconolactonase (the SOL3 protein for example) and a 6-phosphogluconate dehydrogenase (the GND1 protein for example). In yet another embodiment, the microbial host cell of the present disclosure can include of a second additional genetic modification to express a glucose-6-phosphate dehydrogenase (the ZWF1 protein for example), a 6-phosphogluconolactonase (the SOL3 protein for example) and a 6-phosphogluconate dehydrogenase (the GND1 protein for example) In such embodiments, one or more of these proteins can be derived from *S. cerevisiae*. In addition, the nucleic acid sequences encoding these one or more heterologous proteins can be present in a single copy or more in the microbial recombinant host cell.

In yet another example, the second additional genetic modification for increasing the activity of one or more proteins capable of making NADPH can be made (i) for increasing the activity of one or more proteins in a xylose fermentation pathway (for example by upregulating the expression of the native and/or heterologous xylose reductase (XR) and xylitol dehydrogenase (XDH) enzymes), (ii) for modulating the activity of transcription factors that regulate expression of enzymes of the pentose phosphate pathway (PPP), (iii) for decreasing the activity of the native enzyme glucose-6-P isomerase that competes with the oxidative branch of the PPP, (iv) for increasing the activity of one or more proteins in the ribulose-monophosphate pathway (RuMP, for the conversion fructose-6-P into ribulose-5-P and formaldehyde), (v) for increasing the activity of one or more proteins that function in the dihydroxyacetone (DHA) pathway (for the interconversion of dihydroxyacetone and glyceraldehyde-3-P into xylose-5-P and formaldehyde) and/or (vi) for decreasing the activity of a native dihydroxyacetone kinase enzyme.

vii) Process for Making Ethanol

The recombinant microbial host cell of the present disclosure can advantageously be used in a process for making ethanol. As described herein and shown in the Examples, the recombinant microbial host cell has an increased tolerance towards acetate. As such, the recombinant microbial host cell of the present disclosure can be used to make ethanol in the presence, for example, of less than 20 g/l of acetate (and in some embodiments between 4 to 14 g/l of acetate). In some embodiments, the recombinant microbial cell produces more ethanol than a corresponding strain, due to the direct conversion of acetate to ethanol, and optionally also due to the reduced need to produce glycerol for reoxidizing surplus NADH, which can now be consumed in the conversion of acetate to ethanol, which provides an alternative anaerobic redox sink for NADH.

A further advantage of using the recombinant microbial host cell is that it does not require exogenous glycerol addition to produce ethanol from acetate. As such, the recombinant microbial host cell of the present disclosure are used in a process in which no exogenous glycerol in included in the fermentable substrate.

In the present disclosure the recombinant microorganism can be used to produce ethanol from biomass, which is referred to herein as lignocellulosic material, lignocellulosic substrate, or cellulosic biomass.

In addition, to producing ethanol, the recombinant microorganisms as described herein can be combined, either as recombinant host cells or as engineered metabolic pathways in recombinant host cells, alone, with additional purified enzymes and/or with additional microorganisms (recombinant or not).

Numerous cellulosic substrates can be used in accordance with the present invention. Substrates for cellulose activity assays can be divided into two categories, soluble and insoluble, based on their solubility in water. Soluble substrates include cellodextrins or derivatives, carboxymethyl cellulose (CMC), or hydroxyethyl cellulose (HEC). Insoluble substrates include crystalline cellulose, microcrystalline cellulose (Avicel), amorphous cellulose, such as phosphoric acid swollen cellulose (PASC), dyed or fluorescent cellulose, and pretreated lignocellulosic biomass. These substrates are generally highly ordered cellulosic material and thus only sparingly soluble.

The terms "lignocellulosic material", "lignocellulosic substrate" and "cellulosic biomass" mean any type of biomass comprising cellulose, hemicellulose, lignin, or combinations thereof, such as but not limited to woody biomass, forage grasses, herbaceous energy crops, non-woody-plant biomass, agricultural wastes and/or agricultural residues, forestry residues and/or forestry wastes, paper-production sludge and/or waste paper sludge, waste-water-treatment sludge, municipal solid waste, corn fiber from wet and dry mill corn ethanol plants, and sugar-processing residues. The terms "hemicellulosics", "hemicellulosic portions" and "hemicellulosic fractions" mean the non-lignin, non-cellulose elements of lignocellulosic material, such as but not limited to hemicellulose (i.e., comprising xyloglucan, xylan, glucuronoxylan, arabinoxylan, mannan, glucomannan, and galactoglucomannan, among others), pectins (e.g., homogalacturonans, rhamnogalacturonan I and II, and xylogalacturonan), and proteoglycans (e.g., arabinogalactan-protein, extensin, and proline-rich proteins).

In a non-limiting example, the lignocellulosic material can include, but is not limited to, woody biomass, such as recycled wood pulp fiber, sawdust, hardwood, softwood, and combinations thereof; grasses, such as switch grass, cord grass, rye grass, reed canary grass, miscanthus, or a combination thereof; sugar-processing residues, such as but not limited to sugar cane bagasse; agricultural wastes, such as but not limited to rice straw, rice hulls, barley straw, corn cobs, cereal straw, wheat straw, canola straw, oat straw, oat hulls, and corn fiber; stover, such as but not limited to soybean stover, corn stover; succulents, such as but not limited to, Agave; and forestry wastes, such as but not limited to, recycled wood pulp fiber, sawdust, hardwood (e.g., poplar, oak, maple, birch, willow), softwood, or any combination thereof. Lignocellulosic material may comprise one species of fiber; alternatively, lignocellulosic material may comprise a mixture of fibers that originate from different lignocellulosic materials. Other lignocellulosic materials are agricultural wastes, such as cereal straws, including wheat straw, barley straw, canola straw and oat straw; corn fiber; stovers, such as corn stover and soybean stover; grasses, such as switch grass, reed canary grass, cord grass, and miscanthus; or combinations thereof.

Paper sludge is also a viable feedstock for ethanol production. Paper sludge is solid residue arising from pulping and paper-making, and is typically removed from process wastewater in a primary clarifier. At a disposal cost of $30/wet ton, the cost of sludge disposal equates to $5/ton of paper that is produced for sale. The cost of disposing of wet sludge is a significant incentive to convert the material for other uses, such as conversion to ethanol.

It will be appreciated that suitable lignocellulosic material may be any feedstock that contains soluble and/or insoluble cellulose, where the insoluble cellulose may be in a crystalline or non-crystalline form. In various embodiments, the lignocellulosic biomass comprises, for example, wood, corn, corn stover, sawdust, bark, leaves, agricultural and forestry residues, grasses such as switchgrass, ruminant digestion products, municipal wastes, paper mill effluent, newspaper, cardboard or combinations thereof.

In some embodiments, the recombinant microbial host cell of the present disclosure can be used for hydrolyzing a cellulosic substrate, for example a cellulosic substrate as described above, by contacting the cellulosic substrate with a recombinant microorganism of the invention. In some embodiments, the recombinant microbial host cell of the present disclosure can be used for hydrolyzing a cellulosic substrate, for example a cellulosic substrate as described above, by contacting the cellulosic substrate with a co-culture comprising yeast cells expressing heterologous cellulases.

In some embodiments, the recombinant microbial host cell of the present disclosure can be used for fermenting cellulose. Such methods can be accomplished, for example, by culturing a host cell or co-culture in a medium that contains insoluble cellulose to allow saccharification and fermentation of the cellulose.

The production of ethanol can, according to the present process, be performed at temperatures of at least about 20° C., 21° C., 22° C., 23° C., 24° C., 25° C., 26° C., 27° C., 28° C., 29° C., 30° C., about 31° C., about 32° C., about 33° C., about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., or about 50° C.

In some embodiments, the processes can comprise contacting a cellulosic substrate with a recombinant microorganism or co-culture of the invention and additionally contacting the cellulosic substrate with externally produced cellulase enzymes. Exemplary externally produced cellulase enzymes are commercially available and are known to those of skill in the art.

In some embodiments, the methods comprise producing ethanol at a particular rate. For example, in some embodiments, ethanol is produced at a rate of at least about 0.1 mg per hour per liter, at least about 0.25 mg per hour per liter, at least about 0.5 mg per hour per liter, at least about 0.75 mg per hour per liter, at least about 1.0 mg per hour per liter, at least about 2.0 mg per hour per liter, at least about 5.0 mg per hour per liter, at least about 10 mg per hour per liter, at least about 15 mg per hour per liter, at least about 20.0 mg per hour per liter, at least about 25 mg per hour per liter, at least about 30 mg per hour per liter, at least about 50 mg per hour per liter, at least about 100 mg per hour per liter, at least about 200 mg per hour per liter, at least about 300 mg per hour per liter, at least about 400 mg per hour per liter, or at least about 500 mg per hour per liter.

In some embodiments, the recombinant microbial host cells can produce ethanol at a rate of at least about 0.1 mg per hour per liter, at least about 0.25 mg per hour per liter, at least about 0.5 mg per hour per liter, at least about 0.75 mg per hour per liter, at least about 1.0 mg per hour per liter, at least about 2.0 mg per hour per liter, at least about 5.0 mg per hour per liter, at least about 10 mg per hour per liter, at least about 15 mg per hour per liter, at least about 20.0 mg per hour per liter, at least about 25 mg per hour per liter, at least about 30 mg per hour per liter, at least about 50 mg per hour per liter, at least about 100 mg per hour per liter, at least about 200 mg per hour per liter, at least about 300 mg per hour per liter, at least about 400 mg per hour per liter, or at least about 500 mg per hour per liter more than a control strain (lacking heterologous cellulases) and grown under the same conditions. In some embodiments, the ethanol can be produced in the absence of any externally added cellulases.

Ethanol production can be measured using any method known in the art. For example, the quantity of ethanol in fermentation samples can be assessed using HPLC analysis. Many ethanol assay kits are commercially available that use, for example, alcohol oxidase enzyme based assays. Methods of determining ethanol production are within the scope of those skilled in the art from the teachings herein. The U.S. Department of Energy (DOE) provides a method for calculating theoretical ethanol yield.

The present invention will be more readily understood by referring to the following examples which are given to illustrate the invention rather than to limit its scope.

EXAMPLE

TABLE 1

Description of the genotypes of the *Saccharomyces cerevisiae* strains used in this Example. All strains, except M2390 shared expression of the heterologous xylose isomerase from *Catonella morbi* (SEQ ID NO: 9) overexpression of XKS1 (SEQ ID NO: 19), the pentose phosphate pathway genes RPE1 (SEQ ID NO: 15), TAL1 (SEQ ID NO: 17), TLK1 (SEQ ID NO: 18), RKI1 (SEQ ID NO: 14), deletions of gre3 and ypr1 (to reduce xylitol formation) and introduction of the YFH1-T163P allele (to benefit the xylose fermentation rate).

| Strains | Genotype |
|---|---|
| M2390 | Non-engineered host strain |
| M11321 | No additional modification |
| M12613 | gpd1Δ, *B. adolescentis* adhE (4x), STL1 (4x), ACS2 |
| M12623 | RAS2-A66T |
| M12747 | RAS2-A66T, gpd2Δ, *B. adolescentis* adhE (4x), STL1 (4x), ACS2 |

TABLE 1-continued

Description of the genotypes of the *Saccharomyces cerevisiae* strains used in this Example. All strains, except M2390 shared expression of the heterologous xylose isomerase from *Catonella morbi* (SEQ ID NO: 9) overexpression of XKS1 (SEQ ID NO: 19), the pentose phosphate pathway genes RPE1 (SEQ ID NO: 15), TAL1 (SEQ ID NO: 17), TLK1 (SEQ ID NO: 18), RKI1 (SEQ ID NO: 14), deletions of gre3 and ypr1 (to reduce xylitol formation) and introduction of the YFH1-T163P allele (to benefit the xylose fermentation rate).

| Strains | Genotype |
|---|---|
| M12932 | RAS2-A66T, gpd2Δ, *B. adolescentis* adhE (8x), STL1 (4x), ACS2, *E. histolytica* ADH1 (4x) |
| M13446 | RAS2-A66T, *B. adolescentis* adhE (4x), STL (4x), ACS2 |
| M13618 | RAS2-A66T, *B. adolescentis* adhE (8x), STL1 (4x), ACS2, *E. histolytica* ADH1 |
| M14507 | *B. adolescentis* adhE (4x), STL1 (4x), ASC2, *Bacteriodes thetaiotaomicron* araA, araB, araD |
| M14615 | RAS2-A66T, *B. adolescentis* adhE (10x), STL1 (4x), ACS2, *E. histolytica* ADH1 |
| M14718 | RAS2-A66T, *B. adolescentis* adhE (10x), STL1 (4x), ACS2, *E. histolytica* ADH1, ZWF1, SOL3, GND1 |
| M14745 | RAS2-A66T, *B. adolescentis* adhE (4x), STL1 (4x) |
| M14747 | RAS2-A66T, STL1(4x) |
| M14749 | RAS2-A66T, *B. adolescentis* adhE (4x) |
| M14751 | RAS2-A66T, *B. adolescentis* adhE (4x), STL1 (4x), ACS2 |
| M14754 | RAS2-A66T, *B. adolescentis* adhE (4x), ACS2 |
| M14755 | RAS2-A66T, ACS2 |
| M14712 | RAS2-A66T, *B. adolescentis* adhE (12x), STL1 (4x), ACS2, *E. histolytica* ADH1 |
| M14716 | RAS2-A66T, *B. adolescentis* adhE (10x), STL1 (4x), ACS2, *E. histolytica* ADH1, ZWF1 |
| M14719 | RAS2-A66T, *B. adolescentis* adhE (10x), STL1 (4x), ASCS2, *E. histolytica* ADH1, ZWF1, SOL3, GND1 |
| M14837 | RAS2-A66T, *B. adolescentis* adhE (10x), STL1 (4x), ACS2, *E. histolytica* ADH1, ZWF1, SOL3, GND1, gpd2Δ |
| M15339 | RAS2-A66T, *B. adolescentis* adhE (10x), STL1 (4x), ACS2, *E. histolytica* ADH1, ZWF1, SOL3, GND1, gpd2Δ, gpd1Δ |
| M15380 | RAS2-A66T, *B. adolescentis* adhE (10x), STL1 (4x), ACS2, *E. histolytica* ADH1, ZWF1, SOL3, GND1, gpd1Δ |

Strain construction. Engineered strains (Table 1) were constructed in a wild-type diploid industrial *S. cerevisiae* M2390 strain background, using standard transformation and selection techniques known to those skilled in the art, with scarless genomic integrations using integration cassettes that were targeted through homologous recombination. In the genotype descriptions in Table 1, heterologous genes are preceded by the name of their donor organism. All heterologous genes were codon-optimized for expression in *S. cerevisiae*. Unless noted otherwise, each integration cassette only contained a single copy of each listed gene (making for a total of two gene copies for both chromosome copies of the diploid strain). In the case of exceptions to this rule, the total gene copy number in the strain at the integration site is listed after the gene name in parenthesis (e.g., "(4×)" means that the integration cassette contained two copies of the listed gene, making for a total of four gene copies for both chromosome copies). All genes in integration cassettes were expressed through the use of endogenous promoters and terminators and integrated at neutral integration sites.

Cell culture and subsequent analysis. Strains were maintained in glycerol stocks at −80° C. To create a fermentation inoculum, freezer stocks were first struck to YPD plates (yeast extract, peptone, dextrose), which were then used to inoculate 5 ml $YPD_{40}$ media in 14 ml capped round-bottom tubes. After 24 hours incubation at 35° C. in a rotary drum, 2 mL culture was spun down and resuspended in water to 300 μl, which was then used to inoculate a fermentation bottle. Fermentations took place in 60 mL sealed serum bottles, filled with either 20 mL or 30 mL of media, which were then incubated at 32° C. in a rotary shaker. The initial pH of the fermentation media was adjusted to 5.5. Off-gas production was continuously monitored through either accumulated pressure (which was periodically vented) or continuous mass flow (with no pressure buildup). Once the fermentations had reached their end, final high performance liquid chromatography (HPLC) measurements were taken.

Fermentation on $YPD_{60}X60Ace_9$ medium. Strains to be tested were struck out onto a $YPD_{40}$ (10 g/L yeast extract, 20 g/L peptone, 40 g/L dextrose, and 15 g/L agarose) agar plate and incubated for 2 days at 30° C. A 10 uL inoculum loop sized cell mass scraped of the agar plate was then used to inoculate one 250 mL erlenmeyer flask for each strain with a 55 mL volume of $YPD_{40}$ and incubated at 32° C. and 200 RPM for 20 hours. A 50 mL volume of the liquid cultures were spun down at 4000 RPM for 3 minutes in 50 mL tubes, decanted, and reconstituted with a 3 mL volume of sterile water. To determine the dry cell weight (DCW) of each of the samples for inoculation, a 1 mL volume of each sample was analyzed using a Sartorius LMA200 moisture meter. The fermentation medium $YPD_{60}X60Ace_9$ (10 g/L yeast extract, 20 g/L peptone, 60 g/L dextrose, 60 g/L xylose, and 9 g/L acetic acid from potassium acetate set at an initial pH of 4.9 using sulfuric acid) was aliquoted at a volume of 30 mL into 60 mL serum bottles in a laminar flow hood. Each strain was then inoculated at an initial DCW of 0.1 g/L in triplicate and the serum bottles were then sealed with grey butyl rubber stoppers with aluminum crimps. Bottles were vented with 23g needles and placed in an incubator (32° C. and 150 RPM), monitored with a mass flow meter for $CO_2$ production and sampled for HPLC at 24 and 48 hours looking at carbohydrates, ethanol, glycerol, and organic acids.

Fermentation on $YPD_{20}X_{10}A_{10}Ace_4Gly_1$ medium. Strains to be tested were struck out onto a $YPD_{40}$ (10 g/L yeast extract, 20 g/L peptone, 40 g/L dextrose, and 15 g/L agarose) agar plate and incubated for 2 days at 30° C. A 10 uL inoculum loop sized cell mass scraped of the agar plate was then used to inoculate one 250 mL erlenmeyer flask for each strain with a 55 mL volume of $YPD_{40}$ and incubated at 32° C. and 200 RPM for 20 hours. A 50 mL volume of the liquid cultures were spun down at 4000 RPM for 3 minutes in 50 mL tubes, decanted, and reconstituted with a 3 mL volume of sterile water. To determine the dry cell weight (DCW) of each of the samples for inoculation, a 1 mL volume of each sample was analyzed using a Sartorius LMA200 moisture meter. The fermentation medium $YPD_{20}X_{10}A_{10}Ace_4Gly_1$ (10 g/L yeast extract, 20 g/L peptone, 20 g/L glucose, 10 g/L xylose, 10 g/L arabinose, 4 g/L acetate from potassium acetate, and 1 g/L glycerol) was aliquoted at a volume of 30 mL into 60 mL serum bottles in a laminar flow hood. Each strain was then inoculated at an initial DCW of 0.1 g/L in triplicate and the serum bottles were then sealed with grey butyl rubber stoppers with aluminum crimps. Bottles were vented with 23g needles and placed in an incubator at 32° C. and 150 RPM monitored for mass flow via Automated $CO_2$ Analysis (ACAN) taking HPLC samples the end of fermentation looking at carbohydrates, ethanol, glycerol, and organic acids.

Corn fermentation. Fermentations were run using a commercially produced pretreated corn fiber cellulosic substrate. These fermentations were set up essentially the same as those described above (Fermentation on $YPD_{20}X_{10}A_{10}Ace_4Gly_1$ medium section) except a 0.3 g/L DCW inoculum was used and the 30 mL corn fiber substrate was approximately 20% total solids.

Figure 2:
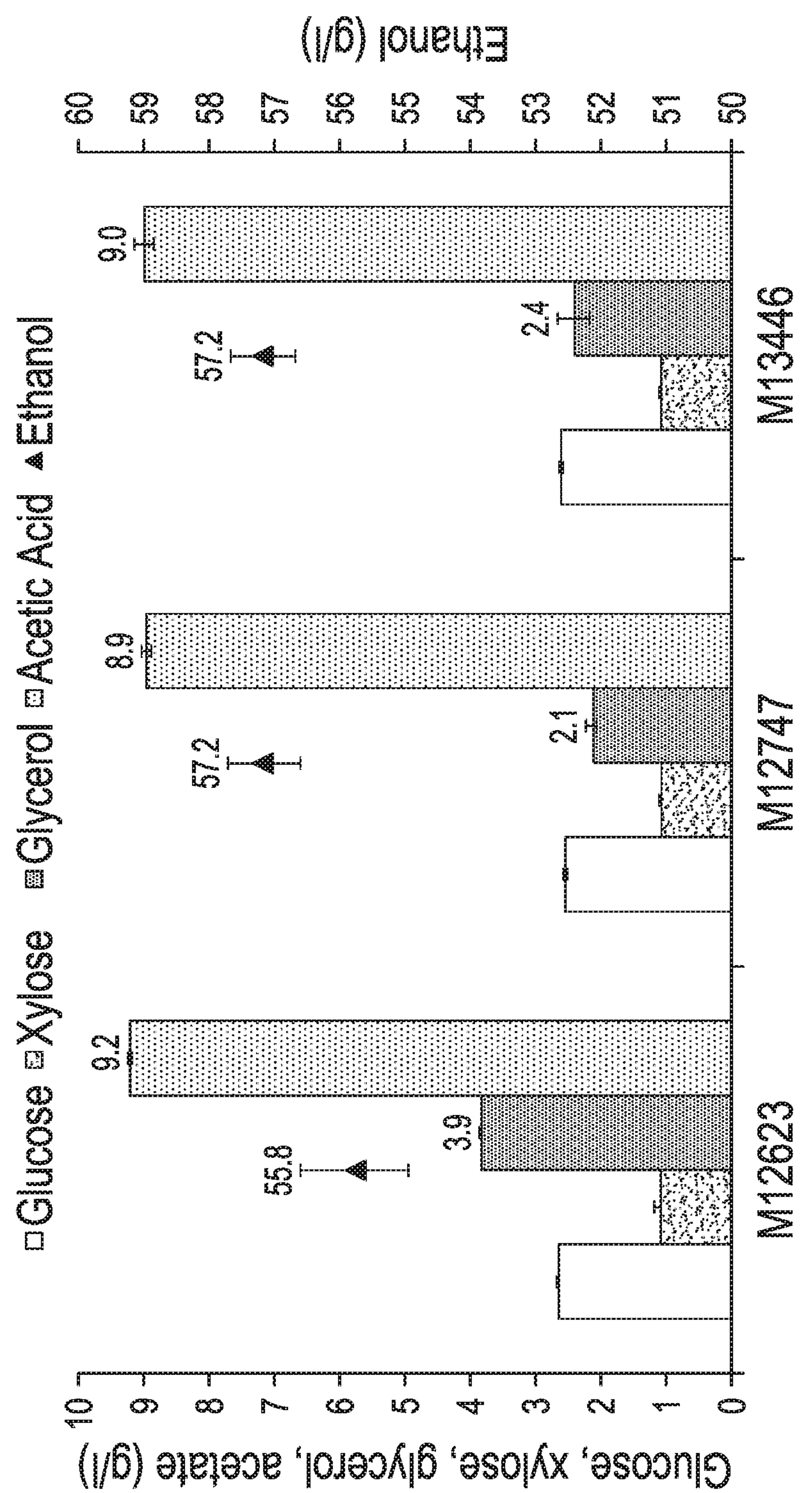
FIG. 2 compares glucose, xylose and acetic acid consumption as well as glycerol and ethanol production in different strains of *S. cerevisiae* on an industrial cellulosic medium. Results are shown as the glucose, xylose, glycerol and acetate content (all provided as g/L, left axis) as well as the ethanol (▲) content (provided as g/L, right axis) in the culture medium of strains M12623, M12747 and M13446 at the end of the fermentation.

Strain M12623 is engineered to utilize xylose and was used as the parent strain for engineering of all strains expressing the RAS2-A66T mutation (as described in WO2017/158189). Strain M13446 additionally expresses the heterologous ADHE enzyme from *B. adolescentis* (SEQ ID NO: 1) and overexpress the native glycerol transporter STL1 (SEQ ID NO: 2) and acetyl-CoA synthetase ACS2 (SEQ ID NO: 3). Strain M13446 exhibits acetate consumption, reduced glycerol production and increased ethanol production in a challenging industrial cellulosic substrate compare to M12623 (FIG. 2) without any negative impact on fermentation rates (FIG. 1). FIG. 1 also shows that a strain with a gpd1 deletion (M12613) showed a decreased fermentation rate in relation to a GPD+ strain with otherwise comparable genotypes (M13446). Strain M12747, containing a deletion of GPD2 in addition to the modifications found in M13446, exhibited similar acetate consumption and increased ethanol titers indicating that a gpd2 deletion is not always necessary for, or beneficial to, conversion of acetate into ethanol (FIG. 2).

Figure 3:
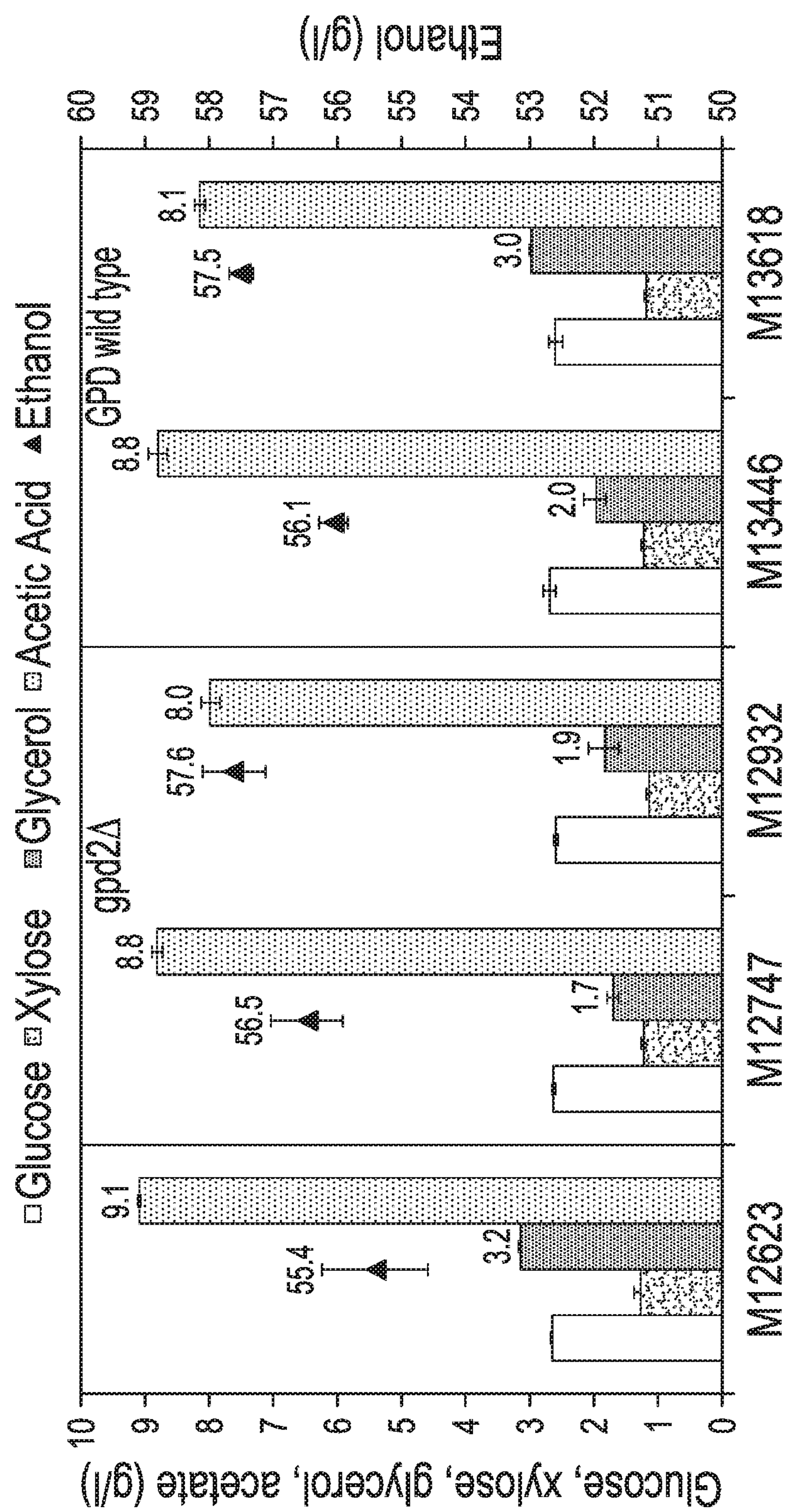
FIG. 3 compares glucose, xylose and acetic acid consumption as well as glycerol and ethanol production in different strains of *S. cerevisiae* on an industrial cellulosic medium. Results are shown as the glucose, xylose, glycerol and acetate content (all provided as g/L, left axis) as well as the ethanol (▲) content (provided as g/L, right axis) in the culture medium of strains M12623, M12747, M12932, M13446 and M13618 at the end of the fermentation.
Figure 4:
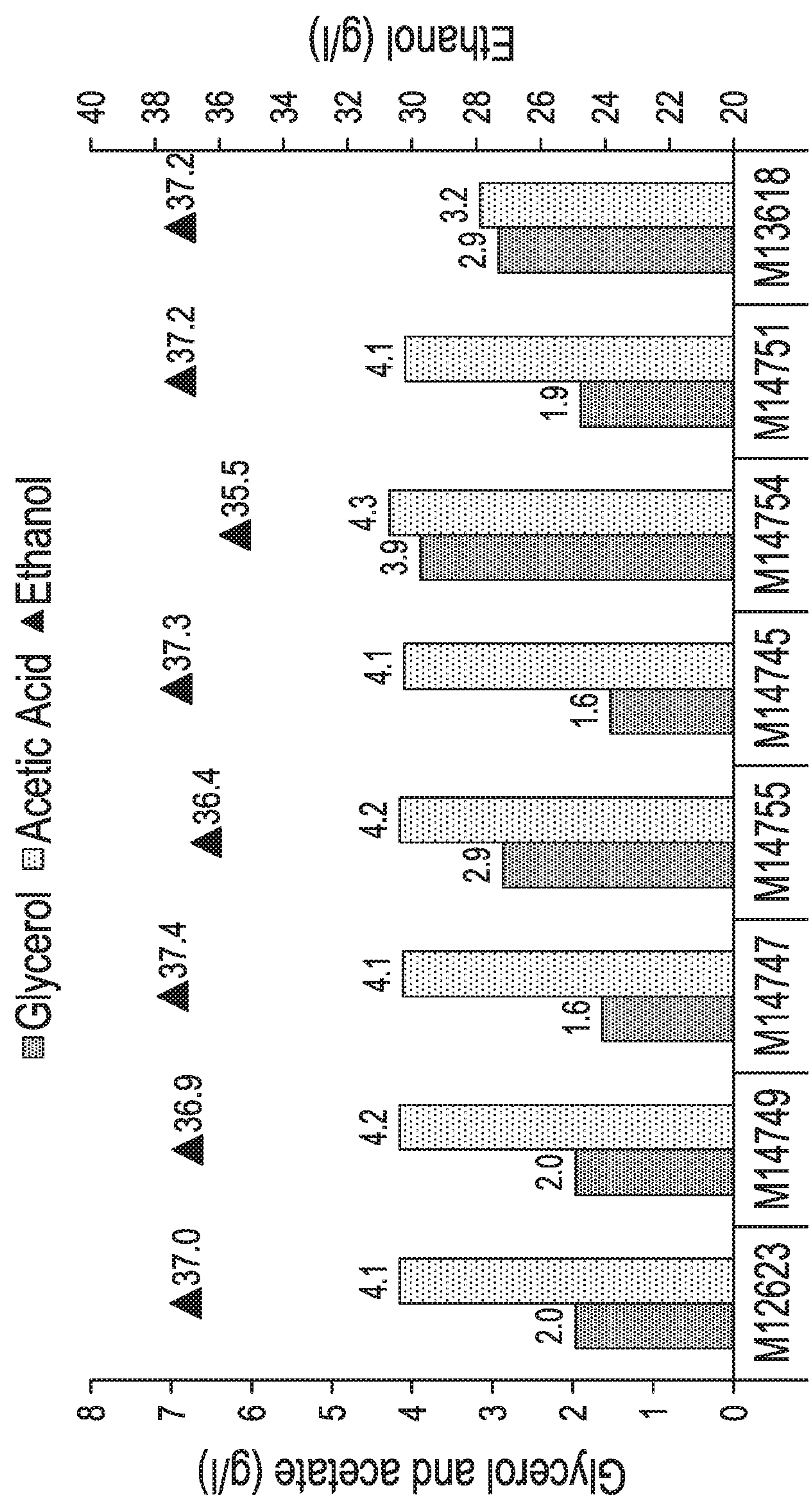
FIG. 4 compares acetic acid consumption as well as glycerol and ethanol production in different strains of *S. cerevisiae*. Results are shown as the glycerol and acetate content (all provided as g/L, left axis) as well as the ethanol (▲) content (provided as g/L, right axis) in the culture medium of strains M12623, M14749, M14747, M14755, M14745, M14754, M14751, M13446 and M13618 at the end of the fermentation on a $YPD_{80}A_4$ (10 g/L yeast extract, 20 g/Lpeptone, 80 g/L glucose, 4 g/L acetate) medium.

Strains M12747 and M13446 were further engineered to also express a heterologous NADPH-specific ADH from *Entamoeba histolytica* (EhADH1, SEQ ID NO: 4), resulting in strains M12932 and M13618, respectively. This was done in an attempt to increase anaerobic NADH availability for the acetate utilization pathway and glycerol production. Although the incorporation of *E. histolytica* ADH1 increased glycerol biosynthesis more in the GPD2+ M13618 than in the d2-M12932 in a cellulosic substrate derived from a thermochemically and enzymatically pretreated plant material substrate, M13618 still produced less glycerol than the M12623 parent strain, and similar improvements in final ethanol and acetate titers were obtained with or without the gpd2 deletion (FIG. 3). Thus, overexpression of ADHE, STL1 and ACS2 can increase ethanol titers through acetate utilization, even in strains overproducing NADH (through the overexpression of EhADH1), without causing glycerol overproduction beyond the wild-type level.

Figure 5:
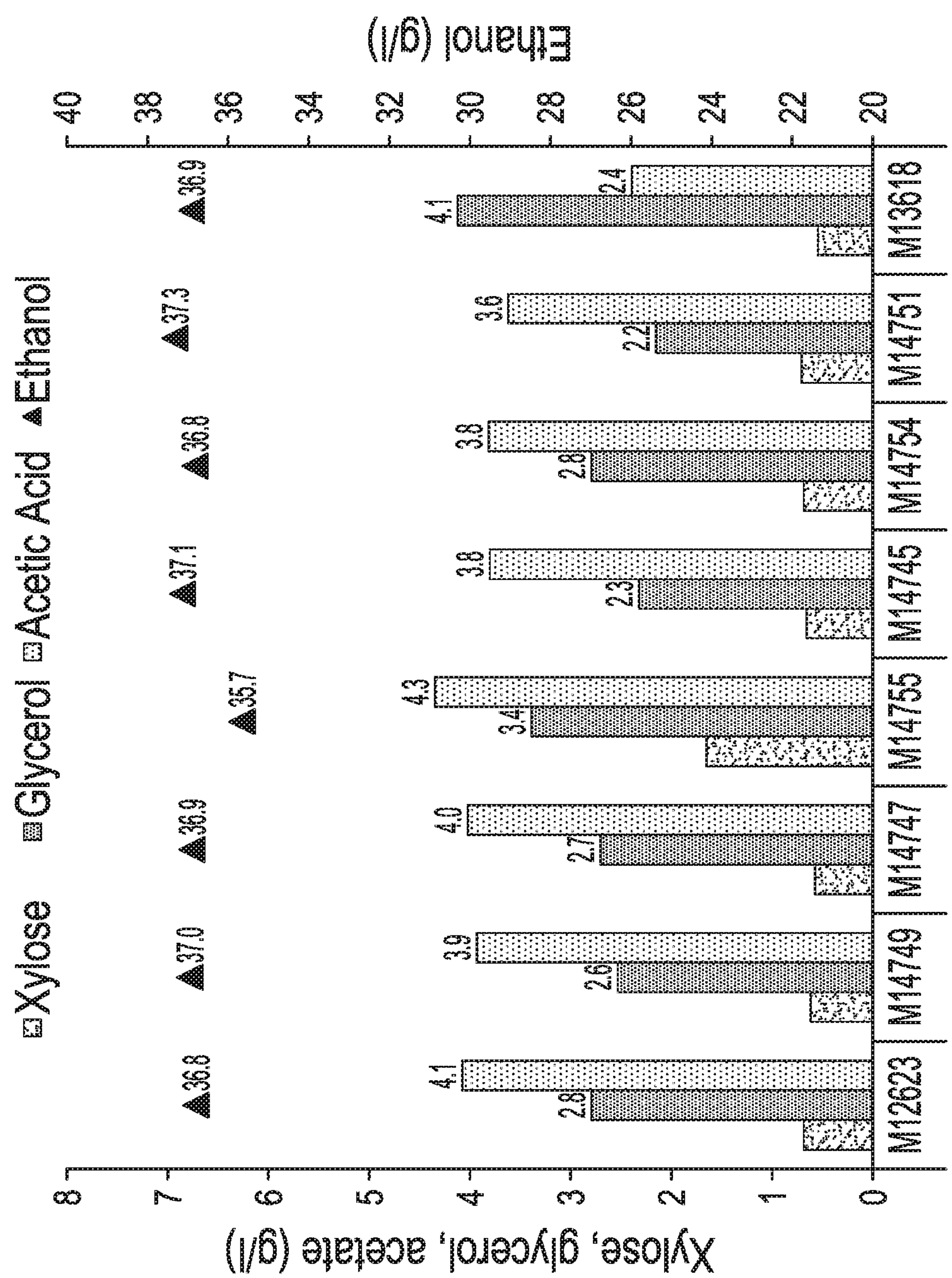
FIG. 5 compares xylose and acetic acid consumption as well as glycerol and ethanol production in different strains of *S. cerevisiae*. Results are shown as the xylose, glycerol and acetate content (all provided as g/L, left axis) as well as the ethanol (1) content (provided as g/L, right axis) in the culture medium of strains M12623, M14749, M14747, M14755, M14745, M14754, M14751, M13446 and M13618 at the end of the fermentation on a $YPX_{80}A_4$ (10 g/L yeast extract, 20 g/Lpeptone, 80 g/L glucose, 4 g/L acetate) medium.

The impact of the various genetic modifications in YP acetate media, with either glucose as the main carbon source, was then investigated. The combination of ADHE and STL1 overexpression (see strain M14745) was effective in reducing glycerol titers and increasing ethanol titers in both media, but acetate uptake was not apparent in the YPD media. Nevertheless, the results in the YPX medium indicated that adhE and STL1 alone enable acetate consumption with the addition of ACS2 providing additional benefit (compare strains M12623, M14745, and M14751 in FIG. 5). The highest acetate uptake was observed in strain M13618, with increased expression of adhE (8 copies) and introduction of the *E. histolytica* ADH1, although improvements in ethanol titer above the parent strain M12623 were modest in both media. These results also show that M13618 supported increased acetate conversion in media without addition of a co-substrate such as glycerol.

Figure 6:
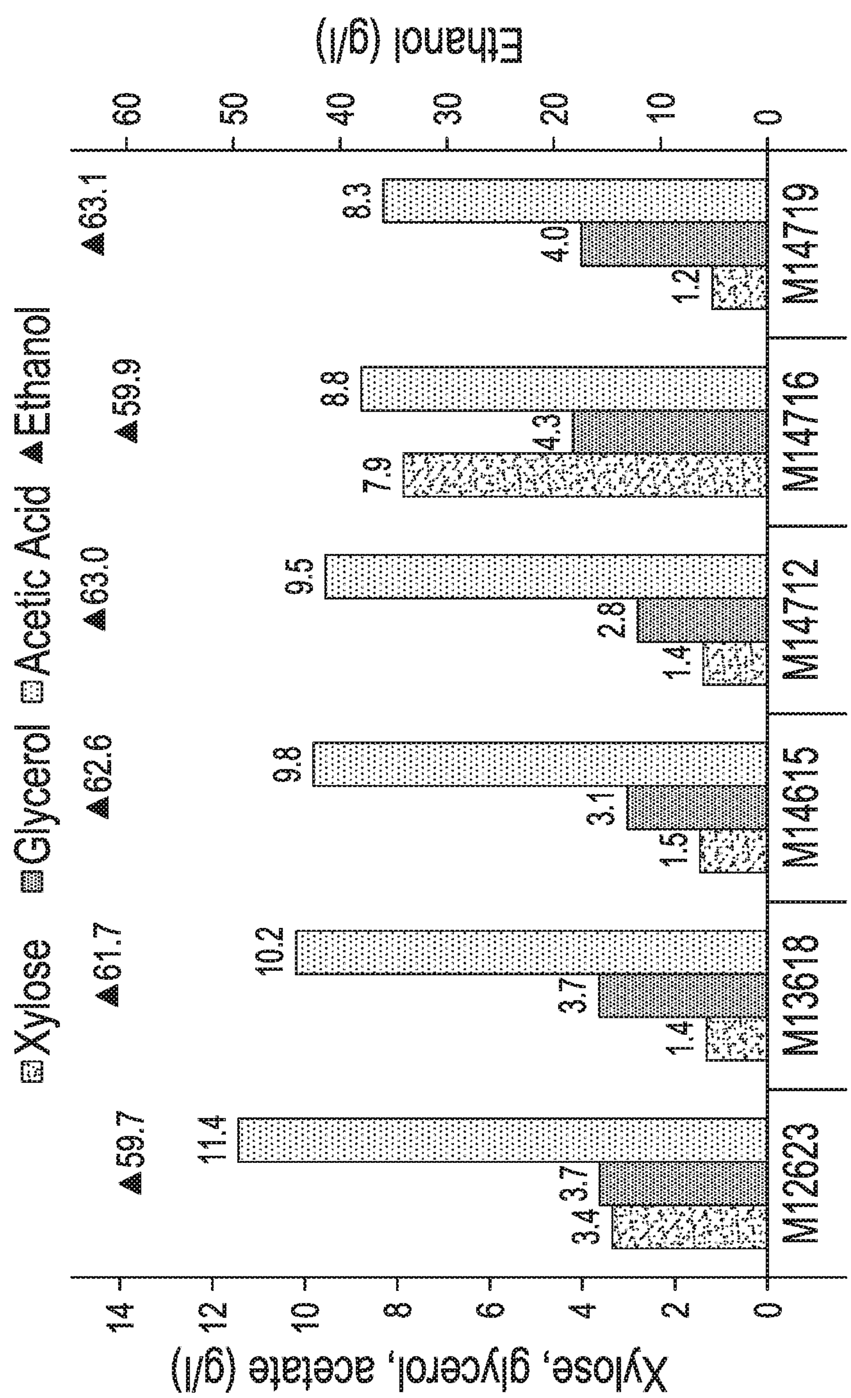
FIG. 6 compares xylose and acetic acid consumption as well as glycerol and ethanol production in different strains of *S. cerevisiae* on an industrial cellulosic medium. Results are shown as the xylose, and acetate content (all provided as g/L, left axis) as well as the ethanol (▲) content (provided as g/L, right axis) in the culture medium of strains M12623, M13618, M14615, M14712, M14716, and M14719 at the end of the fermentation.

It was then determined if ADHE expression was limited in M13618 and if ADHE could effectively compete with the glycerol synthesis pathway for the additional NADH generated through expression of EhADH1. The ADHE copy number was thus increased from 8 (M13618) to 10 (M14615) to 12 (M14712), which significantly improved ethanol titers in industrial hydrolysate by reducing glycerol production and increasing acetate consumption (FIG. 6). The strains with the engineered acetate-to-ethanol pathway also showed improved xylose fermentation compared to the M12623 parent strain, perhaps due to increased media detoxification and increased strain robustness.

Figure 7:
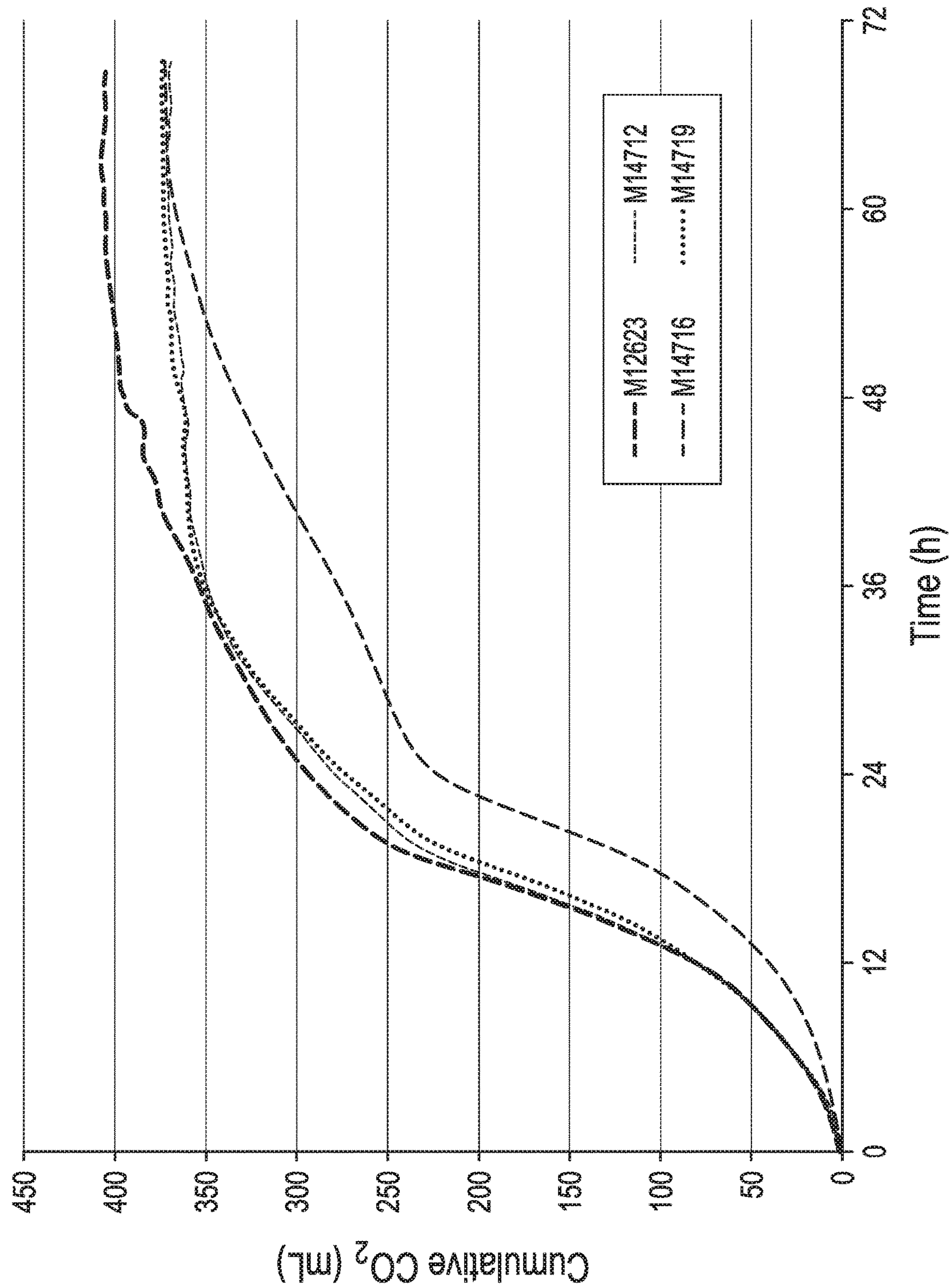
FIG. 7 compares the fermentation rate of different *S. cerevisiae* strains. Results are shown as the cumulative $CO_2$ production (measured as mL) in function of fermentation time (measured in hours) for strains M12623, M14712, M14716 and M14719.

It was then tested if acetate conversion could be further stimulated by increasing the availability of NADPH, by increasing the expression of genes in the oxidative pentose phosphate pathway (ZWF, GND1, SOL3). Interestingly, the results in FIG. 6 using an industrial cellulosic medium show that ZWF1 overexpression by itself (M14716) improved acetate consumption but resulted in decreased xylose-utilization. When ZWF1 overexpression was combined with SOL3 and GND1 overexpression (M14719), acetate consumption further increased and xylose-utilization improved (FIG. 6). The fermentation rates mirror the results seen in the HPLC analysis (FIG. 7).

Figure 8:
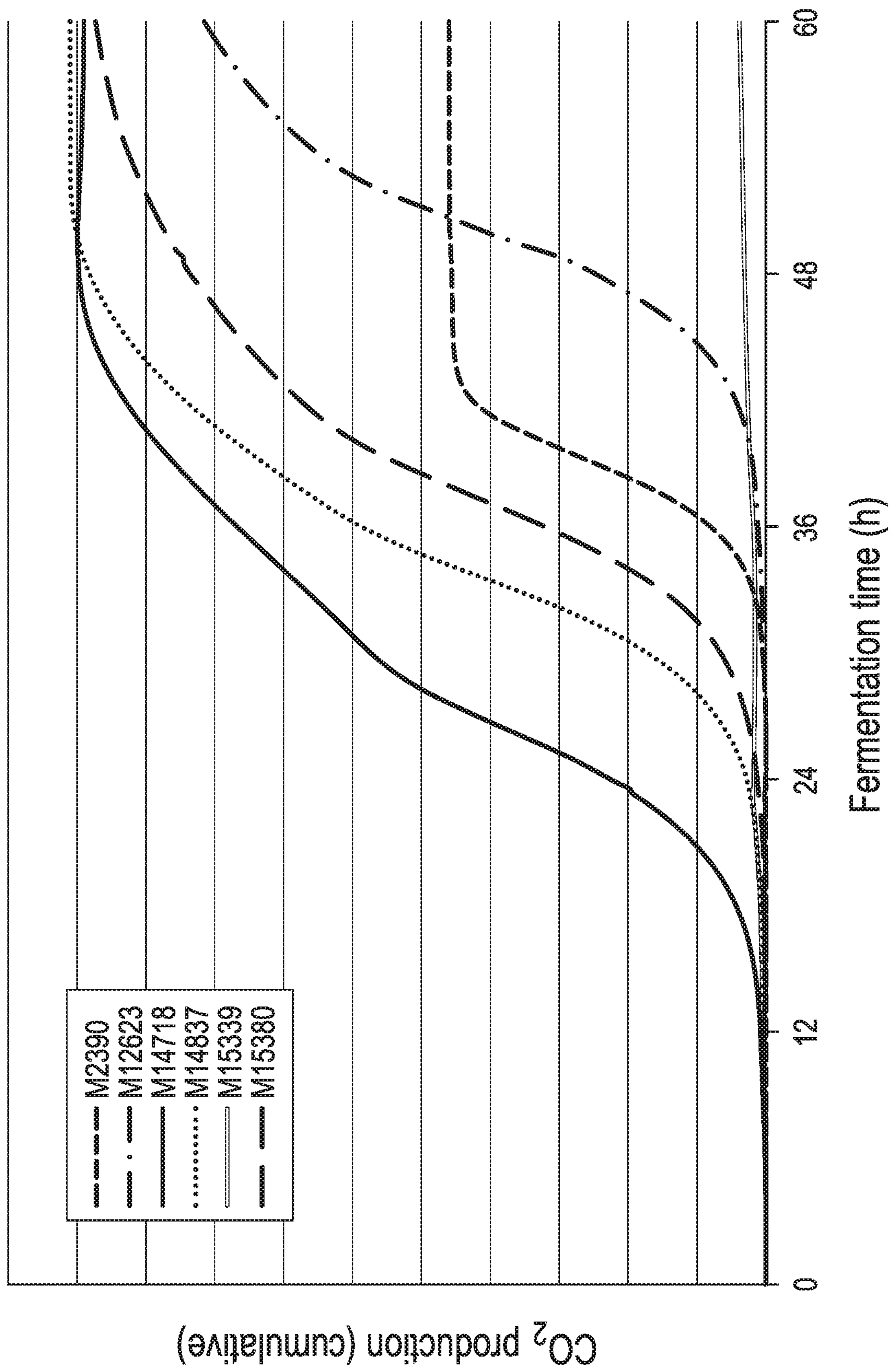
FIG. 8 compares the fermentation rate of different *S. cerevisiae* strains. Results are shown as the cumulative $CO_2$ production (measured as mL) in function of fermentation time (measured in hours) for strains M2390, M12623, M14718, M14837, M15339 and M15380 on a $YPD_{60}X60Ace_9$ (10 g/L yeast extract, 20 g/L peptone, 60 g/L dextrose, 60 g/L xylose, and 9 g/L acetic acid from potassium acetate set at an initial pH of 4.9 using sulfuric acid) medium.
Figure 9:
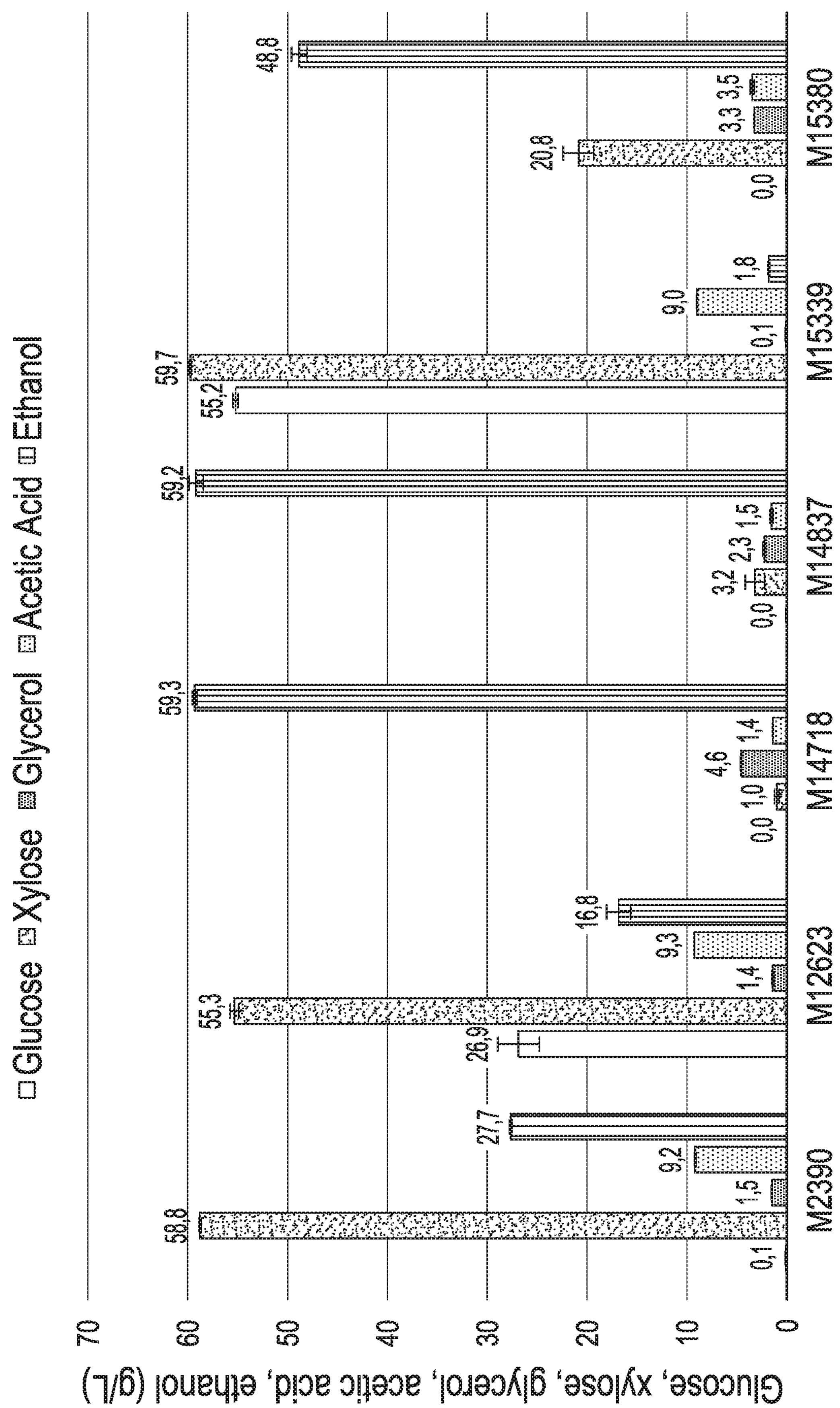
FIG. 9 compares glucose, xylose and acetic acid consumption as well as glycerol and ethanol production in different strains of *S. cerevisiae*. Results are shown as the glucose, xylose, glycerol and acetate content (all provided as g/L, left axis) as well as the ethanol content (provided as g/L, right axis) in the culture medium of strains M2390, M12623, M14718, M14837, M15339, M15380 at the end of the fermentation on a $YPD_{60}X60Ace_9$ (10 g/L yeast extract, 20 g/L peptone, 60 g/L dextrose, 60 g/L xylose, and 9 g/L acetic acid from potassium acetate set at an initial pH of 4.9 using sulfuric acid) medium.

Having improved the acetate conversion and strain robustness through increased adhE expression, expression of EhADH1 and overexpression of ZWF1, GND1, and SOL3, the question of the benefit of modifying native glycerol production was revisited. Strain M14718 was used as the parent to create strains with gpd2 deleted (M14837), gpd1 deleted (M15380), or both gpd1 and gpd2 deleted (M15339). The deletion of either gpd1 or gpd2 resulted in a slower fermentation than M14718 on $YPD_{60}X_{60}Ace_9$ media (10 g/L yeast extract, 20 g/L peptone, 60 g/L glucose, 60 g/L xylose, 9 g/L acetate, FIG. 8). M14718 also had faster fermentation kinetics than the unengineered strain M2390 and the strain containing only the modifications enabling xylose-utilization (M12623). The HPLC results show M14718 consumed more acetate, glucose and xylose than either M14837 (gpd2 deletion), M15380 (gpd1 deletion), or M15339 (gpd1 and gpd2 deletions) and produced the highest ethanol titer (FIG. 9). This data indicates that the presence of GPD1 and GPD2 (i.e., the native glycerol pathway) in a strain provides increased robustness and improved strain performance in challenging substrates.

Figure 10:
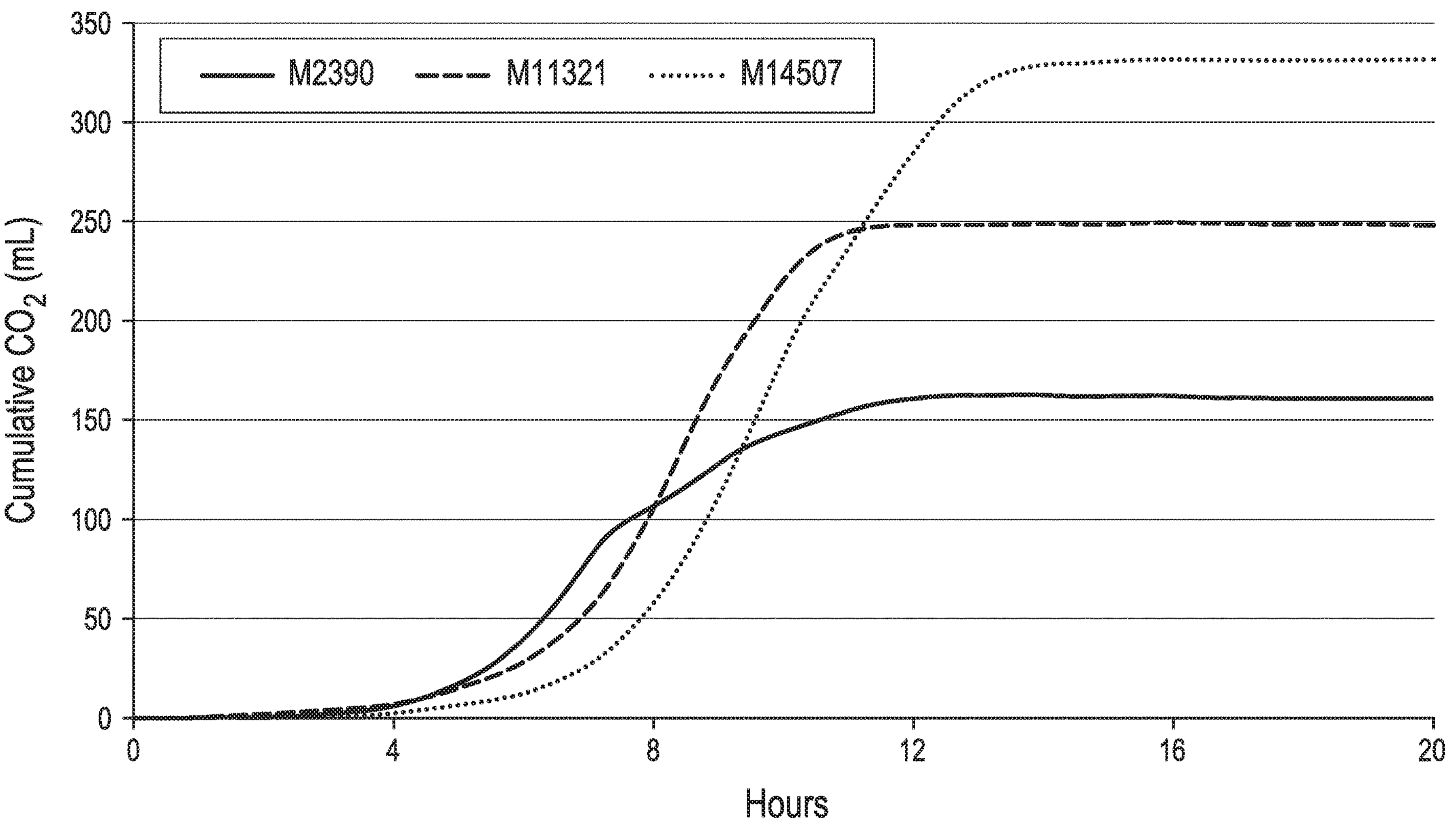
FIG. 10 compares the fermentation rate of different *S. cerevisiae* strains. Results are shown as the cumulative $CO_2$ production (measured as mL) in function of fermentation time (measured in hours) for strains M2390, M11321 and M14507 in $YPD_{20}X_{10}A_{10}Ace_4Gly_1$ (10 g/L yeast extract, 20 g/L peptone, 20 g/L glucose, 10 g/L xylose, 10 g/L arabinose, 4 g/L acetate from potassium acetate, and 1 g/L glycerol) medium.
Figure 11:
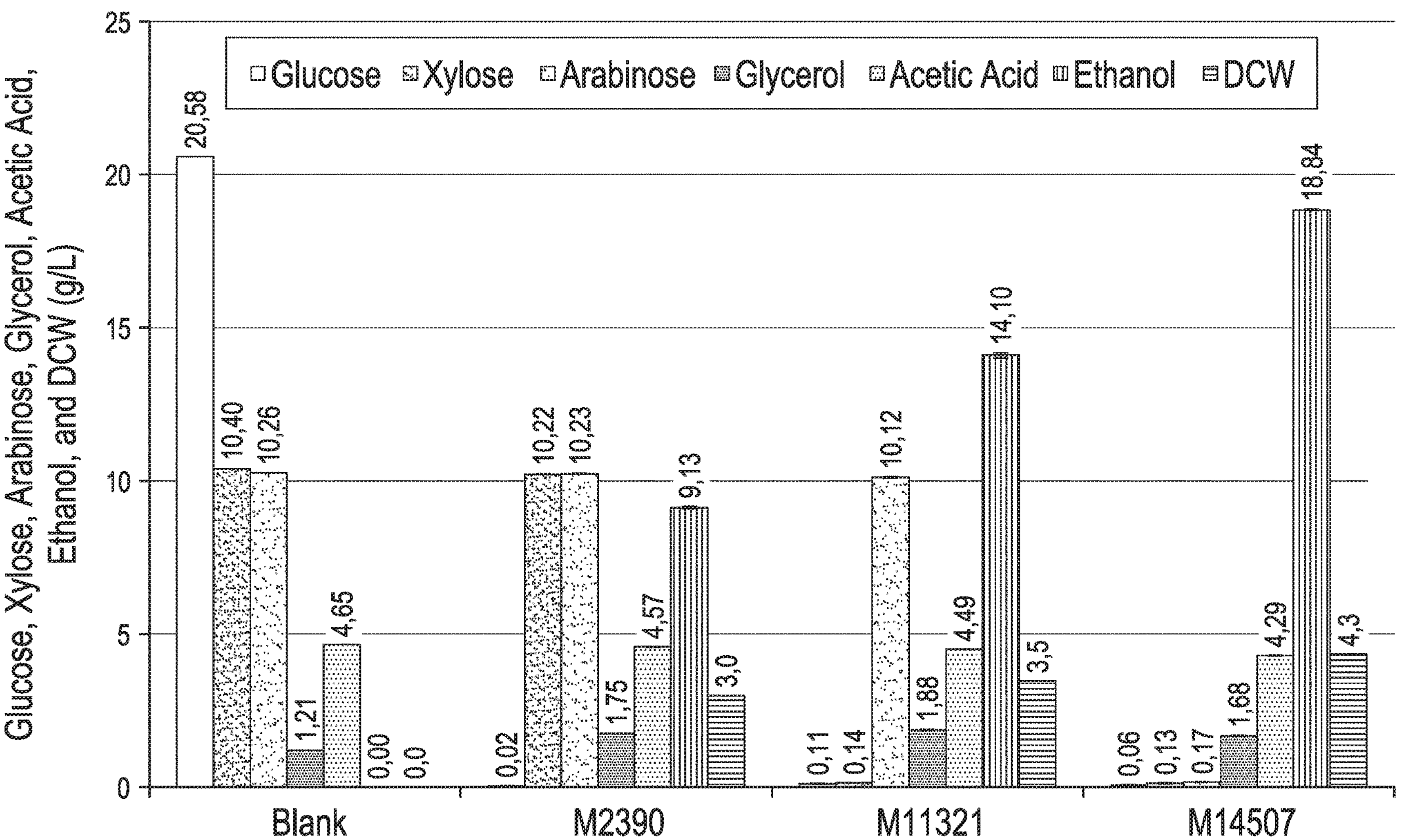
FIG. 11 compares glucose, xylose, acetic acid and arabinose consumption as well as glycerol and ethanol production in different strains of *S. cerevisiae*. Results are shown as the glucose, xylose, glycerol, acetate, arabinose and ethanol content (all provided as g/L) in an unfermented medium ("Blank") or the culture medium of strains M2390, M11321 and M14507 at the end of the fermentation on a $YPD_{20}X_{10}A_{10}Ace_4Gly_1$ (10 g/L yeast extract, 20 g/L peptone, 20 g/L glucose, 10 g/L xylose, 10 g/L arabinose, 4 g/L acetate from potassium acetate, and 1 g/L glycerol) medium.

The ability to combine technology for fermenting arabinose with acetate conversion was demonstrated using strain M14507 (engineered to express the *B. thetaiotaomicron* araA, araB, and araD genes). M14507 also contains the pathway for xylose fermentation found in the other strains described above as well as expression of Ba adhE and overexpression of STL1 and ACS2. In defined media $YPD_{20}X_{10}A_{10}Ace_4Gly_1$ (10 g/L yeast extract, 20 g/L peptone, 20 g/L glucose, 10 g/L xylose, and 10 g/L arabinose, 4 g/L acetate, and 1 g/L glycerol) strain M14507 consumed all available glucose, xylose, and arabinose as well as ~0.3 g/L acetate resulting in the highest ethanol titer of the tested strains (FIG. 11) and also the highest ethanol yield on gram sugar consumed (Table 2). Strain M14507 also had the lowest glycerol of the three strains despite having consumed 10 and 20 g/L more sugar and generating the greatest amount of cell mass (FIG. 11). The fermentation rate and lag time for M14507 was similar to M2390 and M11321 indicating no negative interactions of the additional arabinose engineering on strain performance (FIG. 10).

TABLE 2

Summary of yield on glucose, xylose, and arabinose ($YPD_{20}X_{10}A_{10}Ace_4Gly_1$) under anaerobic conditions. Yield is calculated as gram of product produced per gram of sugar consumed (glucose + xylose + arabinose).

| | | $YPD_{20}X_{10}A_{10}Ace_4Gly_1$ | | |
|---|---|---|---|---|
| | | M2390 | M11321 | M14507 |
| Yield (g/g) | Ethanol | 0.440 | 0.457 | 0.461 |
| | Glycerol | 0.026 | 0.022 | 0.011 |
| | Acetic acid | −0.004 | −0.005 | −0.009 |
| | DCW | 0.140 | 0.109 | 0.104 |
| Max Ethanol (g/L) | | 9.13 | 14.10 | 18.84 |

Figure 12:
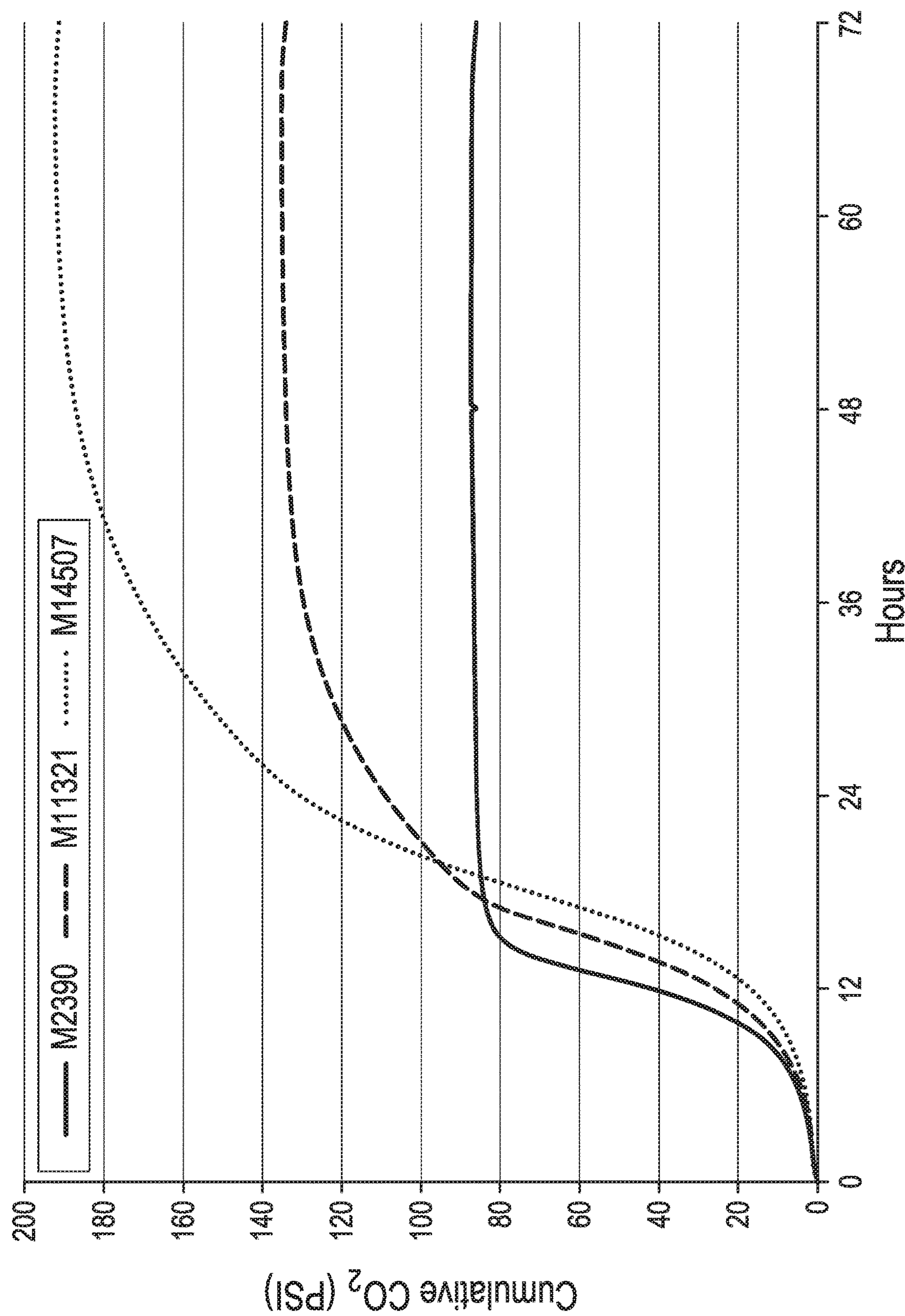
FIG. 12 compares the fermentation rate of different *S. cerevisiae* strains. Results are shown as the cumulative $CO_2$ production (measured as PSI) in function of fermentation time (measured in hours) for strains M2390, M11321 and M14507 in a commercial corn fiber cellulosic substrate.

When used to ferment a corn fiber cellulosic substrate, strain M14507 appeared to have largely completed the fermentation after about 54 hours (FIG. 12). Strain M2390 stopped fermenting after about 24 hours at a significantly lower CO2 level than M11321 and M14507 with M11321's fermentation ending around 48 hours with a lower $CO_2$ level than M14507 (FIG. 12). The 72 hours HPLC samples showed that M14507 consumed the majority of the xylose and arabinose resulting in about 18 g/L more ethanol produced than the control strain M2390 and about 8 g/L more ethanol produced than M11321, with a ~109% and ~33% increase in ethanol titer respectively in this corn fiber fermentation (Table 3). A slight decrease in xylose concentration is observed for M2390 and is most likely due partly to the conversion of xylose into xylitol by endogenous aldose reductases enzymes as well as consumption of other compounds which cannot be distinguished from xylose using our HPLC analysis methods. Strains M11321 and M14507 consumed the same amount of glucose and xylose with M14507 producing 0.7 g/L less glycerol (20% reduction) and consuming 0.5 g/L more acetate compared to M11321.

TABLE 3

HPLC results for samples taken at 72 hours from the corn fiber cellulosic substrate fermentation. All values are in g/L.

| | Glucose | Xylose | Arabinose | Glycerol | Acetic Acid | Ethanol |
|---|---|---|---|---|---|---|
| Substrate | 33.0 | 28.8 | 17.8 | 6.2 | 4.0 | 0.0 |
| M2390 | 0.0 | 27.0 | 17.1 | 8.2 | 4.1 | 16.2 |
| M11321 | 0.7 | 8.1 | 17.1 | 9.6 | 4.5 | 25.6 |
| M14507 | 0.0 | 3.8 | 1.1 | 8.9 | 4.0 | 34.0 |

While the invention has been described in connection with specific embodiments thereof, it will be understood that the scope of the claims should not be limited by the preferred embodiments set forth in the examples, but should be given the broadest interpretation consistent with the description as a whole.

REFERENCES

De Bont, J. A. M., Teunissen, A. W. R. H., 2011. Yeast Strains Engineered to Produce Ethanol from Acetic Acid and Glycerol. WO2011149353 (A1).

De Bont, J. A. M., Teunissen, A. W. R. H., Klaassen, P., Hartman, W. W. A., Van Beusekom, S., 2015. Yeast strains engineered to produce ethanol from acetic acid and glycerol. US2015176032 (A1).

Guadalupe Medina, V., Almering, M. J. H., van Maris, A. J. A., Pronk, J. T., 2010. Elimination of glycerol production in anaerobic cultures of a *Saccharomyces cerevisiae* strain engineered to use acetic acid as an electron acceptor. Appl Env. Microbiol 76, 190-195. doi:10.1128/AEM.01772-09.

Guadalupe Medina, V., Metz, B., Oud, B., van der Graaf, C. M., Mans, R., Pronk, J. T., van Maris, A. J. A., 2014. Evolutionary engineering of a glycerol-3-phosphate dehydrogenase-negative, acetate-reducing *Saccharomyces cerevisiae* strain enables anaerobic growth at high glucose concentrations. Microb. Biotechnol. 7, 44-53. doi:10.1111/1751-7915.12080.

Henningsen, B. M., Hon, S., Covalla, S. F., Sonu, C., Argyros, D. A., Barrett, T. F., Wiswall, E., Froehlich, A. C., Zelle, R. M., 2015. Increasing anaerobic acetate consumption and ethanol yield in *Saccharomyces cerevisiae* with NADPH-specific alcohol dehydrogenase. Appl. Environ. Microbiol. 81, 8108-8117. doi:10.1128/AEM.01689-15.

Onishi, T., Tada, N., Yasutani, N., Katahira, S., Ishida, N., Nagura, R., 2016. Method for Producing Ethanol Using Recombinant Yeast. US2016002674 (A1).

US Patent Application published under 2016/040152.

Wei, N., Quarterman, J., Kim, S. R., Cate, J. H. D., Jin, Y.-S., 2013. Enhanced biofuel production through coupled acetic acid and xylose consumption by engineered yeast. Nat. Commun. 4, 2580. doi:10.1038/ncomms3580.

Zhang, G.-C., Kong, I. I., Wei, N., Peng, D., Turner, T. L., Sung, B. H., Sohn, J.-H., Jin, Y.-S., 2016. Optimization of an acetate reduction pathway for producing cellulosic ethanol by engineered yeast. Biotechnol. Bioeng. 113, 2587-2596. doi:10.1002/bit.26021.

Zhang, L., Tang, Y., Guo, Z., Ding, Z., Shi, G., 2011. Improving the ethanol yield by reducing glycerol formation using cofactor regulation in *Saccharomyces cerevisiae*. Biotechnol. Lett. 33, 1375-1380. doi:10.1007/s10529-011-0588-6.

What is claimed is:

1. A recombinant microbial host cell comprising:

a first genetic modification for increasing, when compared to a control microbial host cell lacking the first genetic modification, the activity of one or more proteins that function in a first metabolic pathway to convert acetate into an alcohol in the microbial host cell, wherein the one or more proteins that function in the first metabolic pathway comprise a protein having acetylating acetaldehyde dehydrogenase activity or a protein having acetylating acetaldehyde dehydrogenase activity and alcohol dehydrogenase activity (ADHE);

a second genetic modification for increasing, when compared to the control microbial host cell lacking the second genetic modification, the activity of one or more proteins that function in a second metabolic pathway to import glycerol in the recombinant microbial host cell, wherein the protein that function in the second metabolic pathway is an STL1 polypeptide; and a third genetic modification for increasing, when compared to the control microbial host cell lacking the third genetic modification, the activity of one or more proteins that function in a third metabolic pathway to convert a C5 carbohydrate into the alcohol in the microbial host cell, wherein the one or more proteins that function in the third metabolic pathway comprise a protein having xylose isomerase activity from the genus *Catonella* sp.; and wherein the recombinant microbial host cell comprises and natively expresses native proteins that function in a fourth native metabolic pathway to produce glycerol in the microbial host cell, wherein the native proteins that function in the fourth native metabolic pathway to produce glycerol comprise a GPD1 protein, a GPD2 protein, a GPP1 protein and a GPP2 protein.

2. The recombinant microbial host cell of claim 1, wherein the alcohol is ethanol.

3. The recombinant microbial host cell of claim 1, wherein the one or more proteins that function in the first, second or third metabolic pathway are heterologous proteins.

4. The recombinant microbial host cell of claim 1, wherein the one or more protein that function in the first metabolic pathway further comprises a protein having acetyl-CoA synthetase activity or is an ACS2 polypeptide.

5. The recombinant microbial host cell of claim 1, further comprising at least one of a first additional genetic modification, wherein the first additional genetic modification is:

a deletion in at least one an aldose reductase gene;

a mutation in a polypeptide encoded by an iron-sulfur cluster gene; or a mutation in a RAS2 polypeptide.

6. The recombinant microbial host cell of claim 5, wherein the aldose reductase gene is a GRE3 gene and/or a YPR1 gene.

7. The recombinant microbial host cell of claim 5, wherein the iron sulfur cluster gene is a YFH1 gene, a ISU1 gene and/or a NFS1 gene.

8. The recombinant microbial host cell of claim 1 further comprising a fifth genetic modification for increasing the activity of one or more heterologous proteins that function in a fifth metabolic pathway for increasing the availability of electrons in the form of a reduced redox cofactor in the microbial host cell.

9. The recombinant microbial host cell of claim 8, wherein the fifth genetic modification is for increasing the activity of a NADPH-dependent alcohol dehydrogenase.

10. The recombinant microbial host cell of claim 9, wherein the NADPH-dependent alcohol dehydrogenase is an ADH1 polypeptide.

11. The recombinant microbial host cell of claim 9, further comprising a second additional genetic modification for increasing the activity of a protein capable of producing NADPH.

12. The recombinant microbial host cell of claim 11, wherein the protein capable of producing NADPH is at least one of a ZWF1 protein, a SOL3 protein and/or a GND1 protein.

13. The recombinant microbial host cell of claim 1 which is a yeast host cell.

14. The recombinant microbial host cell of claim 13 wherein the yeast host cell is a yeast of genus *Saccharomyces.*

15. The recombinant microbial host cell of claim 14, wherein the yeast of genus *Saccharomyces* is a yeast of species *Saccharomyces cerevisiae.*

16. The recombinant microbial host cell of claim 1, wherein the protein having acetylating acetaldehyde dehydrogenase and alcohol dehydrogenase activity is an ADHE polypeptide from the genus *Bifidobacterium* sp. or from *Bifidobacterium adolescentis.*

17. The recombinant microbial host cell of claim 4, wherein the ACS2 polypeptide is from the genus *Saccharomyces* sp. or from *Saccharomyces cerevisiae.*

18. The recombinant microbial host cell of claim 1, wherein the STL1 polypeptide is from the genus *Saccharomyces* sp. or *Pichia* sp.; or from *Saccharomyces cerevisiae* or *Pichia sorbitophila.*

19. The recombinant microbial host cell of claim 1, wherein the protein having xylose isomerase activity is from *Catonella morbi.*

20. The recombinant microbial host cell of claim 1, wherein the one or more proteins that function in the third metabolic pathway further comprise a protein having xylulokinase activity, a protein having transketolase activity, a protein having transaldolase activity, a protein having ribose-5-phosphate isomerase activity, and/or a protein having ribulose-phosphate 3-epimerase activity.

21. The recombinant microbial host cell of claim 1, wherein the one or more proteins that function in the third metabolic pathway further comprise an arabinose transporter, an ARAA polypeptide, an ARAB polypeptide, and/or an ARAD polypeptide.

22. The recombinant microbial host cell of claim 21, wherein at least one of the ARAA, ARAB or ARAD is from the genus *Bacteroides* sp. or from *Bacteroides* thetaiotaomicron.

* * * * *